US010087215B2

(12) United States Patent
Leshchiner et al.

(10) Patent No.: US 10,087,215 B2
(45) Date of Patent: Oct. 2, 2018

(54) STABILIZED SOS1 PEPTIDES

(71) Applicant: DANA-FARBER CANCER INSTITUTE, INC., Boston, MA (US)

(72) Inventors: Elizaveta Leshchiner, Belmont, MA (US); Loren D. Walensky, Newton Centre, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 42 days.

(21) Appl. No.: 14/772,136

(22) PCT Filed: Mar. 14, 2014

(86) PCT No.: PCT/US2014/028436
§ 371 (c)(1),
(2) Date: Sep. 2, 2015

(87) PCT Pub. No.: WO2014/144148
PCT Pub. Date: Sep. 18, 2014

(65) Prior Publication Data
US 2016/0046671 A1 Feb. 18, 2016

Related U.S. Application Data

(60) Provisional application No. 61/798,254, filed on Mar. 15, 2013.

(51) Int. Cl.
*A61K 38/10* (2006.01)
*C07K 7/08* (2006.01)
*C07K 14/47* (2006.01)
*C07K 14/705* (2006.01)
*A61K 38/00* (2006.01)

(52) U.S. Cl.
CPC ............... *C07K 7/08* (2013.01); *C07K 14/47* (2013.01); *C07K 14/705* (2013.01); *A61K 38/00* (2013.01)

(58) Field of Classification Search
None
See application file for complete search history.

(56) References Cited

U.S. PATENT DOCUMENTS

| 5,446,090 A | 8/1995 | Harris |
| 6,348,558 B1 | 2/2002 | Harris et al. |
| 7,723,468 B2 | 5/2010 | Daffre et al. |
| 2004/0067503 A1 | 4/2004 | Tan et al. |
| 2005/0250680 A1 | 11/2005 | Walensky et al. |

FOREIGN PATENT DOCUMENTS

| WO | WO 1999/14259 | 3/1999 |
| WO | WO 1999/34833 | 7/1999 |
| WO | WO 2008/121767 | 10/2008 |
| WO | WO 2009/108261 | 9/2009 |
| WO | WO 2010/060112 | 5/2010 |
| WO | WO 2010/068684 | 6/2010 |
| WO | WO 2010/148335 | 12/2010 |
| WO | 2012/122059 A1 | 9/2012 |
| WO | WO 2012/122059 | * 9/2012 |

OTHER PUBLICATIONS

Aguirre, A.J., et al., *Activated Kras and Ink4a/Arf deficiency cooperate to produce metastatic pancreatic ductal adenocarcinoma.* Genes Dev 17:3112-3126 (2003).
Altschul et al., *Gapped BLAST and PSI-BLAST: a new generation of protein database search programs*, Nucleic Acids Res. 25(17):3389-3402 (1997).
Bang, et al., *Total Chemical Synthesis of Crambin*, J. Am. Chem. Soc. 126:1377-1383 (2004).
Bird et al, *Chemical synthesis of hydrocarbon-stapled peptides for protein interaction research and therapeutic targeting*, Current Protocols in Chemical Biology, 3(3):99-117 (2011).
Bird et. al., *Synthesis and Biophysical Characterization of Stabilized alpha-Helices of BCL-2 Domains*, Methods in Enzymol., 446:369-386 (2008).
Blackwell et al., *Ring-Closing Metathesis of Olefinic Peptides: Design, Synthesis, and Structural Characterization of Macrocyclic Helical Peptides*, J. Org. Chem., 66: 5291-5302, 2001.
Braun, C.R. et al. *Photoreactive stapled BH3 peptides to dissect the BCL-2 family interactome.* Chem Biol 17(12):1325-33 (2010).
Chen, C.R., et al., *Defective repression of c-myc in breast cancer cells: A loss at the core of the transforming growth factor beta growth arrest program.* Proc Natl Acad Sci USA 98(3): 992-9 (2001).
Devi et al., *Antibodies to poly[(2-8)-alpha-N-acetylneuraminic acid] and poly[(2-9)-alpha-N-acetylneuraminic acid] are elicited by immunization of mice with Escherichia coli K92 conjugates: potential vaccines for groups B and C meningococci and E. coli K1*, Proc. Natl. Acad. Sci. USA 88(16):7175-7179, (1991).
Downward, J. *Targeting RAS signalling pathways in cancer therapy.* Nat Rev Cancer 3(1):11-22 (2003).
Fattom et al., *Serum antibody response in adult volunteers elicited by injection of Streptococcus pneumoniae type 12F polysaccharide alone or conjugated to diphtheria toxoid*, Infect. Immun., 58(7):2309-2312, (1990).
Hidalgo, M. *Pancreatic cancer.* N Engl J Med 362(17):1605-1617 (2010).

(Continued)

*Primary Examiner* — Satyanarayana R Gudibande
(74) *Attorney, Agent, or Firm* — Fish & Richardson P.C.

(57) ABSTRACT

Provided herein are polypeptides containing stabilized therapeutic peptides related to KRAS guanidine exchange factor (SOS1). Also provided are compositions containing these polypeptides and methods of using such peptides in the treatment of cancer that includes administering to a subject one of the polypeptides. This disclosure relates to structurally stabilized therapeutic peptides related to KRAS guanidine exchange factor (SOS1), and methods of using such peptides in the treatment of cancer.

24 Claims, 38 Drawing Sheets
Specification includes a Sequence Listing.

(56) References Cited

OTHER PUBLICATIONS

Hingorani, S.R., et al., Preinvasive and invasive ductal pancreatic cancer and its early detection in the mouse. Cancer Cell 4(6):437-450 (2003).

Karnoub, A.E., et al., *Ras oncogenes: split personalities*. Nat Rev Mol Cell Biol 9(7):517-531 (2008).

Kawamoto et al., Design of Triazole-stapled BCL9 a-Helical Peptides to Target the β-Catenin/B-cell CLL/lymphoma 9 (BCL9) Protein-Protein Interaction, *Journal of Medicinal Chemistry* 55(3):1137-1146 (2012).

Konstantinopoulos, P.A., et al., *Post-translational modifications and regulation of the RAS superfamily of GTPases as anticancer targets*. Nat Rev Drug Discov 6(7):541-555 (2007).

Luo, J., et al., *A genome-wide RNAi screen identifies multiple synthetic lethal interactions with the Ras oncogene*. Cell 137(5):835-848 (2009).

Maurer, T., et al., *Small-molecule ligands bind to a distinct pocket in Ras and inhibit SOS-mediated nucleotide exchange activity*. Proc Natl Acad Sci USA 109(14):5299-5304 (2012).

Normanno, N., et al., *Implications for KRAS status and EGFR-targeted therapies in metastatic CRC*. Nat Rev Clin Oncol 6, 519-527 (2009).

Pitter, K., et al., *Dissection of the BCL-2 family signaling network with stabilized alpha-helices of BCL-2 domains*. Methods Enzymol 446:387-408 (2008).

Rinehart, J., et al., *Multicenter phase II study of the oral MEK inhibitor, CI-1040, in patients with advanced non-small-cell lung, breast, colon, and pancreatic cancer*. J Clin Oncol 22(22):4456-4462 (2004).

Schafmeister et al., *An All-Hydrocarbon Cross-Linking System for Enhancing the Helicity and Metabolic Stability of Peptides*, J. Am. Chem. Soc., 122:5891-5892 (2000).

Singh, A., et al., *Oncogenic K-ras "addiction" and synthetic lethality*. Cell Cycle 8, 2676-2677 (2009).

Singh, A., et al., *TAK1 inhibition promotes apoptosis in KRAS-dependent colon cancers*. Cell 148, 639-650 (2012).

Sun, Q., et al., *Discovery of small molecules that bind to K-Ras and inhibit Sos-mediated activation*. Angew Chem Int Ed Engl 51(25):6140-6143 (2012).

Szu et al., *Comparative immunogenicities of Vi polysaccharide-protein conjugates composed of cholera toxin or its B subunit as a carrier bound to high- or lower-molecular-weight Vi*. Infect. Immun. 57(12):3823-3827 (1989).

Szu et al., *Relation between structure and immunologic properties of the Vi capsular polysaccharide*, Infect. Immun. 59(12):4555-4561,1991.

Szu et al., *Laboratory and preliminary clinical characterization of Vi capsular polysaccharide-protein conjugate vaccines*, Infect. Immun. 62(10):4440-4444, 1994.

Szu et al., *Vi capsular polysaccharide-protein conjugates for prevention of typhoid fever. Preparation, characterization, and immunogenicity in laboratory animals*, J. Exp. Med. 166(5):1510-1524, 1987.

Walensky, L. D. *Activation of Apoptosis in Vivo by a Hydrocarbon-Stapled BH3 Helix*. Science 305, 1466-1470 (2004).

Walensky, L. D. et al. *A Stapled BID BH3 Helix Directly Binds and Activates BAX*. Molecular Cell 24, 199-210 (2006).

Whyte, D.B., et al., *K- and N-Ras are geranylgeranylated in cells treated with farnesyl protein transferase inhibitors*. J Biol Chem 272, 14459-14464 (1997).

Wilen, S. H., et al., *Strategies in Optical Resolutions*, Tetrahedron 33:2725 (1977).

Wilen, S.H. *Tables of Resolving Agents and Optical Resolutions* p. 268 (EX. Eliel, Ed., Univ. of Notre Dame Press, Notre Dame, IN (1972).

Williams et al. *Asymmetric Synthesis of Monosubstituted and a,a-Disubstituted a-Amino Acids via Diastereoselective Glycine Enolate Alkylations*, J. Am. Chem. Soc., 113:9276, (1991).

Williams et al., *Efficient Asymmetric Synthesis of N-tert-Butoxycarbonyl □-Amino Acids Using 4-tert-Butoxycarbonyl- 5,6-Diphenylmorpholin-2-One*: (R)-(Ntert-Butoxycarbonyl)Allylglycine [(4-Pentenoic acid, 2-[[(1,1-dimethylethoxy)carbonyl]amino], (2R)-)], Org. Synth., 80:31-37 (2003).

Yang et al., *[11] Calculation of Protein Conformation from Circular Dichroism*, Methods Enzymol. 130:208-269 (1986).

Platt et al., "Stapling Mimics Noncovalent Interactions of-Carboxyglutamates in Conantokins, Peptidic Antagonists of N-Methyl-D-Aspartic Acid Receptors," *The Journal of Biological Chemistry*, vol. 287, No. 24, pp. 20727-20736, Jun. 8, 2012.

Patgiri et al., "An orthosteric inhibitor of the Ras-Sos interaction," *Nature Chemical Biology*, vol. 7, pp. 585-587, and supplementary pp. 1-29. Jul. 17, 2011.

International Search Report for PCT/US2014/028436 dated Jul. 21, 2014. 5 pages.

Henchey et al., *Contemporary strategies for the stabilization of peptides in the alpha-helical conformation*, Curr Opin Chem Biol. 12(6):692-697 (Dec. 2008).

Leshchiner et al., *Direct inhibition of oncogenic KRAS by hydrocarbon-stapled SOS1 helices*, Proc Natl Acad Sci U S A. 112(6):1761-1766 (Feb. 10, 2015).

Supplementary European Search Report for Application No. EP 14765774, dated Sep. 22, 2016 (3 pages).

Bird et al., *Hydrocarbon double-stapling remedies the proteolytic instability of a lengthy peptide therapeutic*, PNAS, 107(32):14093-14098, Aug. 10, 2010.

\* cited by examiner

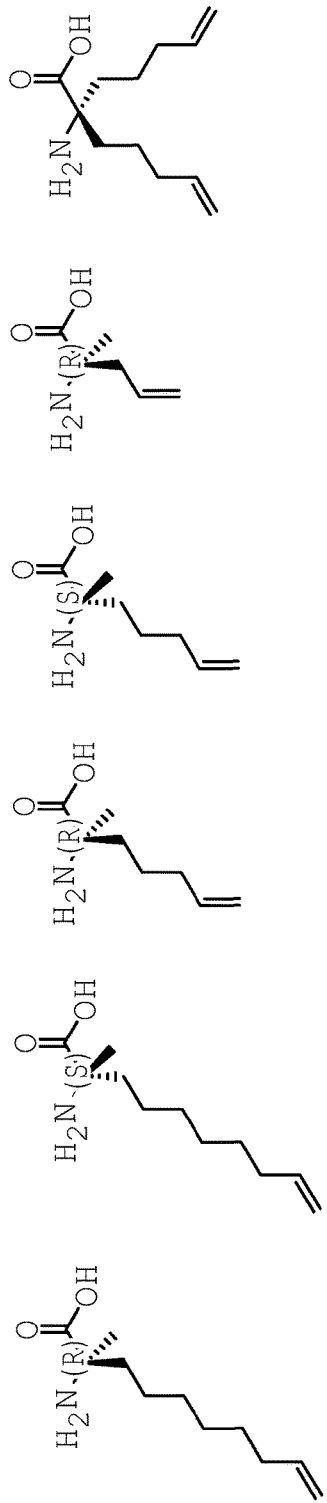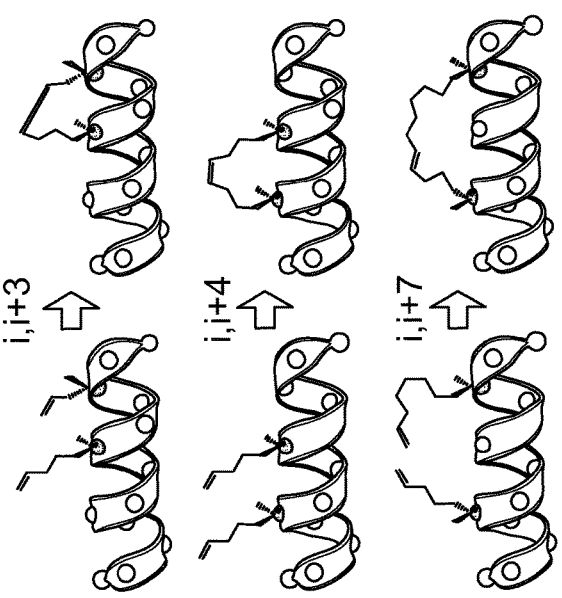
FIG. 1A
FIG. 1B

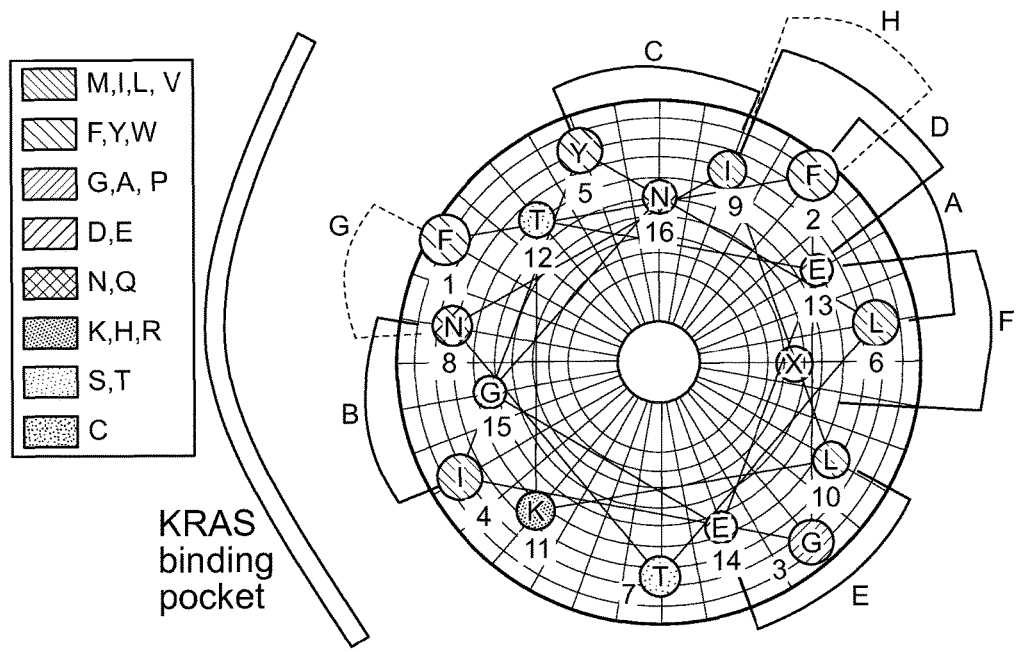

| Staple | Sequence | SAH |
|---|---|---|
|  | 123456789 |  |
| A | FXGIYXTNILKTEEGN | SAH-SOS$_{A1}$ |
|  | RRFXGIYXTNILKTEEGN | SAH-SOS$_{A2}$ |
|  | FXGIYXTNILKTEEGNRR | SAH-SOS$_{A3}$ |
| B | RRFFGXYLTXILKTEEGN | SAH-SOS$_{B2}$ |
| C | FFGIXLTNXLKTEEGN | SAH-SOS$_{C1}$ |
|  | RRFFGIXLTNXLKTEEGN | SAH-SOS$_{C2}$ |
|  | FFGIXLTNXLKTEEGNRR | SAH-SOS$_{C3}$ |
| D | FFGIYLTNXLKTXEGN | SAH-SOS$_{D1}$ |
|  | RRFFGIYLTNXLKTXEGN | SAH-SOS$_{D2}$ |
|  | FFGIYLTNXLKTXEGNRR | SAH-SOS$_{D3}$ |
| E | RRFFGIYLTNIXKTEXGN | SAH-SOS$_{E2}$ |
| F | RRFFGIYLTNILKTXEGNX | SAH-SOS$_{F2}$ |
| G | RRXFGIYLTXILKTEEGN | SAH-SOS$_{G2}$ |
| H | RRFXGIYLTNXLKTEEGN | SAH-SOS$_{H2}$ |

FIG. 2B

| N-terminus | Sequence Composition |
|---|---|
| Ac | FXGIYXTNILKTEEGNRR |
| Ac | RRFFGIXLTNXLKTEEGN |
| Ac | FFGIXLTNXLKTEEGNRR |
| Ac | RRFXGIYXTNILKTEEGN |
| Ac | FFGIYLTNXLKTXEGNRR |
| Ac | RRFFGIYLTNXLKTXEGN |
| Ac | RRFFGXYLTXILKTEEGN |
| Ac | RRZFGIYLTXILKTEEGN |
| Ac | RRFFGIYLTNILKTXEGNX |
| Ac | RRFZGIYLTNXLKTEEGN |
| Ac | RRFFGIYLTNIXKTEXGN |
| Ac | RRFFGIXLTNXLKTEEGNPEVL |
| Ac | RRFFGIXLTNXLKTEEGNPEVLR |
| Ac | RRFFGIXLTNXLRTEUGN |
| Ac | RRFFGKXLTNXLRTEEGN |
| Ac | RRFFGIXLTNXCRTEEGN |
| Ac | RRFFGIXLTNXLRTECGN |
| Ac | RRFFGJXLTNXLKTEEGN |
| Ac | RRFFDIXLTNXLKTEEGN |
| Ac | RRFFGIXDTNXLKTEEGN |
| Ac | IWIAFEGIXLTNXLKTYERR |
| Ac | RRFEGIXRLEXLKAEEAN |
| Ac | RRFFGIXKTNXEKTEEGN |
| Ac | RRFFGIXLTRXLKTEEGN |

FIG. 3A

| | |
|---|---|
| Ac | RRFFGIXLTNXLRTEK(G-Gmono)GN |
| Ac | RRFFGIXLTNXLRTEK(Gmono)GN |
| Ac | RRFFGIXLTNXLRTEEGNPK(G-Gmono) |
| Ac | RRFFGIXLTNXLRTEEGNPK(Gmono) |
| Ac | RRFFGIXLTNXK(G-Gmono)RTEEGN |
| Ac | RRFFGIXLTNXK(Gmono)RTEEGN |
| Ac | RRFFG(SEDHY)KXLTNXLRTEEGN |
| FITC-βAla | FXGIYXTNILKTEEGN |
| FITC-βAla | FFGIXLTNXLKTEEGN |
| FITC-βAla | FFGIYLTNXLKTXEGN |
| FITC-βAla | RRFFGXYLTXILKTEEGN |
| FITC-βAla | RRFZGIYLTNXLKTEEGN |
| FITC-βAla | RRFFGIYLTNIXKTEXGN |
| FITC-βAla | RRFFGIXLTNXLKTEEGNPEVL |
| FITC-βAla | RRFFGIXLTNXLRTEUGN |
| FITC-βAla | RRFFGKXLTNXLRTEEGN |
| FITC-βAla | RRFFGJXLTNXLKTEEGN |
| FITC-βAla | RRFFDIXLTNXLKTEEGN |
| FITC-βAla | RRFFGIXDTNXLKTEEGN |
| FITC-βAla | IWIAFEGIXLTNXLKTYERR |
| FITC-βAla | RRFEGIXRLEXLKAEEAN |
| FITC-βAla | RRFFGIXKTNXEKTEEGN |
| FITC-βAla | RRFFGIXLTRXLKTEEGN |
| FITC-βAla | RRFFGIXLTNXLRTEK(G-Gmono)GN |

FIG. 3A (Cont.)

| | |
|---|---|
| Ac | FXGIYXTNILKTEEGN |
| Ac | FFGIXLTNXLKTEEGN |
| Ac | FFGIYLTNXLKTXEGN |
| Ac | FFGIYLTNIXKTEXGN |
| Ac | FFGIXKTNXEKTEEGN |
| Ac | FFGXYLTXILKTEEGN |
| Ac | ZFGIYLTXILKTEEGN |
| Ac | FFGIYLTNILKTXEGNX |
| Ac | FZGIYLTNXLKTEEGN |
| Ac | FFDIXLTNXLKTEEGN |
| Ac | FFGIXDTNXLKTEEGN |
| Ac | FFGIXLTRXLKTEEGN |
| Ac | FFGUXLTNXLKTEEGN |
| Ac | FFGKXLTNXLKTEEGN |
| Ac | FFGIYLTNILKTEEGN |
| Ac | RRFFGIXLTNXLRTEKGN |
| Ac | RRFFGUXLTNXLKTEEGN |
| FITC-βAla | FXGIYXTNILKTEEGNRR |
| FITC-βAla | RRFFGIXLTNXLKTEEGN |
| FITC-βAla | FFGIXLTNXLKTEEGNRR |
| FITC-βAla | RRFXGIYXTNILKTEEGN |
| FITC-βAla | RRFFGIYLTNXLKTXEGN |
| FITC-βAla | FFGIYLTNXLKTXEGNRR |
| FITC-βAla | FFGIYLTNIXKTEXGN |

FIG. 3B

| | |
|---|---|
| FITC-βAla | FFGIXKTNXEKTEEGN |
| FITC-βAla | FFGXYLTXILKTEEGN |
| FITC-βAla | ZFGIYLTXILKTEEGN |
| FITC-βAla | FFGIYLTNILKTXEGNX |
| FITC-βAla | FZGIYLTNXLKTEEGN |
| FITC-βAla | FFDIXLTNXLKTEEGN |
| FITC-βAla | FFGIXDTNXLKTEEGN |
| FITC-βAla | FFGIXLTRXLKTEEGN |
| FITC-βAla | FFGUXLTNXLKTEEGN |
| FITC-βAla | FFGKXLTNXLKTEEGN |
| FITC-βAla | FFGIYLTNILKTEEGN |
| FITC-βAla | RRZFGIYLTXILKTEEGN |
| FITC-βAla | RRFFGIYLTNILKTXEGNX |
| FITC-βAla | RRFFGIXLTNXLKTEEGNPEVLR |
| FITC-βAla | RRFFGIXLTNXLRTEKGN |
| FITC-βAla | RRFFGIXLTNXCRTEEGN |
| FITC-βAla | RRFFGIXLTNXLRTECGN |
| FITC-βAla | RRFFGUXLTNXLKTEEGN |
| FITC-βAla | RRFFGIXLTNXLRTEK(-Gmono)GN |
| FITC-βAla | RRFFGIXLTNXLRTEEGNPK(-G-Gmono) |
| FITC-βAla | RRFFGIXLTNXLRTEEGNPK(-Gmono) |
| FITC-βAla | RRFFGIXLTNXK(-G-Gmono)RTEEGN |
| FITC-βAla | RRFFGIXLTNXK(-Gmono)RTEEGN |
| FITC-βAla | RRFFGK(SEDHY)XLTNXLRTEEGN |

FIG. 3B (Cont.)

| Construct | Sequence | Binding Affinity to KRAS (wt) |
|---|---|---|
| SAH-SOS$_{A1}$ | FXGIYXTNILKTEEGN | 15 nM |
| SAH-SOS$_{A2}$ | RRFXGIYXTNILKTEEGN | 21 nM |
| SAH-SOS$_{A3}$ | FXGIYXTNILKTEEGNRR | 19 nM |
| SAH-SOS$_{B2}$ | RRFFGXYLTXILKTEEGN | >4 μM |
| SAH-SOS$_{C1}$ | FFGIXLTNXLKTEEGN | 20 nM |
| SAH-SOS$_{C2}$ | RRFFGIXLTNXLKTEEGN | 16 nM |
| SAH-SOS$_{C3}$ | FFGIXLTNXLKTEEGNRR | 28 nM |
| SAH-SOS$_{D1}$ | FFGIYLTNXLKTXEGN | 27 nM |
| SAH-SOS$_{E2}$ | RRFFGIYLTNIXKTEXGN | 24 nM |
| SAH-SOS$_{H2}$ | RRFZGIYLTNXLKTEEGN | 29 nM |

FIG. 5

| EC$_{50}$, nM | WT | G12D | G12V | G12C | G12S | Q12H |
|---|---|---|---|---|---|---|
| SAH-SOS1$_{C1}$ | 117 ± 13 | 136 ± 15 | 135 ± 15 | 108 ± 16 | 118 ± 13 | 125 ± 19 |
| SAH-SOS1$_{D1}$ | 79 ± 25 | 61 ± 30 | 103 ± 15 | 129 ± 18 | 140 ± 24 | 124 ± 24 |
| SAH-SOS1$_{A1}$ | 80 ± 25 | 82 ± 14 | 143 ± 25 | 133 ± 26 | 132 ± 16 | 158 ± 30 |
| SAH-SOS1$_{B1}$ | >4000 | >4000 | >4000 | >4000 | >4000 | >4000 |

FIG. 6B

| EC$_{50}$, nM | WT | G12D | G12V | G12C | G12S | Q12H |
|---|---|---|---|---|---|---|
| SAH-SOS1$_{C2}$ | 117 ± 13 | 136 ± 15 | 135 ± 15 | 108 ± 16 | 118 ± 13 | 125 ± 19 |
| SAH-SOS1$_{B2}$ | >4000 | >4000 | >4000 | >4000 | >4000 | >4000 |

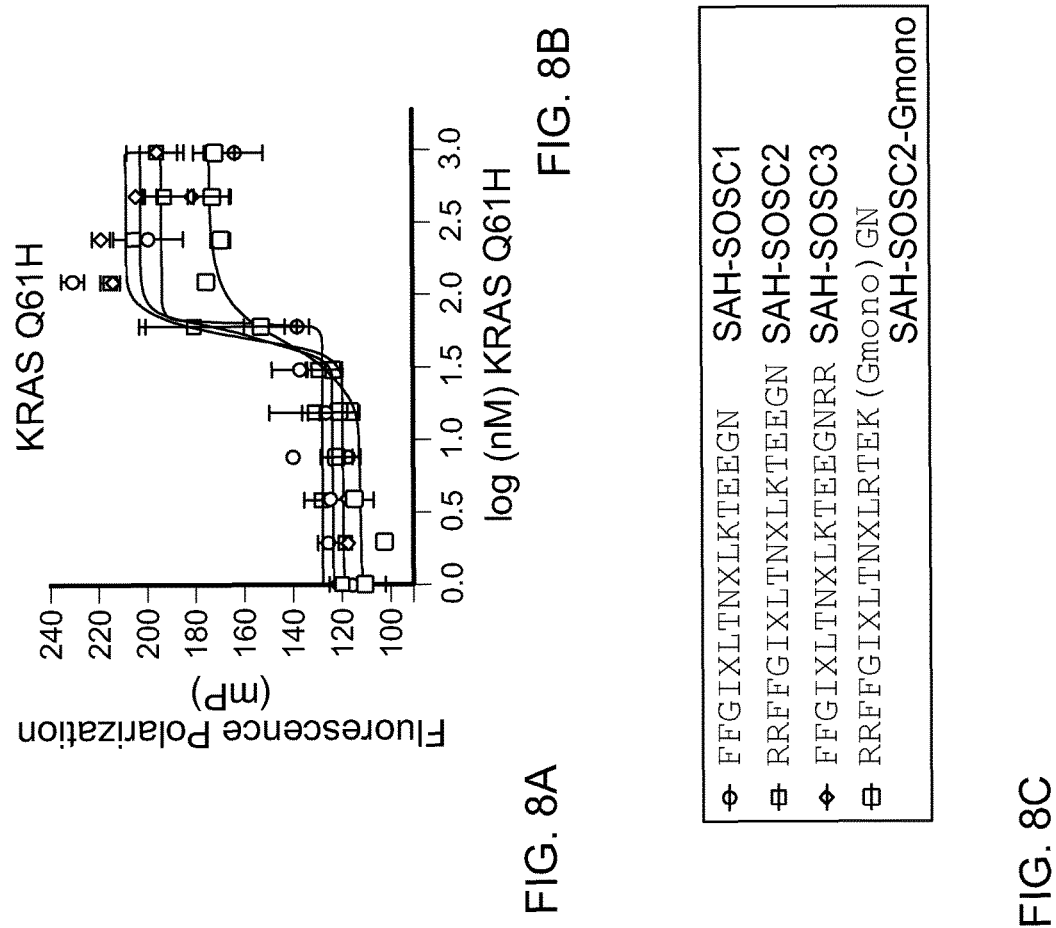
FIG. 8A
FIG. 8B
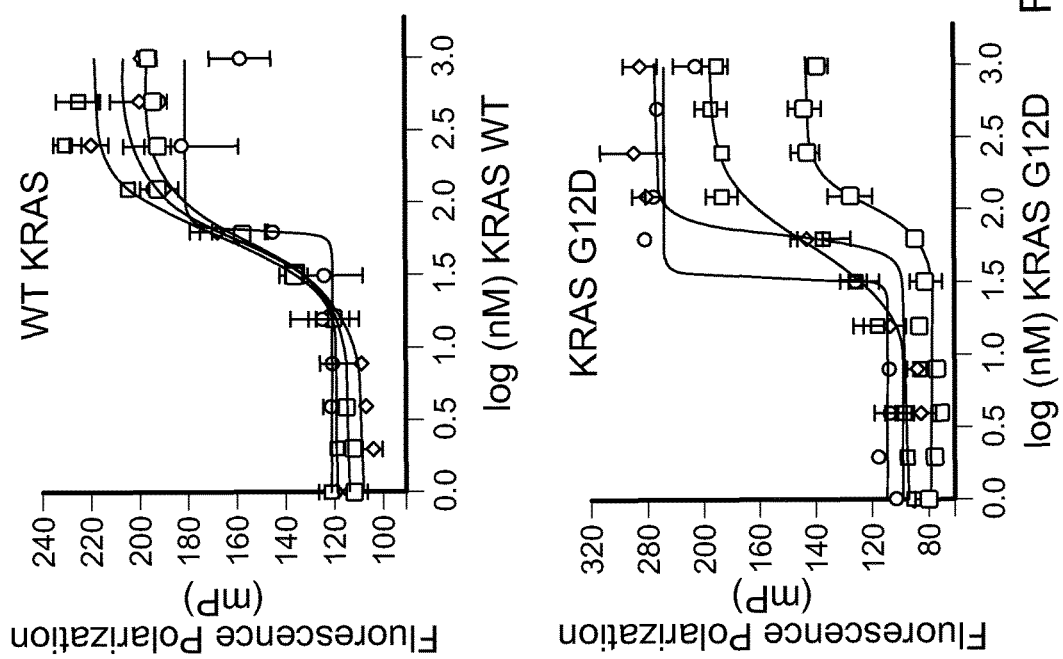
FIG. 8C

| | |
|---|---|
| ◇ FFGIXLTNXLKTEEGN | SAH-SOSC1 |
| ⊞ RRFFGIXLTNXLKTEEGN | SAH-SOSC2 |
| ◆ FFGIXLTNXLKTEEGNRR | SAH-SOSC3 |
| ⊟ RRFFGIXLTNXLRTEK(Gmono)GN | SAH-SOSC2-Gmono |

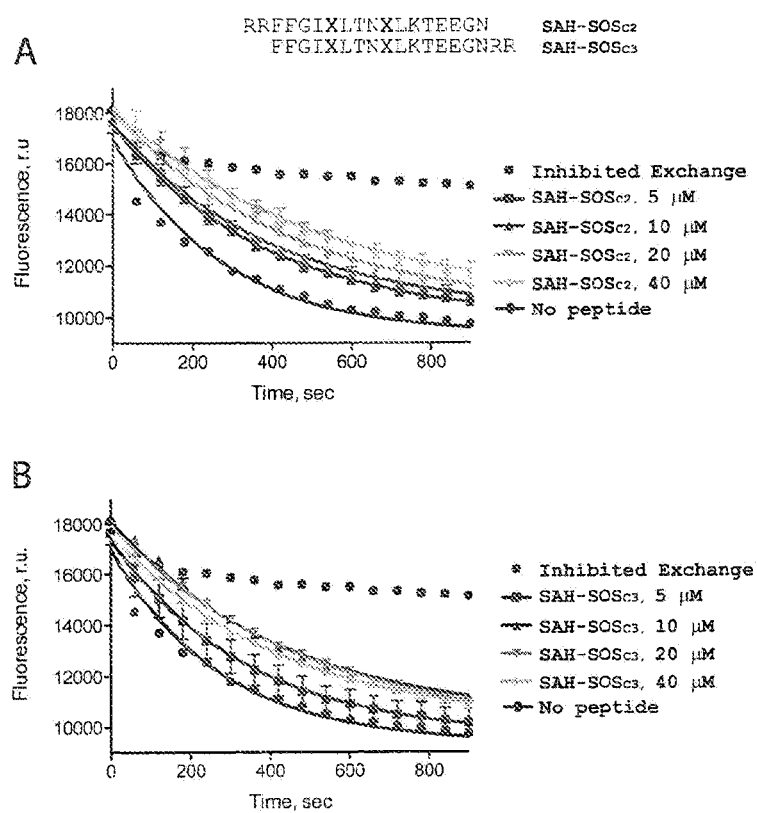
FIGURES 10A-B

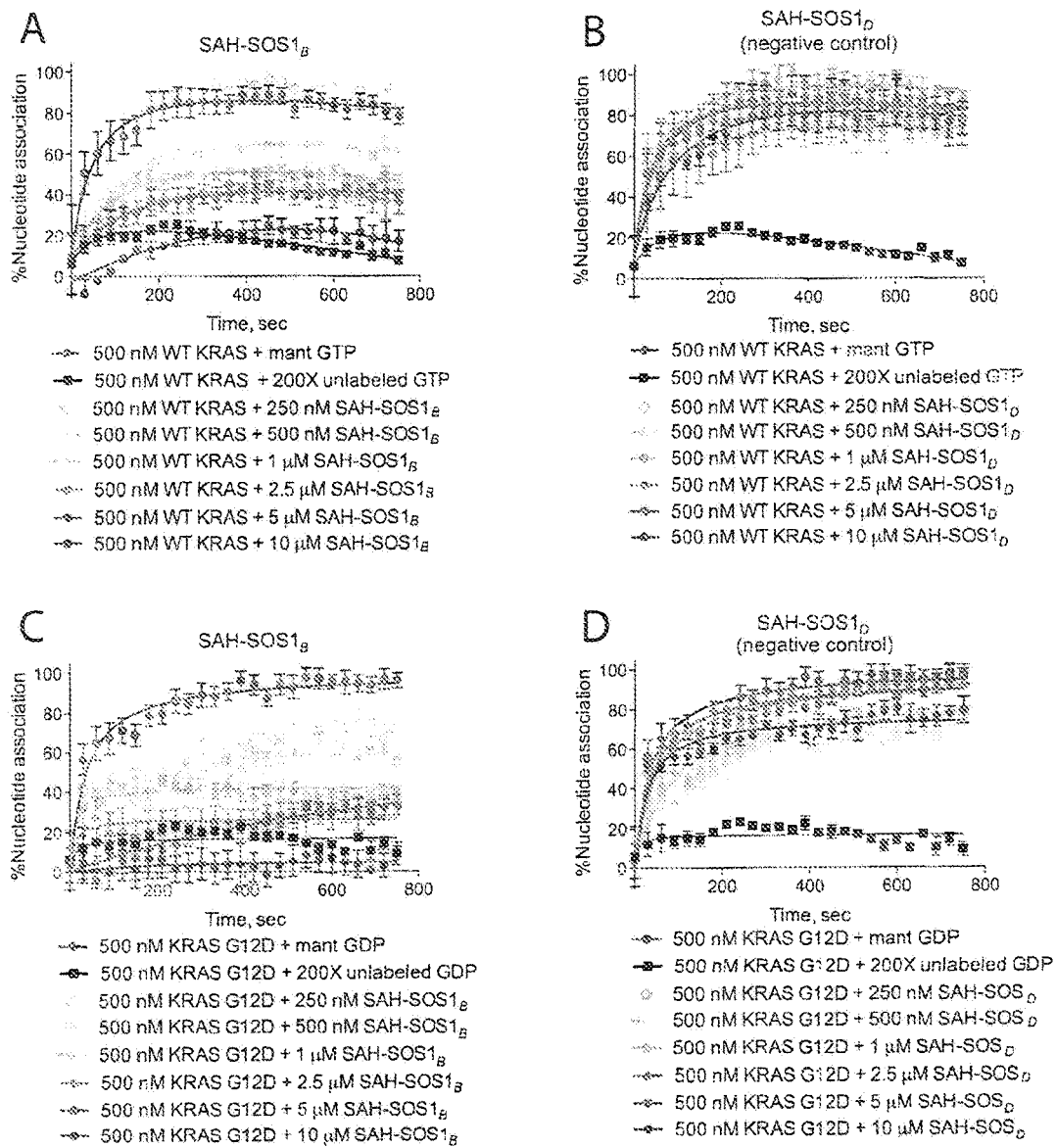
Figures 11A-D

L938K conjugation:
RRFFGIXLTNXKKTEKGN
RRFFGIXLTNXK(Gmono)RTEEGN
RRFFGIXLTNXK(G-Gmono)RTEEGN

K942 conjugation:
RRFFGIXLTNXLKTEKGN
RRFFGIXLTNXLRTEK(Gmono)GN
RRFFGIXLTNXLRTEK(G-Gmono)GN

C-terminal K conjugation:
RRFFGIXLTNXKKTEKGNPK
RRFFGIXLTNXLRTEEGNPK(Gmono)
RRFFGIXLTNXLRTEEGNPK(G-Gmono)

| $A_0$ | $B_0$ | $C_0$ | $D_0$ | $E_0$ | $F_0$ | $G_0$ | $A_1$ | $B_1$ | $C_1$ | $D_1$ | $E_1$ | $F_1$ | $G_1$ | $A_2$ | $B_2$ |
|---|---|---|---|---|---|---|---|---|---|---|---|---|---|---|---|
| F | F | G | I | Y | L | T | N | I | L | K | T | E | E | G | N |
| $i_1$ |  |  | ◊ | ⊙ |  | † |  |  |  |  |  |  |  |  |  |
|  | $i_2$ |  |  | ◊ | ⊙ |  | † |  |  |  |  |  |  |  |  |
|  |  | $i_3$ |  |  | ◊ | ⊙ |  | † |  |  |  |  |  |  |  |
| □ |  |  | $i_4$ |  |  | ◊ | ⊙ |  | † |  |  |  |  |  |  |
| ○ | □ |  |  | $i_5$ |  |  | ◊ | ⊙ |  | † |  |  |  |  |  |
|  | ○ | □ |  |  | $i_6$ |  |  | ◊ | ⊙ |  | † |  |  |  |  |
|  |  | ○ | □ |  |  | $i_7$ |  |  | ◊ | ⊙ |  | † |  |  |  |
| ‡ |  |  | ○ | □ |  |  | $i_8$ |  |  | ◊ | ⊙ |  | † |  |  |
|  | ‡ |  |  | ○ | □ |  |  | $i_9$ |  |  | ◊ | ⊙ |  | † |  |
|  |  | ‡ |  |  | ○ | □ |  |  | $i_{10}$ |  |  | ◊ | ⊙ |  |  |
|  |  |  | ‡ |  |  | ○ | □ |  |  | $i_{11}$ |  |  | ◊ | ⊙ |  |
|  |  |  |  | ‡ |  |  | ○ | □ |  |  | $i_{12}$ |  |  | ◊ | ⊙ |
|  |  |  |  |  | ‡ |  |  | ○ | □ |  |  | $i_{13}$ |  |  | ◊ |
|  |  |  |  |  |  | ‡ |  |  | ○ | □ |  |  | $i_{14}$ |  |  |
|  |  |  |  |  |  |  | ‡ |  |  | ○ | □ |  |  | $i_{15}$ |  |
|  |  |  |  |  |  |  |  | ‡ |  |  | ○ | □ |  |  | $i_{16}$ |
|  |  |  |  |  |  |  |  |  | ‡ |  |  | ○ | □ |  |  |
|  |  |  |  |  |  |  |  |  |  | ‡ |  |  | ○ | □ |  |
|  |  |  |  |  |  |  |  |  |  |  | ‡ |  |  | ○ | □ |
|  |  |  |  |  |  |  |  |  |  |  |  | ‡ |  |  | ○ |
|  |  |  |  |  |  |  |  |  |  |  |  |  | ‡ |  |  |
|  |  |  |  |  |  |  |  |  |  |  |  |  |  | ‡ |  |
|  |  |  |  |  |  |  |  |  |  |  |  |  |  |  | ‡ |

SEQUENCE LISTING

```
<160> NUMBER OF SEQ ID NOS: 136

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Phe or any conservative amino acid substitution
<220> FEATURE:
<221> NAME/KEY: MOD_RES
<222> LOCATION: (3)..(3)
<223> OTHER INFORMATION: Gly or any conservative amino acid substitution
<220> FEATURE:
<221> NAME/KEY: MOD_RES
<222> LOCATION: (4)..(4)
<223> OTHER INFORMATION: Ile or any conservative amino acid substitution
<220> FEATURE:
<221> NAME/KEY: MOD_RES
```

```
<222> LOCATION: (5)..(5)
<223> OTHER INFORMATION: Tyr or any conservative amino acid substitution
<220> FEATURE:
<221> NAME/KEY: MOD_RES
<222> LOCATION: (6)..(6)
<223> OTHER INFORMATION: Leu or any conservative amino acid substitution
<220> FEATURE:
<221> NAME/KEY: MOD_RES
<222> LOCATION: (7)..(7)
<223> OTHER INFORMATION: Thr or any conservative amino acid substitution
<220> FEATURE:
<221> NAME/KEY: MOD_RES
<222> LOCATION: (8)..(8)
<223> OTHER INFORMATION: Asn or any conservative amino acid substitution
<220> FEATURE:
<221> NAME/KEY: MOD_RES
<222> LOCATION: (9)..(9)
<223> OTHER INFORMATION: Ile or any conservative amino acid substitution
<220> FEATURE:
<221> NAME/KEY: MOD_RES
<222> LOCATION: (10)..(10)
<223> OTHER INFORMATION: Leu or any conservative amino acid substitution
<220> FEATURE:
<221> NAME/KEY: MOD_RES
<222> LOCATION: (11)..(11)
<223> OTHER INFORMATION: Lys or any conservative amino acid substitution
<220> FEATURE:
<221> NAME/KEY: MOD_RES
<222> LOCATION: (12)..(12)
<223> OTHER INFORMATION: Thr or any conservative amino acid substitution
<220> FEATURE:
<221> NAME/KEY: MOD_RES
<222> LOCATION: (13)..(14)
<223> OTHER INFORMATION: Glu or any conservative amino acid substitution
<220> FEATURE:
<221> NAME/KEY: MOD_RES
<222> LOCATION: (15)..(15)
<223> OTHER INFORMATION: Gly or any conservative amino acid substitution
<220> FEATURE:
<221> NAME/KEY: MOD_RES
<222> LOCATION: (16)..(16)
<223> OTHER INFORMATION: Asn or any conservative amino acid substitution
<220> FEATURE:
<223> OTHER INFORMATION: See specification as filed for detailed
      description of substitutions and preferred embodiments

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Phe Gly Ile Tyr Leu Thr Asn Ile Leu Lys Thr Glu Glu Gly Asn
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Phe Gly Ile Tyr Leu Thr Asn Ile Leu Lys Thr Glu Glu Gly Asn
1               5                   10                  15
```

Arg Arg

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Phe Phe Gly Ile Tyr Leu Thr Asn Ile Leu Lys Thr Glu Glu
1               5                   10                  15

Gly Asn

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any stapling amino acid

<400> SEQUENCE: 5

Phe Phe Gly Ile Tyr Xaa Thr Asn Ile Leu Lys Thr Glu Glu Gly Asn
1               5                   10                  15

Pro Glu Leu Val Arg Arg
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Phe Phe Gly Ile Tyr Leu Thr Asn Ile Leu Lys Thr Glu Glu
1               5                   10                  15

Gly Asn Pro Glu Leu Val
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Phe Phe Gly Ile Tyr Leu Thr Asn Ile Leu Lys Thr Glu Glu Gly Asn
1               5                   10                  15

Pro Glu Leu Val
            20

<210> SEQ ID NO 8
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 8

Phe Phe Gly Ile Tyr Leu Thr Asn Ile Leu Lys Thr Glu Glu Gly Asn
1               5                   10                  15

Arg

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Phe Phe Gly Ile Tyr Leu Thr Asn Ile Leu Lys Thr Glu Glu Gly
1               5                   10                  15

Asn

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any stapling amino acid

<400> SEQUENCE: 10

Phe Phe Gly Ile Tyr Xaa Thr Asn Ile Leu Lys Thr Glu Glu Gly Asn
1               5                   10                  15

Pro Glu Leu Val Arg
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Phe Phe Gly Ile Tyr Leu Thr Asn Ile Leu Lys Thr Glu Glu Gly
1               5                   10                  15

Asn Pro Glu Leu Val
            20

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any stapling amino acid
<220> FEATURE:
<221> NAME/KEY: MOD_RES
<222> LOCATION: (6)..(6)

<223> OTHER INFORMATION: Any stapling amino acid

<400> SEQUENCE: 12

Phe Xaa Gly Ile Tyr Xaa Thr Asn Ile Leu Lys Thr Glu Glu Gly Asn
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any stapling amino acid
<220> FEATURE:
<221> NAME/KEY: MOD_RES
<222> LOCATION: (8)..(8)
<223> OTHER INFORMATION: Any stapling amino acid

<400> SEQUENCE: 13

Arg Arg Phe Xaa Gly Ile Tyr Xaa Thr Asn Ile Leu Lys Thr Glu Glu
1               5                   10                  15

Gly Asn

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any stapling amino acid
<220> FEATURE:
<221> NAME/KEY: MOD_RES
<222> LOCATION: (6)..(6)
<223> OTHER INFORMATION: Any stapling amino acid

<400> SEQUENCE: 14

Phe Xaa Gly Ile Tyr Xaa Thr Asn Ile Leu Lys Thr Glu Glu Gly Asn
1               5                   10                  15

Arg Arg

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 15

Arg Arg Phe Phe Gly Xaa Tyr Leu Thr Xaa Ile Leu Lys Thr Glu Glu
1               5                   10                  15

Gly Asn

```
<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 16

Phe Phe Gly Ile Xaa Leu Thr Asn Xaa Leu Lys Thr Glu Glu Gly Asn
1               5                   10                  15

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 17

Arg Arg Phe Phe Gly Ile Xaa Leu Thr Asn Xaa Leu Lys Thr Glu Glu
1               5                   10                  15

Gly Asn

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 18

Phe Phe Gly Ile Xaa Leu Thr Asn Xaa Leu Lys Thr Glu Glu Gly Asn
1               5                   10                  15

Arg Arg

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (9)..(9)
<223> OTHER INFORMATION: Any stapling amino acid
<220> FEATURE:
<221> NAME/KEY: MOD_RES
<222> LOCATION: (13)..(13)
<223> OTHER INFORMATION: Any stapling amino acid

<400> SEQUENCE: 19

Phe Phe Gly Ile Tyr Leu Thr Asn Xaa Leu Lys Thr Xaa Glu Gly Asn
1               5                   10                  15

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (15)..(15)
<223> OTHER INFORMATION: Any stapling amino acid

<400> SEQUENCE: 20

Arg Arg Phe Phe Gly Ile Tyr Leu Thr Asn Xaa Leu Lys Thr Xaa Glu
1               5                   10                  15

Gly Asn

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any stapling amino acid
<220> FEATURE:
<221> NAME/KEY: MOD_RES
<222> LOCATION: (13)..(13)
<223> OTHER INFORMATION: Any stapling amino acid

<400> SEQUENCE: 21

Phe Phe Gly Ile Tyr Leu Thr Asn Xaa Leu Lys Thr Xaa Glu Gly Asn
1               5                   10                  15

Arg Arg

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (16)..(16)
<223> OTHER INFORMATION: Any stapling amino acid

<400> SEQUENCE: 22
```

Arg Arg Phe Phe Gly Ile Tyr Leu Thr Asn Ile Xaa Lys Thr Glu Xaa
1               5                   10                  15

Gly Asn

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any stapling amino acid
<220> FEATURE:
<221> NAME/KEY: MOD_RES
<222> LOCATION: (19)..(19)
<223> OTHER INFORMATION: Any stapling amino acid

<400> SEQUENCE: 23

Arg Arg Phe Phe Gly Ile Tyr Leu Thr Asn Ile Leu Lys Thr Xaa Glu
1               5                   10                  15

Gly Asn Xaa

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 24

Arg Arg Xaa Phe Gly Ile Tyr Leu Thr Xaa Ile Leu Lys Thr Glu Glu
1               5                   10                  15

Gly Asn

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 25

Arg Arg Phe Xaa Gly Ile Tyr Leu Thr Asn Xaa Leu Lys Thr Glu Glu
1               5                   10                  15

Gly Asn

```
<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (2)..(2)
<223> OTHER INFORMATION: Any stapling amino acid
<220> FEATURE:
<221> NAME/KEY: MOD_RES
<222> LOCATION: (6)..(6)
<223> OTHER INFORMATION: Any stapling amino acid

<400> SEQUENCE: 26

Phe Xaa Gly Ile Tyr Xaa Thr Asn Ile Leu Lys Thr Glu Glu Gly Asn
1               5                   10                  15

Arg Arg

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 27

Arg Arg Phe Phe Gly Ile Xaa Leu Thr Asn Xaa Leu Lys Thr Glu Glu
1               5                   10                  15

Gly Asn

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 28

Phe Phe Gly Ile Xaa Leu Thr Asn Xaa Leu Lys Thr Glu Glu Gly Asn
1               5                   10                  15

Arg Arg

<210> SEQ ID NO 29
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (4)..(4)
<223> OTHER INFORMATION: Any stapling amino acid
<220> FEATURE:
<221> NAME/KEY: MOD_RES
<222> LOCATION: (8)..(8)
<223> OTHER INFORMATION: Any stapling amino acid

<400> SEQUENCE: 29

Arg Arg Phe Xaa Gly Ile Tyr Xaa Thr Asn Ile Leu Lys Thr Glu Glu
1               5                   10                  15

Gly Asn

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any stapling amino acid
<220> FEATURE:
<221> NAME/KEY: MOD_RES
<222> LOCATION: (13)..(13)
<223> OTHER INFORMATION: Any stapling amino acid

<400> SEQUENCE: 30

Phe Phe Gly Ile Tyr Leu Thr Asn Xaa Leu Lys Thr Xaa Glu Gly Asn
1               5                   10                  15

Arg Arg

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (15)..(15)
<223> OTHER INFORMATION: Any stapling amino acid

<400> SEQUENCE: 31

Arg Arg Phe Phe Gly Ile Tyr Leu Thr Asn Xaa Leu Lys Thr Xaa Glu
1               5                   10                  15

Gly Asn

<210> SEQ ID NO 32
<211> LENGTH: 18
```

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 32

Arg Arg Phe Phe Gly Xaa Tyr Leu Thr Xaa Ile Leu Lys Thr Glu Glu
1               5                   10                  15

Gly Asn

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (3)..(3)
<223> OTHER INFORMATION: (R)-2-amino-2-methyl-dec-9-enoic acid
<220> FEATURE:
<221> NAME/KEY: MOD_RES
<222> LOCATION: (10)..(10)
<223> OTHER INFORMATION: Any stapling amino acid

<400> SEQUENCE: 33

Arg Arg Xaa Phe Gly Ile Tyr Leu Thr Xaa Ile Leu Lys Thr Glu Glu
1               5                   10                  15

Gly Asn

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (15)..(15)
<223> OTHER INFORMATION: Any stapling amino acid
<220> FEATURE:
<221> NAME/KEY: MOD_RES
<222> LOCATION: (19)..(19)
<223> OTHER INFORMATION: Any stapling amino acid

<400> SEQUENCE: 34

Arg Arg Phe Phe Gly Ile Tyr Leu Thr Asn Ile Leu Lys Thr Xaa Glu
1               5                   10                  15

Gly Asn Xaa

<210> SEQ ID NO 35
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (4)..(4)
<223> OTHER INFORMATION: (R)-2-amino-2-methyl-dec-9-enoic acid
<220> FEATURE:
<221> NAME/KEY: MOD_RES
<222> LOCATION: (11)..(11)
<223> OTHER INFORMATION: Any stapling amino acid

<400> SEQUENCE: 35

Arg Arg Phe Xaa Gly Ile Tyr Leu Thr Asn Xaa Leu Lys Thr Glu Glu
 1               5                  10                  15

Gly Asn

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (16)..(16)
<223> OTHER INFORMATION: Any stapling amino acid

<400> SEQUENCE: 36

Arg Arg Phe Phe Gly Ile Tyr Leu Thr Asn Ile Xaa Lys Thr Glu Xaa
 1               5                  10                  15

Gly Asn

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 37

Arg Arg Phe Phe Gly Ile Xaa Leu Thr Asn Xaa Leu Lys Thr Glu Glu
 1               5                  10                  15

Gly Asn Pro Glu Val Leu
            20

<210> SEQ ID NO 38
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 38

Arg Arg Phe Phe Gly Ile Xaa Leu Thr Asn Xaa Leu Lys Thr Glu Glu
1               5                   10                  15

Gly Asn Pro Glu Val Leu Arg
            20

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (16)..(16)
<223> OTHER INFORMATION: L-p-benzoyphenylalanine

<400> SEQUENCE: 39

Arg Arg Phe Phe Gly Ile Xaa Leu Thr Asn Xaa Leu Arg Thr Glu Xaa
1               5                   10                  15

Gly Asn

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 40

Arg Arg Phe Phe Gly Lys Xaa Leu Thr Asn Xaa Leu Arg Thr Glu Glu
1               5                   10                  15

Gly Asn
```

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 41

Arg Arg Phe Phe Gly Ile Xaa Leu Thr Asn Xaa Cys Arg Thr Glu Glu
1               5                   10                  15

Gly Asn

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 42

Arg Arg Phe Phe Gly Ile Xaa Leu Thr Asn Xaa Leu Arg Thr Glu Cys
1               5                   10                  15

Gly Asn

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (6)..(6)
<223> OTHER INFORMATION: (ivDde)Lys
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 43

Arg Arg Phe Phe Gly Xaa Xaa Leu Thr Asn Xaa Leu Lys Thr Glu Glu
1               5                   10                  15

Gly Asn

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 44

Arg Arg Phe Phe Asp Ile Xaa Leu Thr Asn Xaa Leu Lys Thr Glu Glu
1               5                   10                  15

Gly Asn

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 45

Arg Arg Phe Phe Gly Ile Xaa Asp Thr Asn Xaa Leu Lys Thr Glu Glu
1               5                   10                  15

Gly Asn

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any stapling amino acid
<220> FEATURE:
<221> NAME/KEY: MOD_RES
<222> LOCATION: (13)..(13)
<223> OTHER INFORMATION: Any stapling amino acid

<400> SEQUENCE: 46

Ile Trp Ile Ala Phe Glu Gly Ile Xaa Leu Thr Asn Xaa Leu Lys Thr
1               5                   10                  15

Tyr Glu Arg Arg
            20

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 47

Arg Arg Phe Glu Gly Ile Xaa Arg Leu Glu Xaa Leu Lys Ala Glu Glu
1               5                   10                  15

Ala Asn

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 48

Arg Arg Phe Phe Gly Ile Xaa Lys Thr Asn Xaa Glu Lys Thr Glu Glu
1               5                   10                  15

Gly Asn

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 49

Arg Arg Phe Phe Gly Ile Xaa Leu Thr Arg Xaa Leu Lys Thr Glu Glu
1               5                   10                  15

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (16)..(16)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 50

Arg Arg Phe Phe Gly Ile Xaa Leu Thr Asn Xaa Leu Arg Thr Glu Lys
1               5                   10                  15

Gly Asn

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (16)..(16)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 51

Arg Arg Phe Phe Gly Ile Xaa Leu Thr Asn Xaa Leu Arg Thr Glu Lys
1               5                   10                  15

Gly Asn

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:

```
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (20)..(20)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 52

Arg Arg Phe Phe Gly Ile Xaa Leu Thr Asn Xaa Leu Arg Thr Glu Glu
1               5                   10                  15

Gly Asn Pro Lys
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (20)..(20)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 53

Arg Arg Phe Phe Gly Ile Xaa Leu Thr Asn Xaa Leu Arg Thr Glu Glu
1               5                   10                  15

Gly Asn Pro Lys
            20

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (12)..(12)
<223> OTHER INFORMATION: Lys modified with a unique side chain
```

```
<220> FEATURE:
<223> OTHER INFORMATION: See specification as filed for detailed
      description of substitutions and preferred embodiments

<400> SEQUENCE: 54

Arg Arg Phe Phe Gly Ile Xaa Leu Thr Asn Xaa Lys Arg Thr Glu Glu
1               5                   10                  15

Gly Asn

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (12)..(12)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 55

Arg Arg Phe Phe Gly Ile Xaa Leu Thr Asn Xaa Lys Arg Thr Glu Glu
1               5                   10                  15

Gly Asn

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: Gly modified with a unique side chain
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<223> OTHER INFORMATION: See specification as filed for detailed
      description of substitutions and preferred embodiments

<400> SEQUENCE: 56

Arg Arg Phe Phe Gly Lys Xaa Leu Thr Asn Xaa Leu Arg Thr Glu Glu
1               5                   10                  15

Gly Asn

<210> SEQ ID NO 57
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (3)..(3)
<223> OTHER INFORMATION: Any stapling amino acid
<220> FEATURE:
<221> NAME/KEY: MOD_RES
<222> LOCATION: (7)..(7)
<223> OTHER INFORMATION: Any stapling amino acid

<400> SEQUENCE: 57

Xaa Phe Xaa Gly Ile Tyr Xaa Thr Asn Ile Leu Lys Thr Glu Glu Gly
1               5                   10                  15

Asn

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 58

Xaa Phe Phe Gly Ile Xaa Leu Thr Asn Xaa Leu Lys Thr Glu Glu Gly
1               5                   10                  15

Asn

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (14)..(14)
<223> OTHER INFORMATION: Any stapling amino acid

<400> SEQUENCE: 59

Xaa Phe Phe Gly Ile Tyr Leu Thr Asn Xaa Leu Lys Thr Xaa Glu Gly
1               5                   10                  15
```

Asn

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 60

Xaa Arg Arg Phe Phe Gly Xaa Tyr Leu Thr Xaa Ile Leu Lys Thr Glu
1               5                   10                  15

Glu Gly Asn

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (5)..(5)
<223> OTHER INFORMATION: (R)-2-amino-2-methyl-dec-9-enoic acid
<220> FEATURE:
<221> NAME/KEY: MOD_RES
<222> LOCATION: (12)..(12)
<223> OTHER INFORMATION: Any stapling amino acid

<400> SEQUENCE: 61

Xaa Arg Arg Phe Xaa Gly Ile Tyr Leu Thr Asn Xaa Leu Lys Thr Glu
1               5                   10                  15

Glu Gly Asn

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid -continued

```
<400> SEQUENCE: 62

Xaa Arg Arg Phe Phe Gly Ile Tyr Leu Thr Asn Ile Xaa Lys Thr Glu
1               5                   10                  15

Xaa Gly Asn

<210> SEQ ID NO 63
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 63

Xaa Arg Arg Phe Phe Gly Ile Xaa Leu Thr Asn Xaa Leu Lys Thr Glu
1               5                   10                  15

Glu Gly Asn Pro Glu Val Leu
            20

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (17)..(17)
<223> OTHER INFORMATION: L-p-benzoyphenylalanine

<400> SEQUENCE: 64

Xaa Arg Arg Phe Phe Gly Ile Xaa Leu Thr Asn Xaa Leu Arg Thr Glu
1               5                   10                  15

Xaa Gly Asn

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 65

Xaa Arg Arg Phe Phe Gly Lys Xaa Leu Thr Asn Xaa Leu Arg Thr Glu
1               5                  10                  15

Glu Gly Asn

<210> SEQ ID NO 66
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (7)..(7)
<223> OTHER INFORMATION: (ivDde)Lys
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 66

Xaa Arg Arg Phe Phe Gly Xaa Xaa Leu Thr Asn Xaa Leu Lys Thr Glu
1               5                  10                  15

Glu Gly Asn

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 67

Xaa Arg Arg Phe Phe Asp Ile Xaa Leu Thr Asn Xaa Leu Lys Thr Glu
1               5                  10                  15

Glu Gly Asn
```

```
<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 68

Xaa Arg Arg Phe Phe Gly Ile Xaa Asp Thr Asn Xaa Leu Lys Thr Glu
1               5                   10                  15

Glu Gly Asn

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (14)..(14)
<223> OTHER INFORMATION: Any stapling amino acid

<400> SEQUENCE: 69

Xaa Ile Trp Ile Ala Phe Glu Gly Ile Xaa Leu Thr Asn Xaa Leu Lys
1               5                   10                  15

Thr Tyr Glu Arg Arg
            20

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 70
```

```
Xaa Arg Arg Phe Glu Gly Ile Xaa Arg Leu Glu Xaa Leu Lys Ala Glu
1               5                   10                  15

Glu Ala Asn

<210> SEQ ID NO 71
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 71

Xaa Arg Arg Phe Phe Gly Ile Xaa Lys Thr Asn Xaa Glu Lys Thr Glu
1               5                   10                  15

Glu Gly Asn

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 72

Xaa Arg Arg Phe Phe Gly Ile Xaa Leu Thr Arg Xaa Leu Lys Thr Glu
1               5                   10                  15

Glu Gly Asn

<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
```

<222> LOCATION: (12)..(12)
<223> OTHER INFORMATION: Any stapling amino acid
<220> FEATURE:
<221> NAME/KEY: MOD_RES
<222> LOCATION: (17)..(17)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 73

Xaa Arg Arg Phe Phe Gly Ile Xaa Leu Thr Asn Xaa Leu Arg Thr Glu
1               5                   10                  15

Lys Gly Asn

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (2)..(2)
<223> OTHER INFORMATION: Any stapling amino acid
<220> FEATURE:
<221> NAME/KEY: MOD_RES
<222> LOCATION: (6)..(6)
<223> OTHER INFORMATION: Any stapling amino acid

<400> SEQUENCE: 74

Phe Xaa Gly Ile Tyr Xaa Thr Asn Ile Leu Lys Thr Glu Glu Gly Asn
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 75

Phe Phe Gly Ile Xaa Leu Thr Asn Xaa Leu Lys Thr Glu Glu Gly Asn
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any stapling amino acid

```
<220> FEATURE:
<221> NAME/KEY: MOD_RES
<222> LOCATION: (13)..(13)
<223> OTHER INFORMATION: Any stapling amino acid

<400> SEQUENCE: 76

Phe Phe Gly Ile Tyr Leu Thr Asn Xaa Leu Lys Thr Xaa Glu Gly Asn
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (14)..(14)
<223> OTHER INFORMATION: Any stapling amino acid

<400> SEQUENCE: 77

Phe Phe Gly Ile Tyr Leu Thr Asn Ile Xaa Lys Thr Glu Xaa Gly Asn
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 78

Phe Phe Gly Ile Xaa Lys Thr Asn Xaa Glu Lys Thr Glu Glu Gly Asn
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (4)..(4)
<223> OTHER INFORMATION: Any stapling amino acid
<220> FEATURE:
<221> NAME/KEY: MOD_RES
<222> LOCATION: (8)..(8)
<223> OTHER INFORMATION: Any stapling amino acid

<400> SEQUENCE: 79
```

```
Phe Phe Gly Xaa Tyr Leu Thr Xaa Ile Leu Lys Thr Glu Glu Gly Asn
1               5                   10                  15
```

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: (R)-2-amino-2-methyl-dec-9-enoic acid
<220> FEATURE:
<221> NAME/KEY: MOD_RES
<222> LOCATION: (8)..(8)
<223> OTHER INFORMATION: Any stapling amino acid

<400> SEQUENCE: 80

```
Xaa Phe Gly Ile Tyr Leu Thr Xaa Ile Leu Lys Thr Glu Glu Gly Asn
1               5                   10                  15
```

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (13)..(13)
<223> OTHER INFORMATION: Any stapling amino acid
<220> FEATURE:
<221> NAME/KEY: MOD_RES
<222> LOCATION: (17)..(17)
<223> OTHER INFORMATION: Any stapling amino acid

<400> SEQUENCE: 81

```
Phe Phe Gly Ile Tyr Leu Thr Asn Ile Leu Lys Thr Xaa Glu Gly Asn
1               5                   10                  15

Xaa
```

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (2)..(2)
<223> OTHER INFORMATION: (R)-2-amino-2-methyl-dec-9-enoic acid
<220> FEATURE:
<221> NAME/KEY: MOD_RES
<222> LOCATION: (9)..(9)
<223> OTHER INFORMATION: Any stapling amino acid

<400> SEQUENCE: 82

```
Phe Xaa Gly Ile Tyr Leu Thr Asn Xaa Leu Lys Thr Glu Glu Gly Asn
1               5                   10                  15
```

<210> SEQ ID NO 83

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 83

Phe Phe Asp Ile Xaa Leu Thr Asn Xaa Leu Lys Thr Glu Glu Gly Asn
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 84

Phe Phe Gly Ile Xaa Asp Thr Asn Xaa Leu Lys Thr Glu Glu Gly Asn
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 85

Phe Phe Gly Ile Xaa Leu Thr Arg Xaa Leu Lys Thr Glu Glu Gly Asn
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term acetylated
<220> FEATURE:
<221> NAME/KEY: MOD_RES
<222> LOCATION: (4)..(4)
<223> OTHER INFORMATION: L-p-benzoyphenylalanine
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 86

Phe Phe Gly Xaa Xaa Leu Thr Asn Xaa Leu Lys Thr Glu Glu Gly Asn
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 87

Phe Phe Gly Lys Xaa Leu Thr Asn Xaa Leu Lys Thr Glu Glu Gly Asn
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 88

Phe Phe Gly Ile Tyr Leu Thr Asn Ile Leu Lys Thr Glu Glu Gly Asn
1               5                   10                  15

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 89
```

Arg Arg Phe Phe Gly Ile Xaa Leu Thr Asn Xaa Leu Arg Thr Glu Lys
1               5                   10                  15

Gly Asn

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (6)..(6)
<223> OTHER INFORMATION: L-p-benzoyphenylalanine
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 90

Arg Arg Phe Phe Gly Xaa Xaa Leu Thr Asn Xaa Leu Lys Thr Glu Glu
1               5                   10                  15

Gly Asn

<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (3)..(3)
<223> OTHER INFORMATION: Any stapling amino acid
<220> FEATURE:
<221> NAME/KEY: MOD_RES
<222> LOCATION: (7)..(7)
<223> OTHER INFORMATION: Any stapling amino acid

<400> SEQUENCE: 91

Xaa Phe Xaa Gly Ile Tyr Xaa Thr Asn Ile Leu Lys Thr Glu Glu Gly
1               5                   10                  15

Asn Arg Arg

<210> SEQ ID NO 92
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)

<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 92

Xaa Arg Arg Phe Phe Gly Ile Xaa Leu Thr Asn Xaa Leu Lys Thr Glu
1               5                   10                  15

Glu Gly Asn

<210> SEQ ID NO 93
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 93

Xaa Phe Phe Gly Ile Xaa Leu Thr Asn Xaa Leu Lys Thr Glu Glu Gly
1               5                   10                  15

Asn Arg Arg

<210> SEQ ID NO 94
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 94

Xaa Arg Arg Phe Xaa Gly Ile Tyr Xaa Thr Asn Ile Leu Lys Thr Glu
1               5                   10                  15

Glu Gly Asn

<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: FITC-beta Ala
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (16)..(16)
<223> OTHER INFORMATION: Any stapling amino acid

<400> SEQUENCE: 95

Xaa Arg Arg Phe Phe Gly Ile Tyr Leu Thr Asn Xaa Leu Lys Thr Xaa
1               5                   10                  15

Glu Gly Asn

<210> SEQ ID NO 96
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (10)..(10)
<223> OTHER INFORMATION: Any stapling amino acid
<220> FEATURE:
<221> NAME/KEY: MOD_RES
<222> LOCATION: (14)..(14)
<223> OTHER INFORMATION: Any stapling amino acid

<400> SEQUENCE: 96

Xaa Phe Phe Gly Ile Tyr Leu Thr Asn Xaa Leu Lys Thr Xaa Glu Gly
1               5                   10                  15

Asn Arg Arg

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (15)..(15)
<223> OTHER INFORMATION: Any stapling amino acid

<400> SEQUENCE: 97

Xaa Phe Phe Gly Ile Tyr Leu Thr Asn Ile Xaa Lys Thr Glu Xaa Gly
1               5                   10                  15

Asn

<210> SEQ ID NO 98
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 98

Xaa Phe Phe Gly Ile Xaa Lys Thr Asn Xaa Glu Lys Thr Glu Glu Gly
1               5                   10                  15

Asn

<210> SEQ ID NO 99
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (5)..(5)
<223> OTHER INFORMATION: Any stapling amino acid
<220> FEATURE:
<221> NAME/KEY: MOD_RES
<222> LOCATION: (9)..(9)
<223> OTHER INFORMATION: Any stapling amino acid

<400> SEQUENCE: 99

Xaa Phe Phe Gly Xaa Tyr Leu Thr Xaa Ile Leu Lys Thr Glu Glu Gly
1               5                   10                  15

Asn

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (2)..(2)
<223> OTHER INFORMATION: (R)-2-amino-2-methyl-dec-9-enoic acid
<220> FEATURE:
<221> NAME/KEY: MOD_RES
<222> LOCATION: (9)..(9)
<223> OTHER INFORMATION: Any stapling amino acid

<400> SEQUENCE: 100

Xaa Xaa Phe Gly Ile Tyr Leu Thr Xaa Ile Leu Lys Thr Glu Glu Gly
1               5                   10                  15

Asn
```

```
<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (14)..(14)
<223> OTHER INFORMATION: Any stapling amino acid
<220> FEATURE:
<221> NAME/KEY: MOD_RES
<222> LOCATION: (18)..(18)
<223> OTHER INFORMATION: Any stapling amino acid

<400> SEQUENCE: 101

Xaa Phe Phe Gly Ile Tyr Leu Thr Asn Ile Leu Lys Thr Xaa Glu Gly
 1               5                  10                  15

Asn Xaa

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (3)..(3)
<223> OTHER INFORMATION: (R)-2-amino-2-methyl-dec-9-enoic acid
<220> FEATURE:
<221> NAME/KEY: MOD_RES
<222> LOCATION: (10)..(10)
<223> OTHER INFORMATION: Any stapling amino acid

<400> SEQUENCE: 102

Xaa Phe Xaa Gly Ile Tyr Leu Thr Asn Xaa Leu Lys Thr Glu Glu Gly
 1               5                  10                  15

Asn

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 103
```

```
Xaa Phe Phe Asp Ile Xaa Leu Thr Asn Xaa Leu Lys Thr Glu Glu Gly
1               5                   10                  15

Asn

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 104

Xaa Phe Phe Gly Ile Xaa Asp Thr Asn Xaa Leu Lys Thr Glu Glu Gly
1               5                   10                  15

Asn

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 105

Xaa Phe Phe Gly Ile Xaa Leu Thr Arg Xaa Leu Lys Thr Glu Glu Gly
1               5                   10                  15

Asn

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (5)..(5)
<223> OTHER INFORMATION: L-p-benzoyphenylalanine
<220> FEATURE:
<221> NAME/KEY: MOD_RES
```

```
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 106

Xaa Phe Phe Gly Xaa Xaa Leu Thr Asn Xaa Leu Lys Thr Glu Glu Gly
1               5                   10                  15

Asn

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (6)..(6)
<223> OTHER INFORMATION: Any stapling amino acid
<220> FEATURE:
<221> NAME/KEY: MOD_RES
<222> LOCATION: (10)..(10)
<223> OTHER INFORMATION: Any stapling amino acid

<400> SEQUENCE: 107

Xaa Phe Phe Gly Lys Xaa Leu Thr Asn Xaa Leu Lys Thr Glu Glu Gly
1               5                   10                  15

Asn

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala

<400> SEQUENCE: 108

Xaa Phe Phe Gly Ile Tyr Leu Thr Asn Ile Leu Lys Thr Glu Glu Gly
1               5                   10                  15

Asn

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (4)..(4)
<223> OTHER INFORMATION: (R)-2-amino-2-methyl-dec-9-enoic acid
<220> FEATURE:
```

```
<221> NAME/KEY: MOD_RES
<222> LOCATION: (11)..(11)
<223> OTHER INFORMATION: Any stapling amino acid

<400> SEQUENCE: 109

Xaa Arg Arg Xaa Phe Gly Ile Tyr Leu Thr Xaa Ile Leu Lys Thr Glu
1               5                   10                  15

Glu Gly Asn

<210> SEQ ID NO 110
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (16)..(16)
<223> OTHER INFORMATION: Any stapling amino acid
<220> FEATURE:
<221> NAME/KEY: MOD_RES
<222> LOCATION: (20)..(20)
<223> OTHER INFORMATION: Any stapling amino acid

<400> SEQUENCE: 110

Xaa Arg Arg Phe Phe Gly Ile Tyr Leu Thr Asn Ile Leu Lys Thr Xaa
1               5                   10                  15

Glu Gly Asn Xaa
            20

<210> SEQ ID NO 111
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 111

Xaa Arg Arg Phe Phe Gly Ile Xaa Leu Thr Asn Xaa Leu Lys Thr Glu
1               5                   10                  15

Glu Gly Asn Pro Glu Val Leu Arg
            20

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 112

Xaa Arg Arg Phe Phe Gly Ile Xaa Leu Thr Asn Xaa Leu Arg Thr Glu
1               5                   10                  15

Lys Gly Asn

<210> SEQ ID NO 113
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 113

Xaa Arg Arg Phe Phe Gly Ile Xaa Leu Thr Asn Xaa Cys Arg Thr Glu
1               5                   10                  15

Glu Gly Asn

<210> SEQ ID NO 114
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 114

Xaa Arg Arg Phe Phe Gly Ile Xaa Leu Thr Asn Xaa Leu Arg Thr Glu
1               5                   10                  15

Cys Gly Asn

<210> SEQ ID NO 115
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (7)..(7)
<223> OTHER INFORMATION: L-p-benzoyphenylalanine
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid

<400> SEQUENCE: 115

Xaa Arg Arg Phe Phe Gly Xaa Xaa Leu Thr Asn Xaa Leu Lys Thr Glu
1               5                   10                  15

Glu Gly Asn

<210> SEQ ID NO 116
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (17)..(17)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 116

Xaa Arg Arg Phe Phe Gly Ile Xaa Leu Thr Asn Xaa Leu Arg Thr Glu
1               5                   10                  15

Lys Gly Asn

<210> SEQ ID NO 117
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
```

<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (21)..(21)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 117

Xaa Arg Arg Phe Phe Gly Ile Xaa Leu Thr Asn Xaa Leu Arg Thr Glu
1               5                   10                  15

Glu Gly Asn Pro Lys
            20

<210> SEQ ID NO 118
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (21)..(21)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 118

Xaa Arg Arg Phe Phe Gly Ile Xaa Leu Thr Asn Xaa Leu Arg Thr Glu
1               5                   10                  15

Glu Gly Asn Pro Lys
            20

<210> SEQ ID NO 119
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (13)..(13)
<223> OTHER INFORMATION: Lys modified with a unique side chain

```
-continued

<220> FEATURE:
<223> OTHER INFORMATION: See specification as filed for detailed
      description of substitutions and preferred embodiments

<400> SEQUENCE: 119

Xaa Arg Arg Phe Phe Gly Ile Xaa Leu Thr Asn Xaa Lys Arg Thr Glu
1               5                   10                  15

Glu Gly Asn

<210> SEQ ID NO 120
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid
<220> FEATURE:
<221> NAME/KEY: MOD_RES
<222> LOCATION: (13)..(13)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 120

Xaa Arg Arg Phe Phe Gly Ile Xaa Leu Thr Asn Xaa Lys Arg Thr Glu
1               5                   10                  15

Glu Gly Asn

<210> SEQ ID NO 121
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-beta Ala
<220> FEATURE:
<221> NAME/KEY: MOD_RES
<222> LOCATION: (6)..(6)
<223> OTHER INFORMATION: Lys modified with a unique side chain
<220> FEATURE:
<221> NAME/KEY: MOD_RES
<222> LOCATION: (8)..(8)
<223> OTHER INFORMATION: Any stapling amino acid
<220> FEATURE:
<221> NAME/KEY: MOD_RES
<222> LOCATION: (12)..(12)
<223> OTHER INFORMATION: Any stapling amino acid
<220> FEATURE:
<223> OTHER INFORMATION: See specification as filed for detailed
      description of substitutions and preferred embodiments

<400> SEQUENCE: 121

Xaa Arg Arg Phe Phe Gly Lys Xaa Leu Thr Asn Xaa Leu Arg Thr Glu
1               5                   10                  15
```

Glu Gly Asn

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any stapling amino acid
<220> FEATURE:
<221> NAME/KEY: MOD_RES
<222> LOCATION: (8)..(8)
<223> OTHER INFORMATION: Any stapling amino acid

<400> SEQUENCE: 122

Phe Phe Gly Xaa Tyr Leu Thr Xaa Ile Leu Lys Thr Glu Glu Gly Asn
1               5                   10                  15

<210> SEQ ID NO 123
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (16)..(16)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 123

Arg Arg Phe Phe Gly Ile Xaa Leu Thr Asn Xaa Leu Arg Thr Glu Lys
1               5                   10                  15

Gly Asn

<210> SEQ ID NO 124
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 124

Arg Arg Phe Phe Gly Ile Xaa Leu Thr Asn Xaa Lys Lys Thr Glu Lys
1               5                   10                  15

Gly Asn

```
<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (12)..(12)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 125

Arg Arg Phe Phe Gly Ile Xaa Leu Thr Asn Xaa Lys Arg Thr Glu Glu
1               5                   10                  15

Gly Asn

<210> SEQ ID NO 126
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (12)..(12)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 126

Arg Arg Phe Phe Gly Ile Xaa Leu Thr Asn Xaa Lys Arg Thr Glu Glu
1               5                   10                  15

Gly Asn

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
```

```
<400> SEQUENCE: 127

Arg Arg Phe Phe Gly Ile Xaa Leu Thr Asn Xaa Leu Lys Thr Glu Lys
1               5                   10                  15

Gly Asn

<210> SEQ ID NO 128
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (16)..(16)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 128

Arg Arg Phe Phe Gly Ile Xaa Leu Thr Asn Xaa Leu Arg Thr Glu Lys
1               5                   10                  15

Gly Asn

<210> SEQ ID NO 129
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid

<400> SEQUENCE: 129

Arg Arg Phe Phe Gly Ile Xaa Leu Thr Asn Xaa Lys Lys Thr Glu Lys
1               5                   10                  15

Gly Asn Pro Lys
            20

<210> SEQ ID NO 130
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
```

```
<220> FEATURE:
<221> NAME/KEY: MOD_RES
<222> LOCATION: (20)..(20)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 130

Arg Arg Phe Phe Gly Ile Xaa Leu Thr Asn Xaa Leu Arg Thr Glu Glu
1               5                  10                  15

Gly Asn Pro Lys
            20

<210> SEQ ID NO 131
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any stapling amino acid
<220> FEATURE:
<221> NAME/KEY: MOD_RES
<222> LOCATION: (11)..(11)
<223> OTHER INFORMATION: Any stapling amino acid
<220> FEATURE:
<221> NAME/KEY: MOD_RES
<222> LOCATION: (20)..(20)
<223> OTHER INFORMATION: Lys modified with a unique side chain
<220> FEATURE:
<223> OTHER INFORMATION: See specification as filed for detailed
      description of substitutions and preferred embodiments

<400> SEQUENCE: 131

Arg Arg Phe Phe Gly Ile Xaa Leu Thr Asn Xaa Leu Arg Thr Glu Glu
1               5                  10                  15

Gly Asn Pro Lys
            20

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Glu Asp His Tyr
1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis

<400> SEQUENCE: 133

His His His His His His
1               5

<210> SEQ ID NO 134
<211> LENGTH: 16
```

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Phe or any conservative amino acid substitution
<220> FEATURE:
<221> NAME/KEY: MOD_RES
<222> LOCATION: (3)..(3)
<223> OTHER INFORMATION: Gly or any conservative amino acid substitution
<220> FEATURE:
<221> NAME/KEY: MOD_RES
<222> LOCATION: (4)..(4)
<223> OTHER INFORMATION: Ile or any conservative amino acid substitution
<220> FEATURE:
<221> NAME/KEY: MOD_RES
<222> LOCATION: (5)..(5)
<223> OTHER INFORMATION: Tyr or any conservative amino acid substitution
<220> FEATURE:
<221> NAME/KEY: MOD_RES
<222> LOCATION: (6)..(6)
<223> OTHER INFORMATION: Leu or any conservative amino acid substitution
<220> FEATURE:
<221> NAME/KEY: MOD_RES
<222> LOCATION: (7)..(7)
<223> OTHER INFORMATION: Thr or any conservative amino acid substitution
<220> FEATURE:
<221> NAME/KEY: MOD_RES
<222> LOCATION: (8)..(8)
<223> OTHER INFORMATION: Asn or any conservative amino acid substitution
<220> FEATURE:
<221> NAME/KEY: MOD_RES
<222> LOCATION: (9)..(9)
<223> OTHER INFORMATION: Ile or any conservative amino acid substitution
<220> FEATURE:
<221> NAME/KEY: MOD_RES
<222> LOCATION: (10)..(10)
<223> OTHER INFORMATION: Leu or any conservative amino acid substitution
<220> FEATURE:
<221> NAME/KEY: MOD_RES
<222> LOCATION: (11)..(11)
<223> OTHER INFORMATION: Lys or any conservative amino acid substitution
<220> FEATURE:
<221> NAME/KEY: MOD_RES
<222> LOCATION: (12)..(12)
<223> OTHER INFORMATION: Thr or any conservative amino acid substitution
<220> FEATURE:
<221> NAME/KEY: MOD_RES
<222> LOCATION: (13)..(14)
<223> OTHER INFORMATION: Glu or any conservative amino acid substitution
<220> FEATURE:
<221> NAME/KEY: MOD_RES
<222> LOCATION: (15)..(15)
<223> OTHER INFORMATION: Gly or any conservative amino acid substitution
<220> FEATURE:
<221> NAME/KEY: MOD_RES
<222> LOCATION: (16)..(16)
<223> OTHER INFORMATION: Asn or any conservative amino acid substitution
<220> FEATURE:
<223> OTHER INFORMATION: See specification as filed for detailed
      description of substitutions and preferred embodiments

<400> SEQUENCE: 134

Xaa Xaa Xaa Xaa Xaa Xaa Xaa Xaa Xaa Xaa Xaa Xaa Xaa Xaa Xaa Xaa
1               5                   10                  15

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(2)
<223> OTHER INFORMATION: Phe or any conservative amino acid substitution
<220> FEATURE:
<221> NAME/KEY: MOD_RES
<222> LOCATION: (3)..(3)
<223> OTHER INFORMATION: Gly or any conservative amino acid substitution
<220> FEATURE:
<221> NAME/KEY: MOD_RES
<222> LOCATION: (4)..(4)
<223> OTHER INFORMATION: Ile or any conservative amino acid substitution
<220> FEATURE:
<221> NAME/KEY: MOD_RES
<222> LOCATION: (5)..(5)
<223> OTHER INFORMATION: Tyr or any conservative amino acid substitution
<220> FEATURE:
<221> NAME/KEY: MOD_RES
<222> LOCATION: (6)..(6)
<223> OTHER INFORMATION: Leu or any conservative amino acid substitution
<220> FEATURE:
<221> NAME/KEY: MOD_RES
<222> LOCATION: (7)..(7)
<223> OTHER INFORMATION: Thr or any conservative amino acid substitution
<220> FEATURE:
<221> NAME/KEY: MOD_RES
<222> LOCATION: (8)..(8)
<223> OTHER INFORMATION: Asn or any conservative amino acid substitution
<220> FEATURE:
<221> NAME/KEY: MOD_RES
<222> LOCATION: (9)..(9)
<223> OTHER INFORMATION: Ile or any conservative amino acid substitution
<220> FEATURE:
<221> NAME/KEY: MOD_RES
<222> LOCATION: (10)..(10)
<223> OTHER INFORMATION: Leu or any conservative amino acid substitution
<220> FEATURE:
<221> NAME/KEY: MOD_RES
<222> LOCATION: (11)..(11)
<223> OTHER INFORMATION: Lys or any conservative amino acid substitution
<220> FEATURE:
<221> NAME/KEY: MOD_RES
<222> LOCATION: (12)..(12)
<223> OTHER INFORMATION: Thr or any conservative amino acid substitution
<220> FEATURE:
<221> NAME/KEY: MOD_RES
<222> LOCATION: (13)..(14)
<223> OTHER INFORMATION: Glu or any conservative amino acid substitution
<220> FEATURE:
<221> NAME/KEY: MOD_RES
<222> LOCATION: (15)..(15)
<223> OTHER INFORMATION: Gly or any conservative amino acid substitution
<220> FEATURE:
<221> NAME/KEY: MOD_RES
<222> LOCATION: (16)..(16)
<223> OTHER INFORMATION: Asn or any conservative amino acid substitution
<220> FEATURE:
<223> OTHER INFORMATION: See specification as filed for detailed
      description of substitutions and preferred embodiments

<400> SEQUENCE: 135

Xaa Xaa Xaa Xaa Xaa Xaa Xaa Xaa Xaa Xaa Xaa Xaa Xaa Xaa Xaa Xaa
1               5                   10                  15

Pro

<210> SEQ ID NO 136
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (4)..(4)
<223> OTHER INFORMATION: (R)-2-amino-2-methyl-dec-9-enoic acid
<220> FEATURE:
<221> NAME/KEY: MOD_RES
<222> LOCATION: (11)..(11)
<223> OTHER INFORMATION: Any stapling amino acid

<400> SEQUENCE: 136

Arg Arg Phe Xaa Gly Ile Tyr Leu Thr Asn Xaa Leu Lys Thr Glu Glu
1               5                   10                  15

Gly Asn
```

STABILIZED SOS1 PEPTIDES

CROSS-REFERENCE TO RELATED APPLICATIONS

The present application is the National Phase of International Application Serial No. PCT/US2014/028436, filed on Mar. 14, 2014, which claims the benefit of U.S. Provisional Patent Application Ser. No. 61/798,254, filed on Mar. 15, 2013, both of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Mar. 14, 2014, is named 00530-0308WO1_SL.txt and is 73,220 bytes in size.

TECHNICAL FIELD

This disclosure relates to structurally stabilized therapeutic peptides related to KRAS guanidine exchange factor (SOS1), and methods of using such peptides in the treatment of cancer.

BACKGROUND

Activating mutations in KRAS represent the most frequent pathologic driving force among the three protein isoforms of RAS (K-, N- and H-RAS). KRAS mutations are present in approximately 30% of tumors, and at even higher frequencies in cancers of the pancreas, lung, thyroid gland, colon, and liver. In pancreatic ductal adenocarcinomas (PDAC), one of the most lethal cancers with 5-year survival rates of less than 5%, activating KRAS mutations are found in more than 90% of the tumors [2]. Moreover, these mutations have been causally linked to the initiation and progression of PDAC [3, 4]. In general, KRAS mutations are associated with poor prognosis and treatment resistance of human tumors [5]. For example, KRAS-mutant lung and colon cancers are refractory to both small molecule EGFR inhibitors and antibodies that target overexpressed EGFR [6]. Thus, patients with KRAS mutations are non-responsive to EGFR-targeted therapies, further limiting their therapeutic options.

KRAS is a membrane-bound signaling protein that transmits growth factor receptor (such as EGFR) signals to downstream pathways, such as MAPK, PI3K and others. KRAS cycles between an active, GTP-loaded form and an inactive, GDP-bound state. Upon activation by growth factor signaling, KRAS guanidine exchange factor (GEF), a protein called SOS1, promotes the GTP-loading and thus activation of KRAS. The KRAS-GDP to KRAS-GTP transition that is catalyzed by SOS1 represents the rate-limiting step of this cyclic reaction[7]. Oncogenic mutations in KRAS are typically point mutations that stabilize the active, GTP-bound state of KRAS.

Despite the insights into the mechanism of KRAS and its pathologic mutations, the development of targeted inhibitors of KRAS for therapeutic benefit has been elusive and remains a formidable challenge [8, 9, 10, 11, 12, 13, 14 and 15].

SUMMARY

The present disclosure provides structurally stabilized peptides related to (e.g., sharing sequence homology with) portions or fragments of SOS1, and methods for using such stabilized peptides as therapeutic and/or prophylactic agents. Certain of these stabilized peptides target both wild-type and mutant forms of KRAS and its mutant isoforms with nanomolar binding affinity and reactivate cell death in KRAS-driven and mutant KRAS-driven cancer cells, including cervical, colon, and lung carcinomas. Importantly, SAH-SOS1 peptides were also designed to incorporate guanine peptide-nucleic acid monomer moieties, with the goal of jointly engaging the SOS1 and GTP binding sites on KRAS and its mutant isoforms and homologues. These hybrid constructs demonstrate enhanced KRAS binding affinity compared to the parent SAH-SOS1 peptides and correspondingly manifest greater cytotoxicity in KRAS-driven cancer cells.

In some aspects, the present disclosure provides internally cross-linked polypeptides comprising the amino acid sequence $A_0B_0C_0D_0E_0F_0G_0\ A_1B_1C_1D_1E_1F_1G_1\ A_2B_2$ (SEQ ID NO:1) wherein: $A_0$ is F or a conservative substitution; $B_0$ is F or a conservative substitution; $C_0$ is G or a conservative substitution; $D_0$ is I or a conservative substitution; $E_0$ is Y or a conservative substitution; $F_0$ is L or a conservative substitution; $G_0$ is T or a conservative substitution; $A_1$ is N or a conservative substitution; $B_1$ is I or a conservative substitution; $C_1$ is L or a conservative substitution; $D_1$ is K or a conservative substitution; $E_1$ is T or a conservative substitution; $F_1$ is E or a conservative substitution; $G_1$ is E or a conservative substitution; $A_2$ is G or a conservative substitution; $B_2$ is N or a conservative substitution wherein: the side chains of two amino acids separated by two, three or six amino acids are replaced by an internal staple; the side chains of three amino acids are replaced by internal staples and/or an internal stitch; the side chains of four amino acids are replaced by internal staples, internal stiches, or a combination of internal staples and stiches; or the side chains of at least four amino acids are replaced by internal staples, internal stiches, or a combination of internal staples and stiches.

In some embodiments, internally cross-linked polypeptides of the disclosure include the sequence $A_0B_0C_0D_0E_0F_0G_0\ A_1B_1C_1D_1E_1F_1G_1\ A_2B_2$ (SEQ ID NO:134), wherein: $A_0$ is F, $B_0$ is F, $C_0$ is G, $D_0$ is I, $E_0$ is Y, $F_0$ is L, $G_0$ is T, $A_1$ is N, $B_1$ is I, $C_1$ is L, $D_1$ is K, $E_1$ is T, $F_1$ is E, $G_1$ is E, $A_2$ is G, $B_2$ is N, wherein: none, one or more (e.g., 1, 2, 3, 4, 5, 6, 7, 8, 9, 10, 11, 12, 13, 14, 15, 16, 17, 18) of $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$ are replaced by a conservative amino acid substitution or a conservative substitution that does not alter the binding face of the peptide.

$A_0B_0C_0D_0E_0F_0G_0\ A_1B_1C_1D_1E_1F_1G_1\ A_2B_2$Pro (SEQ ID NO:135, wherein: $A_0$ is F, $B_0$ is F, $C_0$ is G, $D_0$ is I, $E_0$ is Y, $F_0$ is L, $G_0$ is T, $A_1$ is N, $B_1$ is I, $C_1$ is L, $D_1$ is K, $E_1$ is T, $F_1$ is E, $G_1$ is E, $A_2$ is G, $B_2$ is N, wherein: none, one or more (e.g., 1, 2, 3, 4, 5, 6, 7, 8, 9, 10, 11, 12, 13, 14, 15, 16, 17, 18) of $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$ are replaced by a conservative amino acid substitution or a conservative substitution that does not alter the binding face of the peptide.

In some cases of SEQ ID NOs:134 and 135, $C_1$ and $D_1$ are replaced by KR or K'R, where K' is K substituted at N with a guanine nucleoside or guanine nucleoside analog. In some cases the side chain of an amino acid is substituted with a guanine nucleoside analog. In some cases, $D_1$ and $G_1$ are replaced R and K, respectively or R and K' respectively. In some cases, $D_1$ and Pro are replaced R and K, respectively or R and K' respectively.

In some embodiments, internally cross-linked polypeptides of the disclosure includes the sequence FFGIYLTNILKTEEGN (SEQ ID NO:2); the sequence FFGIYLTNILKTEEGNRR (SEQ ID NO:3) the sequence RRFFGIYLTNILKTEEGN (SEQ ID NO:4); the sequence FFGIYXTNILKTEEGNPELVRR (SEQ ID NO:5); the sequence RRFFGIYLTNILKTEEGNPELV (SEQ ID NO:6); the sequence FFGIYLTNILKTEEGNPELV (SEQ ID NO:7); the sequence FFGIYLTNILKTEEGNR (SEQ ID NO:8) the sequence RFFGIYLTNILKTEEGN (SEQ ID NO:9); the sequence FFGIYXTNILKTEEGNPELVR (SEQ ID NO:10); and the sequence RFFGIYLTNILKTEEGNPELV (SEQ ID NO:11), wherein the side chains of two amino acids separated by three or six amino acids comprises an internal staple selected from Table 1 (FIG. 23). In some embodiments, the internally cross-linked peptide includes 1, 2, 3, 4, or 5 amino acid substitutions, preferably conservative amino acid substitutions. In addition to these substitutions, the peptide can include one amino acid (preferably one of the three carboxy-terminal most amino acids) whose side chain is replaced by a group having the structure of Formula I.

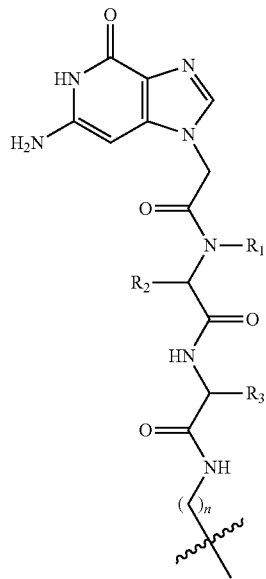

Formula I wherein n is 1, 2, 3, or 4 and R1, R2 and R3 are independently:

| R1 | R2 and R3 |
|---|---|
| —H | —H |
| —CH₃ | —CH₃ |
| —(CH₂)ₙCH₃ | —(CH₂)ₙCH₃ |
| 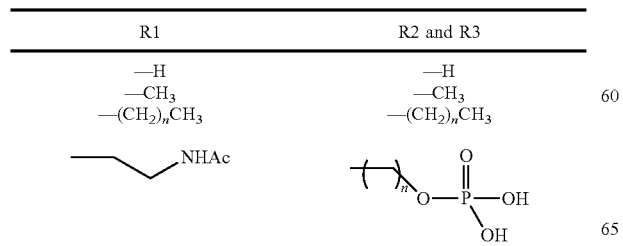 | 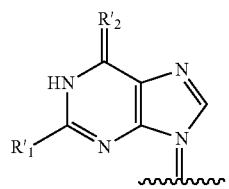 |

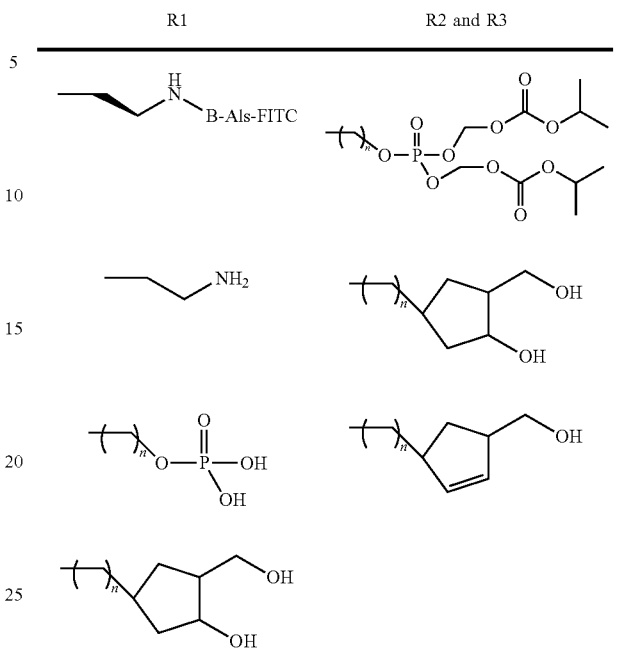

In some embodiments of a stapled, the side-chain of an amino acid is replaced by Formula II:

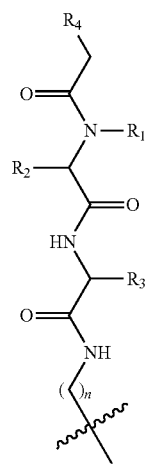

Formula II wherein: n is 1, 2, 3, or 4; R1, R2 and R3 are as in Formula I, and R4 is selected from Formula III and Formula IV:

Formula III

-continued

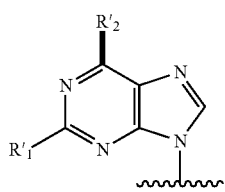

Formula IV wherein R'1 and R'2 are independently:

| R'1 | R'2 |
|---|---|
| —NH$_2$ | —NH$_2$ |
| —H | =O |
| | —NH-cyclopropyl |

In some embodiments, R1, R2 and R3 in Formula I or Formula II are independently H or methyl.

In some cases the side chain of an amino acid is substituted with a guanine nucleoside analog.

In preferred embodiments, the staple is an alkyl, alkenyl, or alkynl.

In some embodiments, internally cross-linked polypeptides of the disclosure include an internal staple replacing the side chains of two amino acids separated by three or six amino acids comprises an internal staple selected from Table 1 (FIG. 23). In some embodiments, internally cross-linked peptides are selected from the group consisting of SEQ ID NOs:1-73. In some embodiments, the internal staples and/or the internal stitch replacing the side chains of the three amino acids includes an internal stitch selected from Table 1 (FIG. 23). In some embodiments, the internal staples and/or the internal stitch comprises at least two internal staples (replacing the side chains of 4 amino acids, i.e., each staple is between two amino acids separated by 3 amino acids). In some embodiments, the internal staples and/or the internal stitch comprises a combination of at least one internal staple and an internal stitch. In some embodiments, the internal stitch replaces the side chain of a first amino acid and a second and a third amino acid thereby cross-linking the first amino acid (which lies between the second and third amino acids) to the second and third amino acid via an internal cross-link, wherein the first and second amino acid are separated by two, three, or six amino acids, the first and the third amino acids are separated by two, three, or six amino acids, and the second and third amino acids are distinct amino acids. In some embodiments, the internal stitch replacing the side chains of the three amino acids cross-links a pair of amino acids separated by two, three, or six amino acids. In some embodiments, the side chains of the four amino acids of the internally cross-linked polypeptides of the disclosure are replaced by two distinct internal staples. In some embodiments, a first of the two distinct internal staples cross-links a first pair of amino acids separated by two, three, or six amino acids, and a second of the at least two distinct internal staples cross-links a second pair of amino acids separated by two, three, or six amino acids. In some embodiments, internally cross-linked polypeptides of the disclosure are selected from the group consisting of SEQ ID NOs: 1-73 or the group consisting of SEQ ID NOs: 1-57 is has one amino acid (e.g., one of the three carboxy-terminal most amino acids) whose side chain is replaced by a group that includes a guanine nucleoside analog having the structure of Formula I.

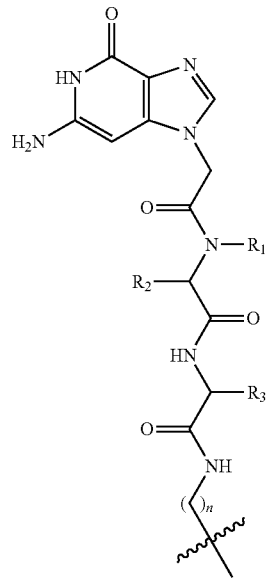

Formula I wherein R1, R2 and R3 are independently:

| R1 | R2 and R3 |
|---|---|
| —H | —H |
| —CH$_3$ | —CH$_3$ |
| —(CH$_2$)$_n$CH$_3$ | —(CH$_2$)$_n$CH$_3$ |
| —(CH$_2$)$_n$NHAc | phosphate group |
| —(CH$_2$)$_n$NH-B-Als-FITC | bis(isopropyloxycarbonyloxymethyl) phosphate |
| —(CH$_2$)$_n$NH$_2$ | cyclopentane-diol-methyl |
| phosphate group | cyclopentene-methyl-OH |
| cyclopentane-diol-methyl | |

In some embodiments of a stapled, the side-chain of an amino acid is replaced by Formula II

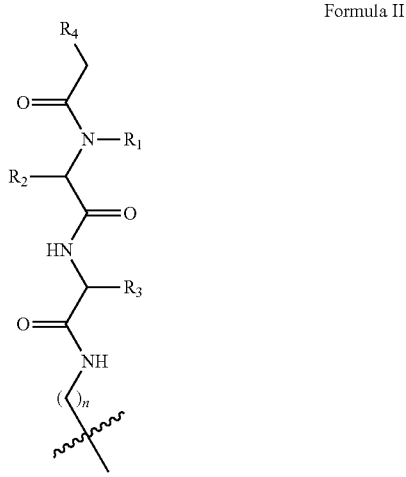

Formula II wherein R₄ is selected from Formula III and Formula IV:

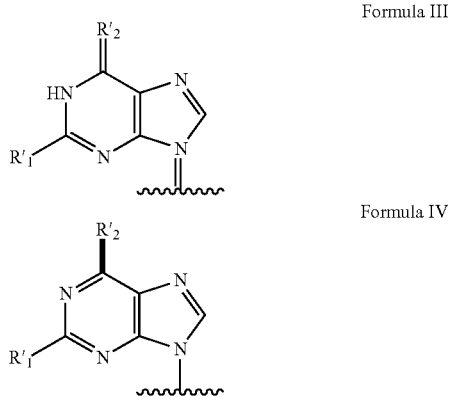

Formula III

Formula IV wherein R'1 and R'2 are independently:

| R'1 | R'2 |
|---|---|
| —NH₂ | —NH₂ |
| —H | =O |

—N(H)◁

In some embodiments, internally cross-linked polypeptides of the disclosure include internal staples, internal stiches, or a combination of internal staples and internal stitches replacing the side chains of at least four amino acids, such as at least one staple and at least one stitch. In some embodiments, the at least one staple cross-links a pair of amino acids separated by two, three, or six amino acids and the at least one stitch cross-links a first amino acid to a second amino acid and a third amino acid, wherein the first and second amino acid are separated by two, three, or six amino acids, the first and the third amino acids are separated by two, three, or six amino acids, and the second and third amino acids are distinct amino acids. In some embodiments, such staples are selected from Table 1 (FIG. 23).

In some aspects, the disclosure provides pharmaceutical compositions that include one or more internally cross-linked polypeptides of the disclosure. In some embodiments, such pharmaceutical compositions can also include one or more medicaments for the treatment of cancer and/or the alleviation of one or more symptoms associated with cancer.

In some aspects, the disclosure provides methods for treating cancer in a subject. These methods can include selecting a subject suffering from cancer; and administering to the subject an effective amount of the stabilized peptides of claims described herein. In some embodiments, methods include assessing a level of KRAS activity in the subject before and after treatment; and continuing treatment until a decrease in the level of KRAS activity is observed and/or diseased cell viability is compromised.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

FIG. 1A provides examples of non-natural amino acids (Z) containing olefinic tethers where 'Z is (R)-amino-2-methyl-dec-9-enoic acid' that can be used to generated hydrocarbon stapled SOS1 peptides.

FIG. 1B provides examples of single staple compositions spanning i, i+3; i, i+4, and i, i+7 positions for singly stapled SOS1 peptides.

FIGS. 2A and 2B depict the structure of the interaction between KRAS and SOS1, structure of the SOS1 interacting alpha-helix and the sequence of certain stabilized SOS1 peptides (SEQ ID Nos: 12-25), see Table 2 below.

TABLE 2

Figure 1C:
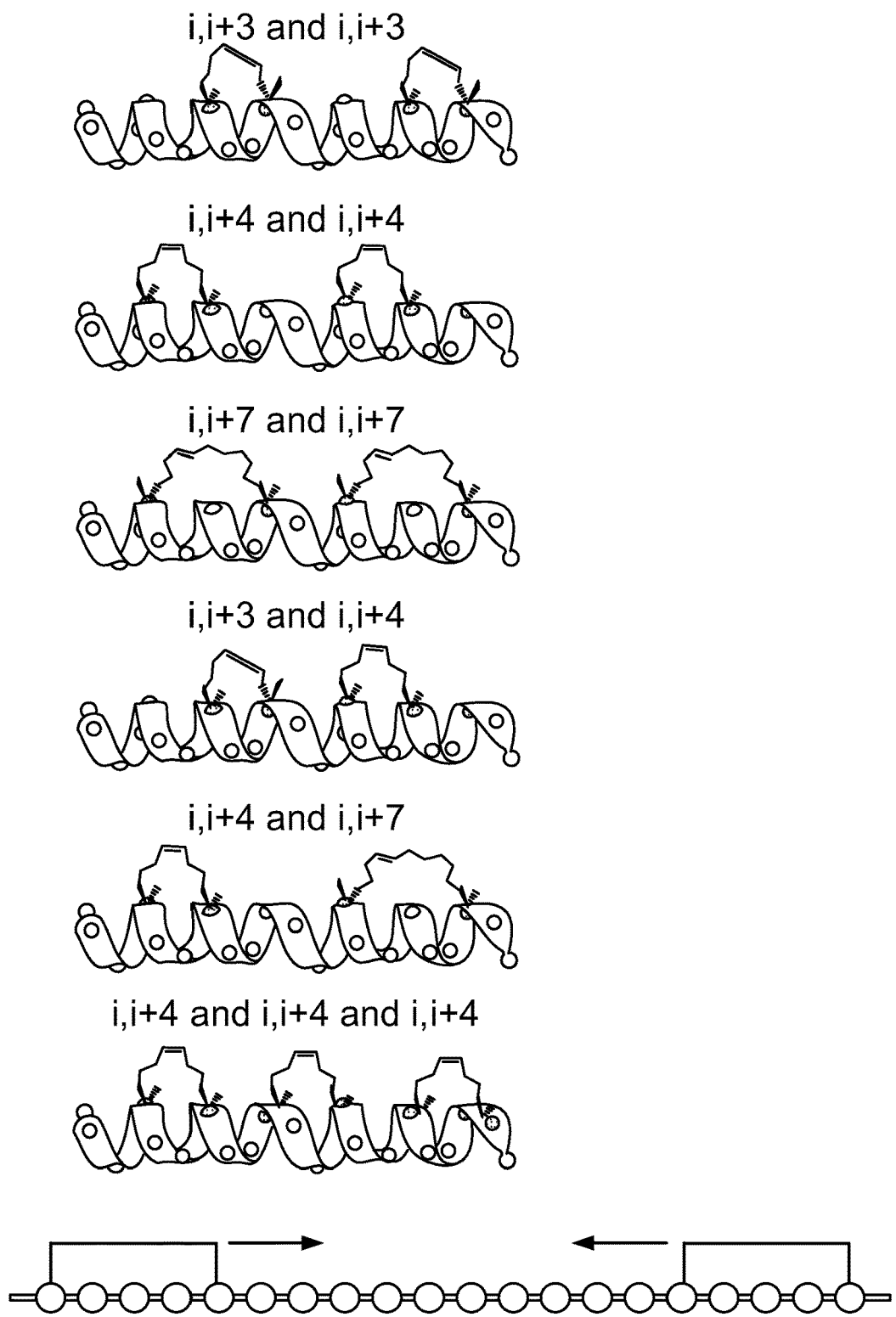
FIG. 1C provides examples of staple compositions for multiply stapled SOS1 peptides.

| SAH | Sequence | SEQ ID NO: |
|---|---|---|
| SAH-SOS$_{A1}$ | FXGIYXTNILKTEEGN | SEQ ID NO: 12 |
| SAH-SOS$_{A2}$ | RRFXGIYXTNILKTEEGN | SEQ ID NO: 13 |
| SAH-SOS$_{A3}$ | FXGIYXTNILKTEEGNRR | SEQ ID NO: 14 |
| SAH-SOS$_{B2}$ | RRFFGXYLTXILKTEEGN | SEQ ID NO: 15 |
| SAH-SOS$_{C1}$ | FFGIXLTNXLKTEEGN | SEQ ID NO: 16 |
| SAH-SOS$_{C2}$ | RRFFGIXLTNXLKTEEGN | SEQ ID NO: 17 |
| SAH-SOS$_{C3}$ | FFGIXLTNXLKTEEGNRR | SEQ ID NO: 18 |
| SAH-SOS$_{D1}$ | FFGIYLTNXLKTXEGN | SEQ ID NO: 19 |
| SAH-SOS$_{D2}$ | RRFFGIYLTNXLKTXEGN | SEQ ID NO: 20 |
| SAH-SOS$_{D3}$ | FFGIYLTNXLKTXEGNRR | SEQ ID NO: 21 |

TABLE 2-continued

| SAH | Sequence | SEQ ID NO: |
|---|---|---|
| SAH-SOS$_{E2}$ | RRFFGIYLTNUCKTEXGN | SEQ ID NO: 22 |
| SAH-SOS$_{F2}$ | RRFFGIYLTNILKTXEGNX | SEQ ID NO: 23 |
| SAH-SOS$_{G2}$ | RRXFGIYLTXILKTEEGN | SEQ ID NO: 24 |
| SAH-SOS$_{H2}$ | RRFXGIYLTNXLKTEEGN | SEQ ID NO: 25 |

FIGS. 3A and B depict examples of stapled peptide compositions for RAS targeting (SEQ ID Nos: 26-121), see Table 3 below. "X" represents the stapling amino acid; peptides without the indicated N-terminal modification). The "SEDHY" side chain is disclosed as SEQ ID NO: 132.

TABLE 3

| N-terminus | Sequence | SEQ ID NO: |
|---|---|---|
| Ac | FXGIYXTNILKTEEGNRR | SEQ ID NO: 26 |
| Ac | RRFFGIXLTNXLKTEEGN | SEQ ID NO: 27 |
| Ac | FFGIXLTNXLKTEEGNRR | SEQ ID NO: 28 |
| Ac | RRFXGIYXTNILKTEEGN | SEQ ID NO: 29 |
| Ac | FFGIYLTNXLKTXEGNRR | SEQ ID NO: 30 |
| Ac | RRFFGIYLTNXLKTXEGN | SEQ ID NO: 31 |
| Ac | RRFFGXYLTXILKTEEGN | SEQ ID NO: 32 |
| Ac | RRZFGIYLTXILKTEEGN | SEQ ID NO: 33 |
| Ac | RRFFGIYLTNILKTXEGNX | SEQ ID NO: 34 |
| Ac | RRFZGIYLTNXLKTEEGN | SEQ ID NO: 35 |
| Ac | RRFFGIYLTNUCKTEXGN | SEQ ID NO: 36 |
| Ac | RRFFGIXLTNXLKTEEGNPEVL | SEQ ID NO: 37 |
| Ac | RRFFGIXLTNXLKTEEGNPEVLR | SEQ ID NO: 38 |
| Ac | RRFFGIXLTNXLRTEUGN | SEQ ID NO: 39 |
| Ac | RRFFGKXLTNXLRTEEGN | SEQ ID NO: 40 |
| Ac | RRFFGIXLTNXLRTEUGN | SEQ ID NO: 41 |
| Ac | RRFFGIXLTNXLRTECGN | SEQ ID NO: 42 |
| Ac | RRFFGJXLTNXLKTEEGN | SEQ ID NO: 43 |
| Ac | RRFFDIXLTNXLKTEEGN | SEQ ID NO: 44 |
| Ac | RRFFGIXDTNXLKTEEGN | SEQ ID NO: 45 |
| Ac | IWIAFEGIXLTNXLKTYERR | SEQ ID NO: 46 |
| Ac | RRFEGIXRLEXLKAEEAN | SEQ ID NO: 47 |
| Ac | RRFFGIXKTNXEKTEEGN | SEQ ID NO: 48 |
| Ac | RRFFGIXLTRXLKTEEGN | SEQ ID NO: 49 |
| Ac | RRFFGIXLTNXLRTEK(G-Gmono)GN | SEQ ID NO: 50 |
| Ac | RRFFGIXLTNXLRTEK(Gmono)GN | SEQ ID NO: 51 |
| Ac | RRFFGIXLTNXLRTEEGNPK(G-Gmono) | SEQ ID NO: 52 |
| Ac | RRFFGIXLTNXLRTEEGNPK(Gmono) | SEQ ID NO: 53 |
| Ac | RRFFGIXLTNXK(G-Gmono)RTEEGN | SEQ ID NO: 54 |
| Ac | RRFFGIXLTNXK(Gmono)RTEEGN | SEQ ID NO: 55 |
| Ac | RRFFG(SEDHY)KXLTNXLRTEEGN | SEQ ID NO: 56 |
| FITC-βAla | FXGIYXTNILKTEEGN | SEQ ID NO: 57 |
| FITC-βAla | FFGIXLTNXLKTEEGN | SEQ ID NO: 58 |
| FITC-βAla | FFGIYLTNXLKTXEGN | SEQ ID NO: 59 |
| FITC-βAla | RRFFGXYLTXILKTEEGN | SEQ ID NO: 60 |
| FITC-βAla | RRFZGIYLTNXLKTEEGN | SEQ ID NO: 61 |
| FITC-βAla | RRFFGIYLTNUCKTEXGN | SEQ ID NO: 62 |
| FITC-βAla | RRFFGIXLTNXLKTEEGNPEVL | SEQ ID NO: 63 |
| FITC-βAla | RRFFGIXLTNXLRTEUGN | SEQ ID NO: 64 |
| FITC-βAla | RRFFGKXLTNXLRTEEGN | SEQ ID NO: 65 |
| FITC-βAla | RRFFGJXLTNXLKTEEGN | SEQ ID NO: 66 |
| FITC-βAla | RRFFDIXLTNXLKTEEGN | SEQ ID NO: 67 |
| FITC-βAla | RRFFGIXDTNXLKTEEGN | SEQ ID NO: 68 |
| FITC-βAla | IWIAFEGIXLTNXLKTYERR | SEQ ID NO: 69 |
| FITC-βAla | RRFEGMLEXLKAEEAN | SEQ ID NO: 70 |
| FITC-βAla | RRFFGIXKTNXEKTEEGN | SEQ ID NO: 71 |
| FITC-βAla | RRFFGIXLTRXLKTEEGN | SEQ ID NO: 72 |
| FITC-βAla | RRFFGIXLTNXLRTEK(G-Gmono)GN | SEQ ID NO: 73 |
| Ac | FXGIYXTNILKTEEGN | SEQ ID NO: 74 |
| Ac | FFGIXLTNXLKTEEGN | SEQ ID NO: 75 |
| Ac | FFGIYLTNXLKTXEGN | SEQ ID NO: 76 |
| Ac | FFGIYLTNIXKTEXGN | SEQ ID NO: 77 |
| Ac | FFGIXKTNXEKTEEGN | SEQ ID NO: 78 |
| Ac | FFGXYLTXILKTEEGN | SEQ ID NO: 79 |
| Ac | ZFGIYLTXILKTEEGN | SEQ ID NO: 80 |
| Ac | FFGIYLTNILKTXEGNX | SEQ ID NO: 81 |
| Ac | FZGIYLTNXLKTEEGN | SEQ ID NO: 82 |
| Ac | FFDIXLTNXLKTEEGN | SEQ ID NO: 83 |
| Ac | FFGIXDTNXLKTEEGN | SEQ ID NO: 84 |
| Ac | FFGIXLTRXLKTEEGN | SEQ ID NO: 85 |
| Ac | FFGUXLTNXLKTEEGN | SEQ ID NO: 86 |
| Ac | FFGKXLTNXLKTEEGN | SEQ ID NO: 87 |
| Ac | FFGIYLTNILKTEEGN | SEQ ID NO: 88 |

TABLE 3-continued

| N-terminus | Sequence | SEQ ID NO: |
|---|---|---|
| Ac | RRFFGIXLTNXLRTEKGN | SEQ ID NO: 89 |
| Ac | RRFFGUXLTNXLKTEEGN | SEQ ID NO: 90 |
| FITC-βAla | FXGIYXTNILKTEEGNRR | SEQ ID NO: 91 |
| FITC-βAla | RRFFGIXLTNXLKTEEGN | SEQ ID NO: 92 |
| FITC-βAla | FFGIXLTNXLKTEEGNRR | SEQ ID NO: 93 |
| FITC-βAla | RRFXGIYXTNILKTEEGN | SEQ ID NO: 94 |
| FITC-βAla | RRFFGIYLTNXLKTXEGN | SEQ ID NO: 95 |
| FITC-βAla | FFGIYLTNXLKTXEGNRR | SEQ ID NO: 96 |
| FITC-βAla | FFGIYLTNIXKTEXGN | SEQ ID NO: 97 |
| FITC-βAla | FFGIXKTNXEKTEEGN | SEQ ID NO: 98 |
| FITC-βAla | FFGXYLTXILKTEEGN | SEQ ID NO: 99 |
| FITC-βAla | ZFGIYLTXILKTEEGN | SEQ ID NO: 100 |
| FITC-βAla | FFGIYLTNILKTXEGNX | SEQ ID NO: 101 |
| FITC-βAla | FZGIYLTNXLKTEEGN | SEQ ID NO: 102 |
| FITC-βAla | FFDIXLTNXLKTEEGN | SEQ ID NO: 103 |
| FITC-βAla | FFGIXDTNXLKTEEGN | SEQ ID NO: 104 |
| FITC-βAla | FFGIXLTRXLKTEEGN | SEQ ID NO: 105 |
| FITC-βAla | FFGUXLTNXLKTEEGN | SEQ ID NO: 106 |
| FITC-βAla | FFGKXLTNXLKTEEGN | SEQ ID NO: 107 |
| FITC-βAla | FFGIYLTNILKTEEGN | SEQ ID NO: 108 |
| FITC-βAla | RRZFGIYLTXILKTEEGN | SEQ ID NO: 109 |
| FITC-βAla | RRFFGIYLTNILKTXEGNX | SEQ ID NO: 110 |
| FITC-βAla | RRFFGIXLTNXLKTEEGNPEVLR | SEQ ID NO: 111 |
| FITC-βAla | RRFFGIXLTNXLRTEKGN | SEQ ID NO: 112 |
| FITC-βAla | RRFFGIXLTNXCRTEEGN | SEQ ID NO: 113 |
| FITC-βAla | RRFFGIXLTNXLRTECGN | SEQ ID NO: 114 |
| FITC-βAla | RRFFGUXLTNXLKTEEGN | SEQ ID NO: 115 |
| FITC-βAla | RRFFGIXLTNXLRTEK(-Gmono)GN | SEQ ID NO: 116 |
| FITC-βAla | RRFFGIXLTNXLRTEEGNPK(-G-Gmono) | SEQ ID NO: 117 |
| FITC-βAla | RRFFGIXLTNXLRTEEGNPK(-Gmono) | SEQ ID NO: 118 |
| FITC-βAla | RRFFGIXLTNXK(-G-Gmono)RTEEGN | SEQ ID NO: 119 |
| FITC-βAla | RRFFGIXLTNXK(-Gmono)RTEEGN | SEQ ID NO: 120 |
| FITC-βAla | RRFFGK(SEDHY)XLTNXLRTEEGN | SEQ ID NO: 121 |

Figure 4A:
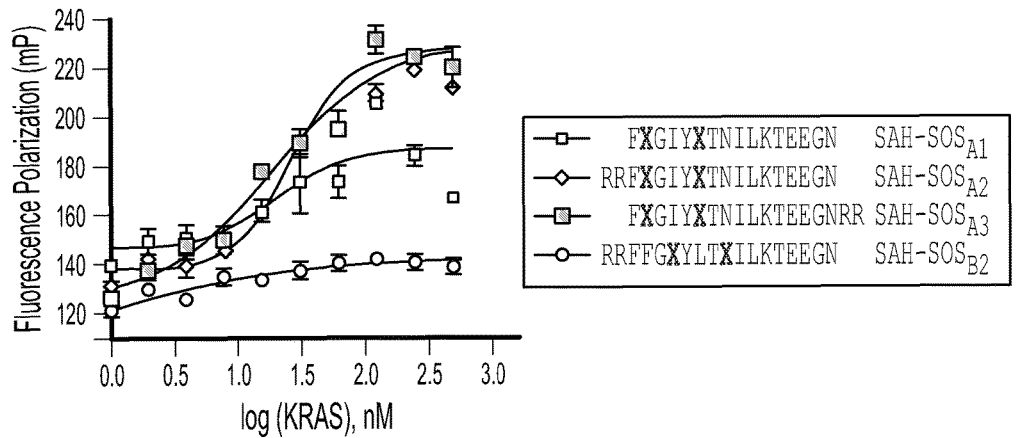
Figure 4B:
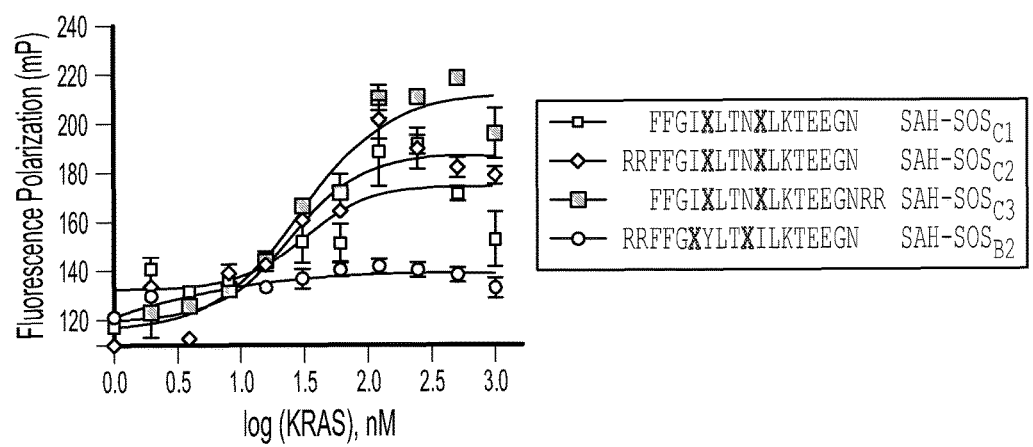
Figure 4C:
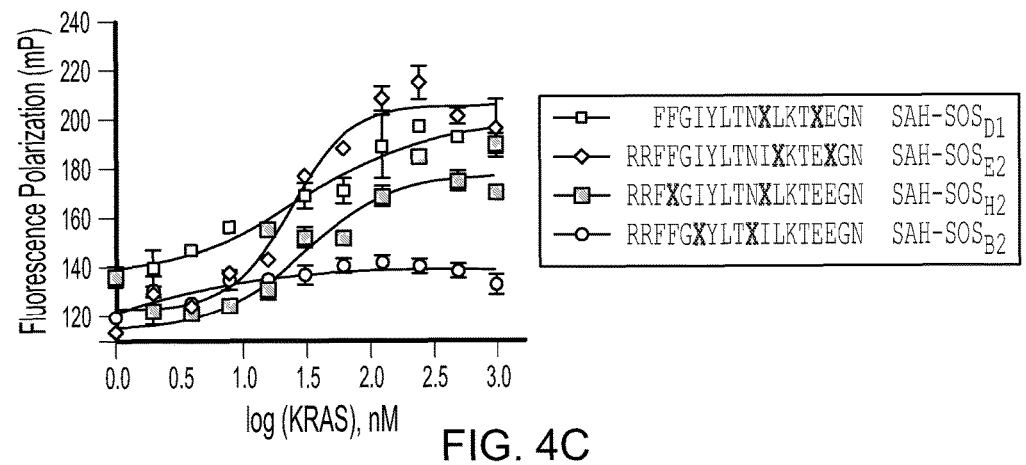

FIGS. 4A-C depict the results of a study demonstrating the affinity of SAH-SOS peptides for KRAS (SEQ ID Nos: 12-19, 22 and 25 respectively, in order of appearance).

FIG. 5 is a table providing the binding affinity of various SAH-SOS peptides (SEQ ID Nos: 12-19, 22 and 136, respectively, in order of appearance) to wild-type KRAS, as measured by fluorescence polarization binding assay.

Figure 6A:
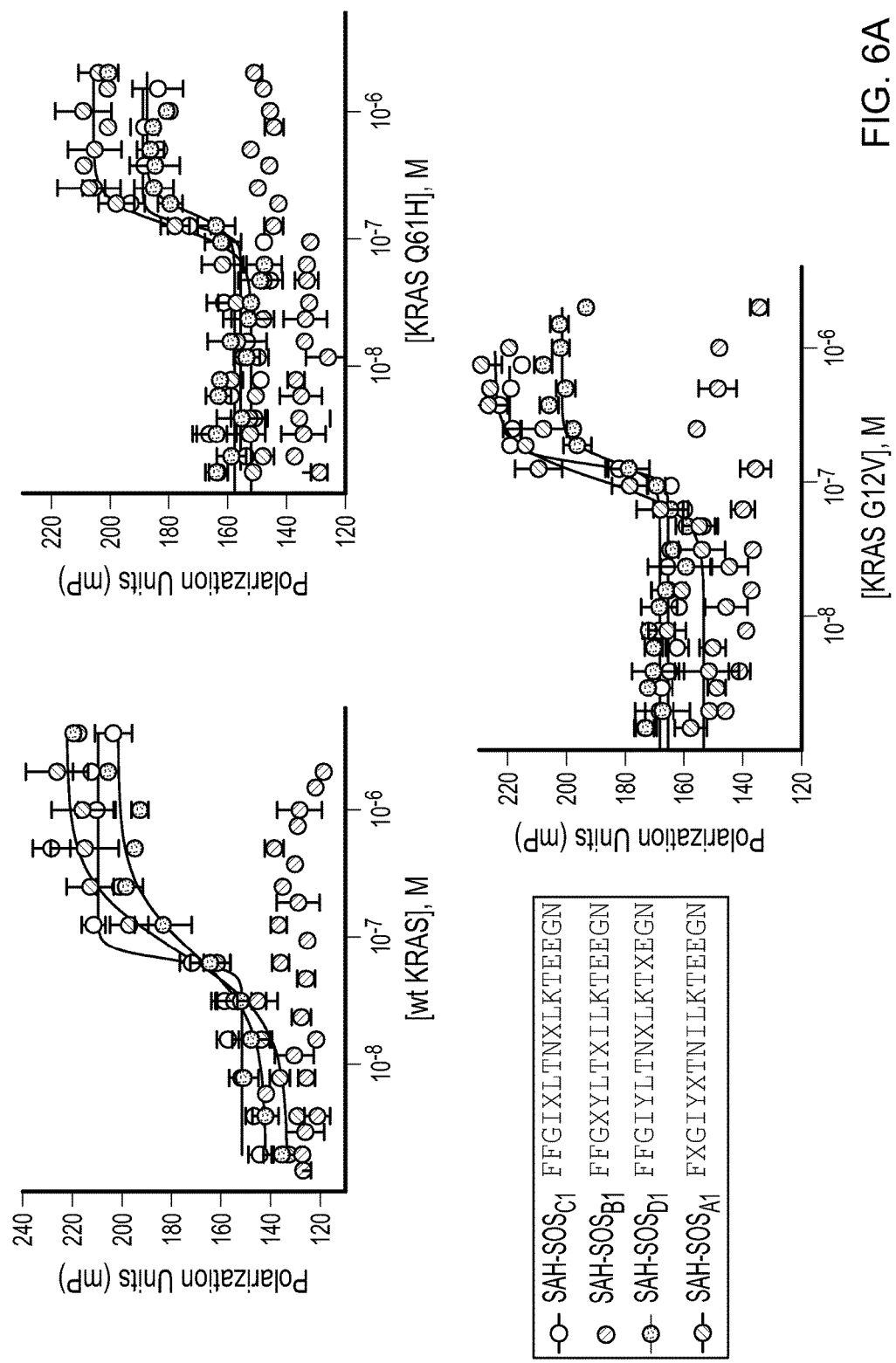
Figure 6A:
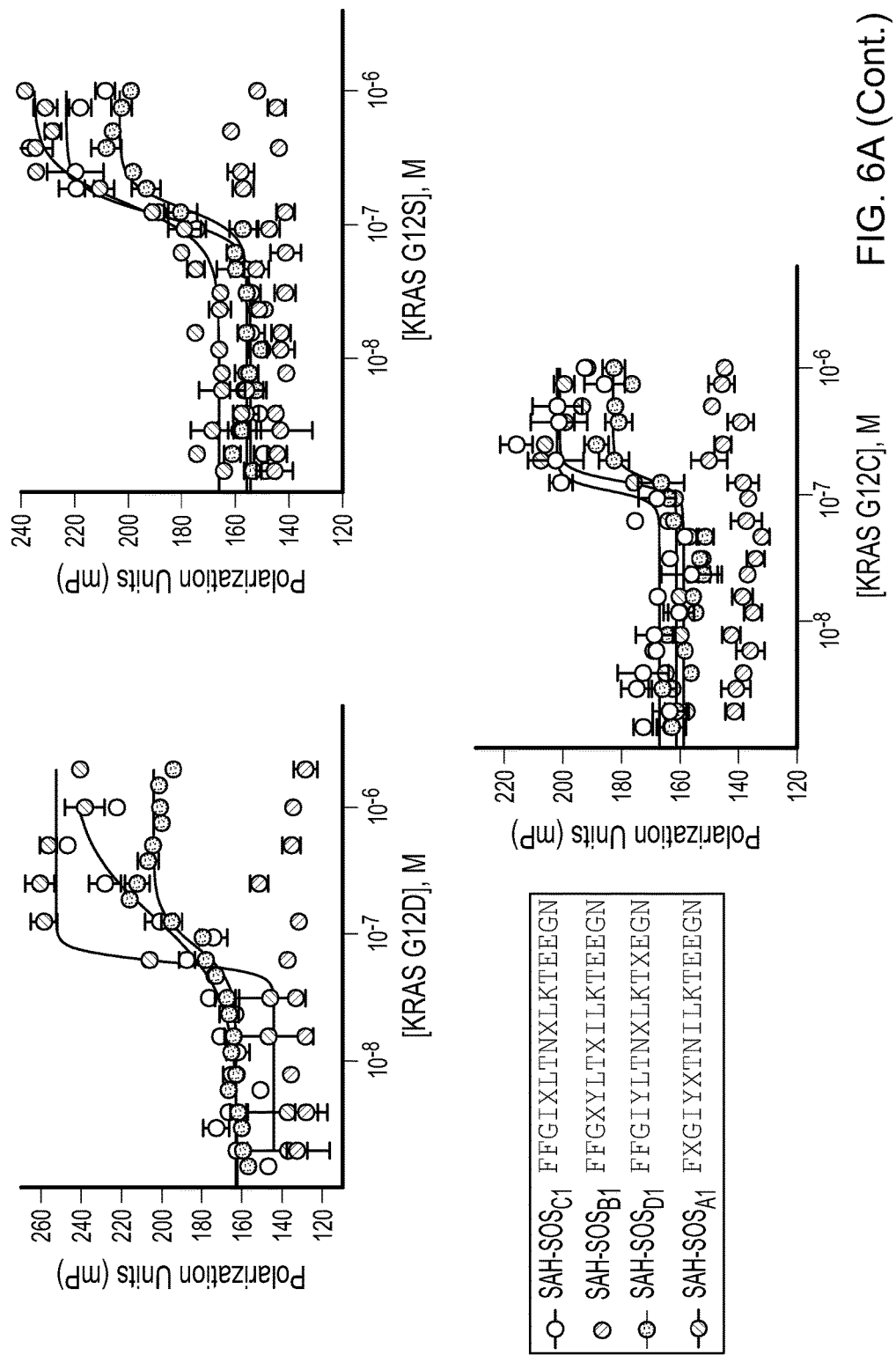

FIGS. 6A and B depict the results of a study demonstrating that SAH-SOS peptides bind with high affinity to recombinant KRAS proteins bearing point mutations frequently observed in human cancers (SEQ ID Nos: 16, 122 19 and 12, respectively, in order of appearance).

Figure 7A:
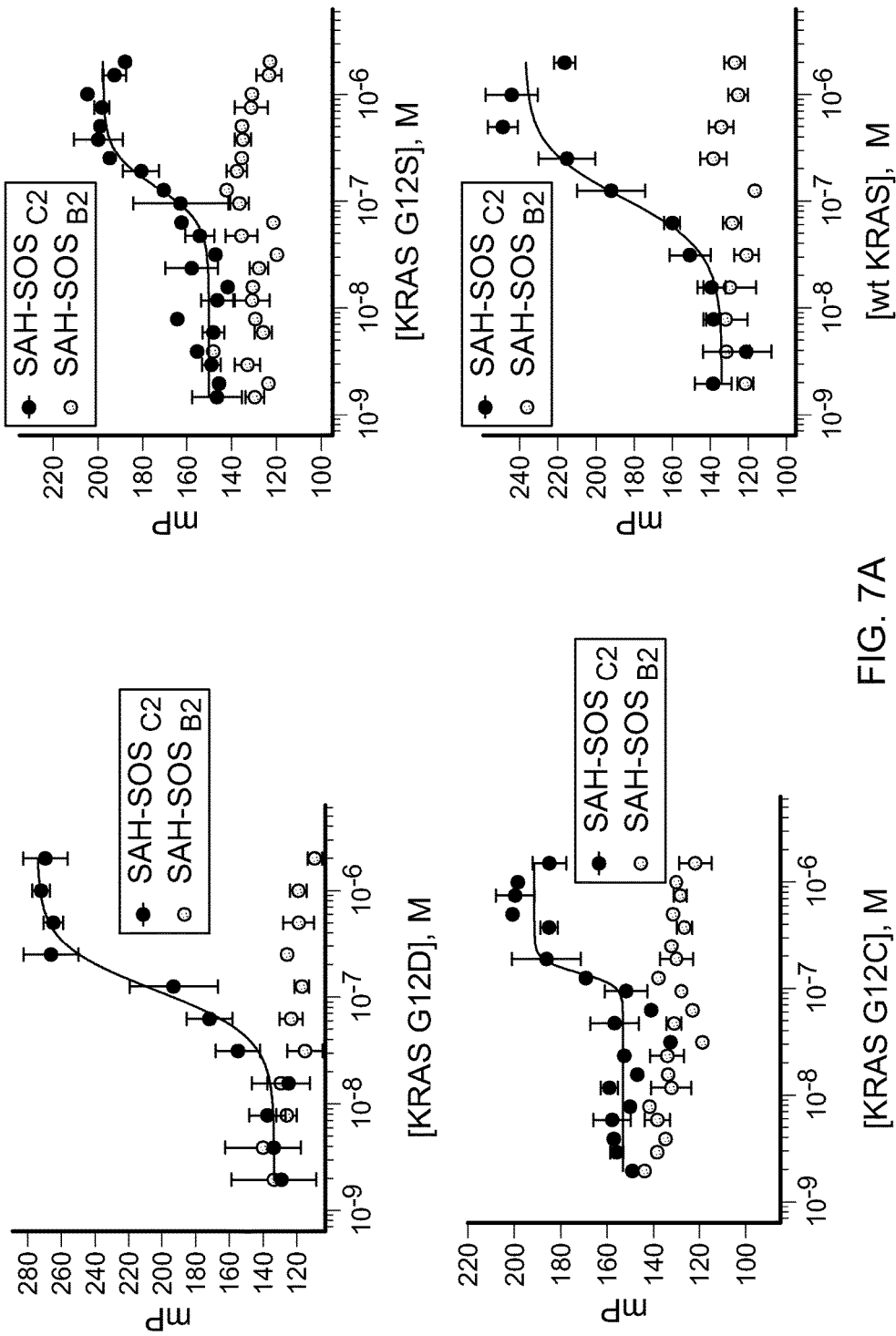
Figures 7A, 7B:
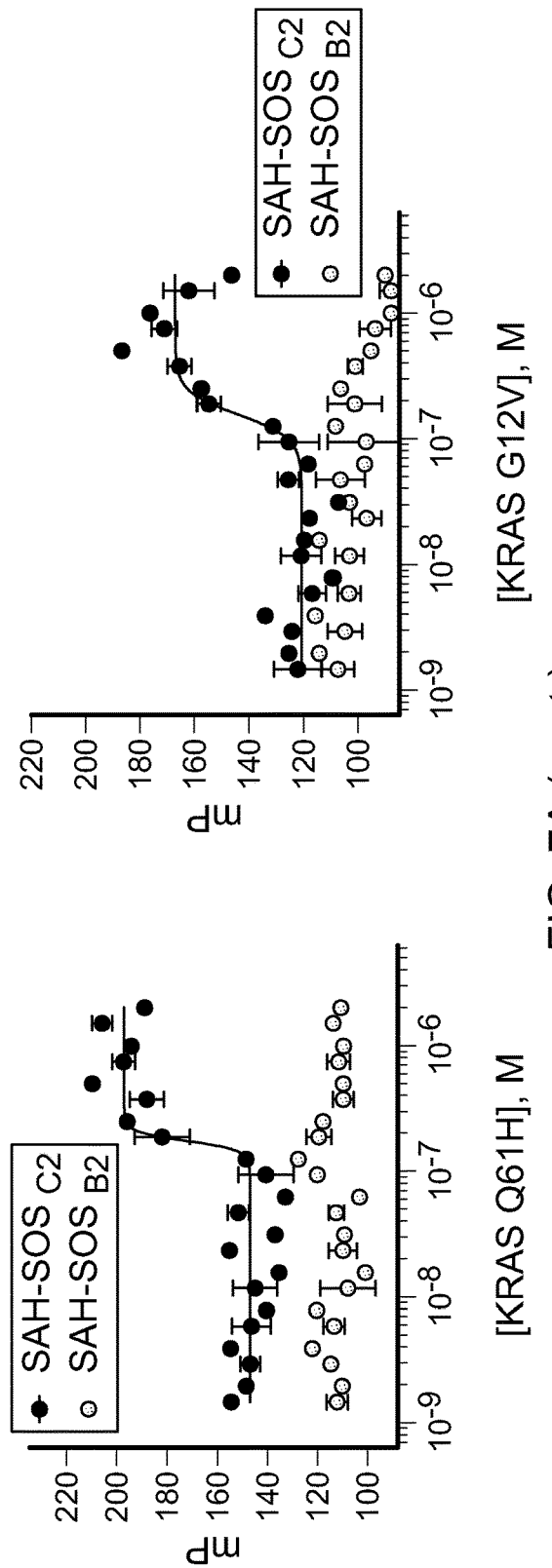
Figure 8D:
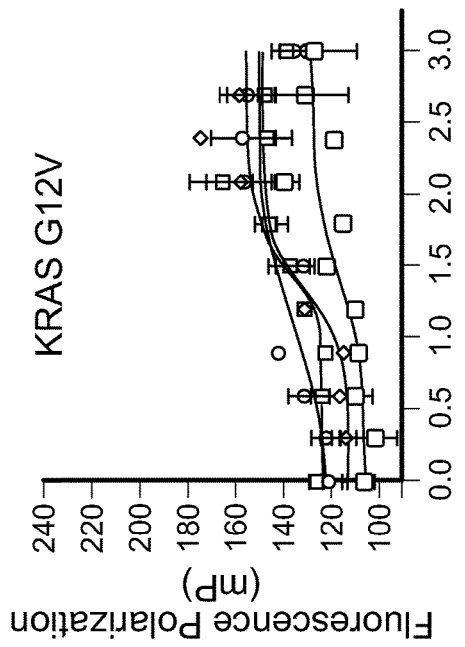
Figure 8F:
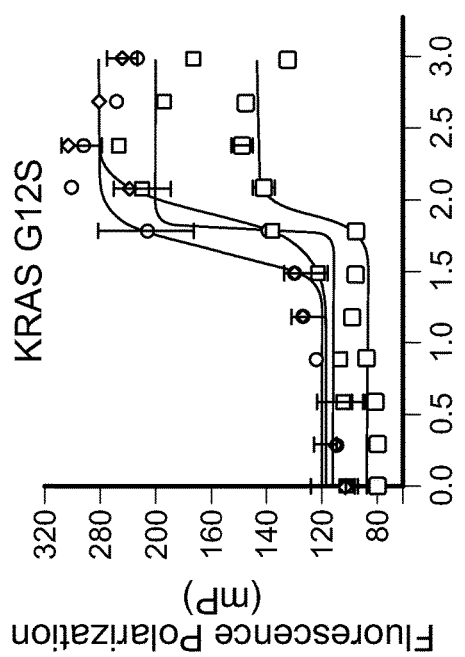
Figure 8E:
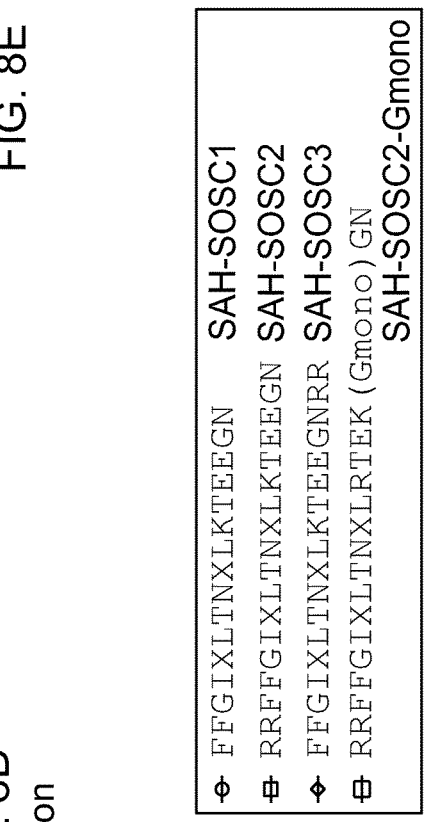

FIGS. 7A and B demonstrates that SAH-SOS peptides bind with high affinity to oncogenic KRAS mutant variants, whereas the negative control construct shows no interaction, as performed with independent, biological-replicate preparations of KRAS proteins.

FIGS. 8A-8F depict the binding interaction as detected by a fluorescence polarization assay between exemplary SAH-SOS peptides and wild-type and mutant KRAS proteins, including the SAH-SOS-Gmono stapled peptide that is further derivatized via its side chain (SEQ ID Nos: 16-18 and 123, respectively, in order of appearance).

Figure 9:
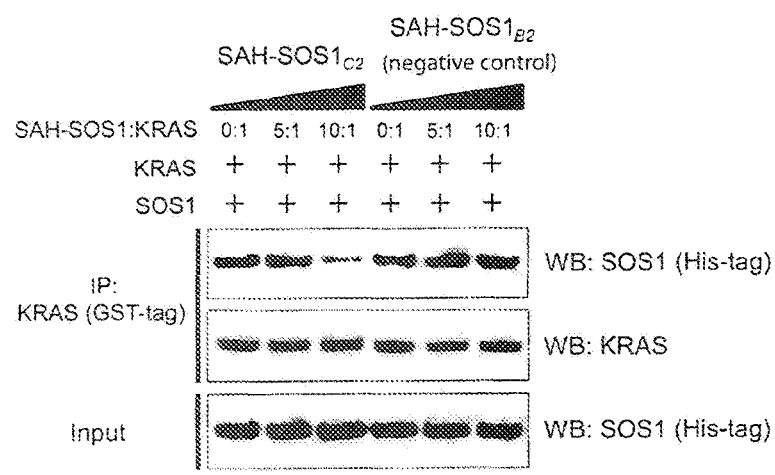

FIG. 9 demonstrates that a SAH-SOS binding peptide is capable of disrupting the protein-protein interaction between KRAS and its activator protein SOS1, whereas the non-binding SAH-SOS peptide control has no such activity.

FIG. 10 depicts the results of a study demonstrating that SAH-SOS peptides inhibit the GTP exchange activity of KRAS (SEQ ID NOS 17-18, respectively, in order of appearance).

FIGS. 11A-D depict the results of a study demonstrating that SAH-SOS peptides, but not the negative control construct are capable of disrupting nucleotide association with wild-type and mutant KRAS proteins.

Figure 12A:
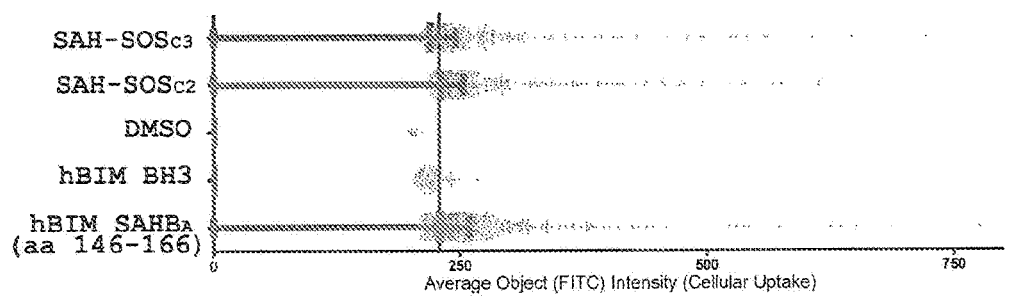
Figure 12B:
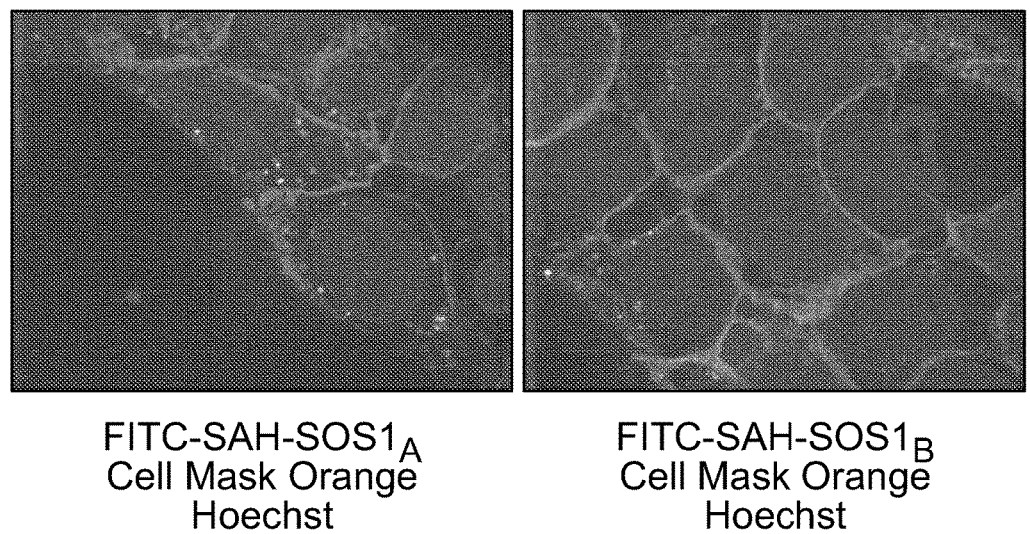
Figure 12C:
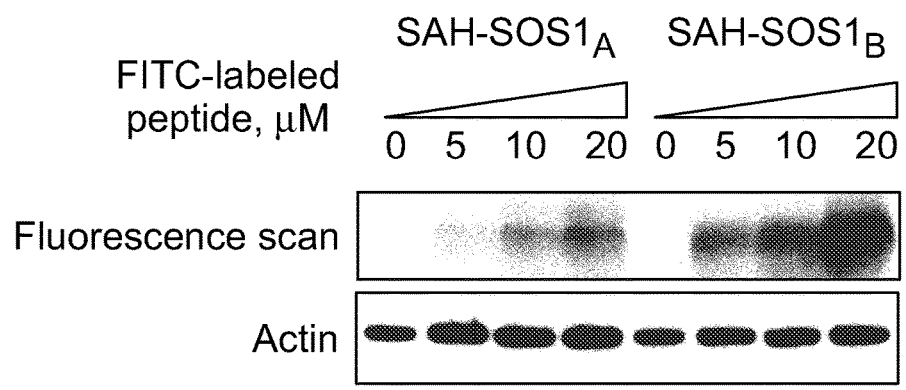

FIGS. 12A-C depict the results of a study demonstrating the efficient cellular penetrance of SAH-SOS C2, SAH-SOS C3 and SAH-SOS B2 (negative control) and C3 peptides.

Figure 13A:
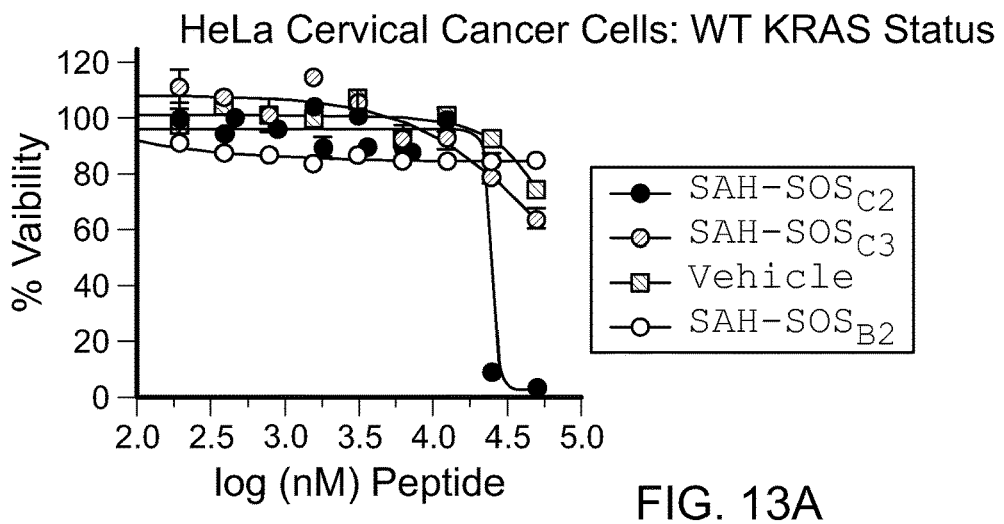
Figure 13B:
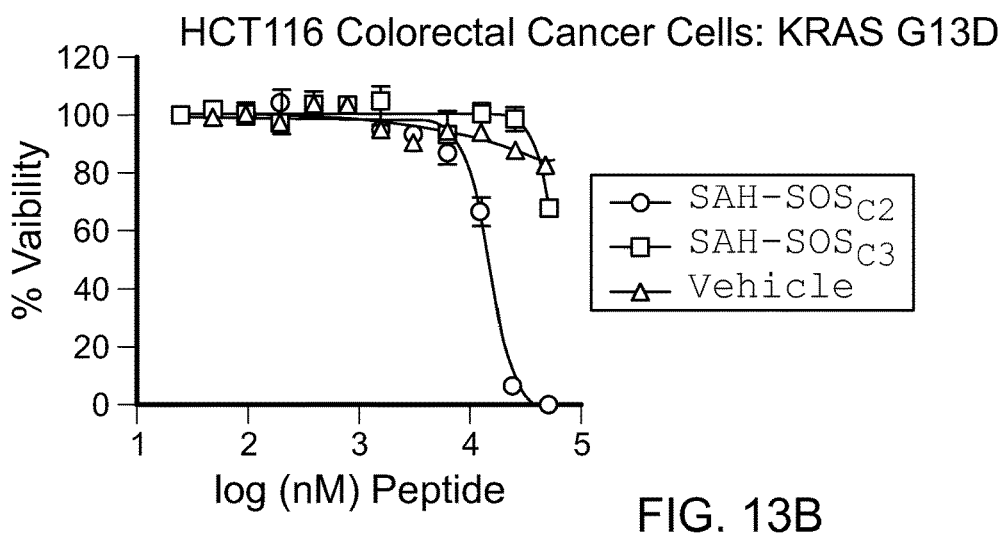
Figure 13C:
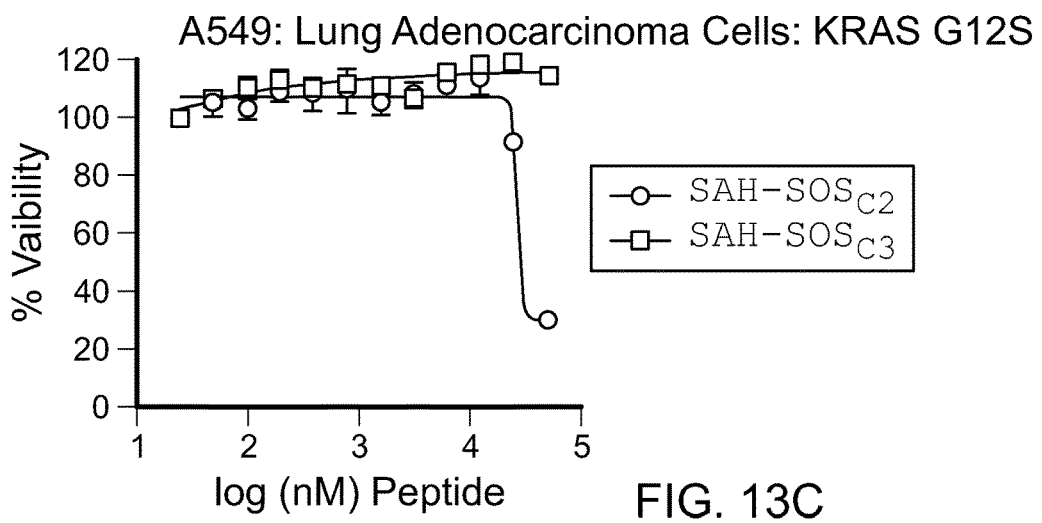

FIGS. 13A-C depicts the results of a study demonstrating that SAH-SOS peptides inhibit the viability of RAS-driven cancer cells.

Figure 14:
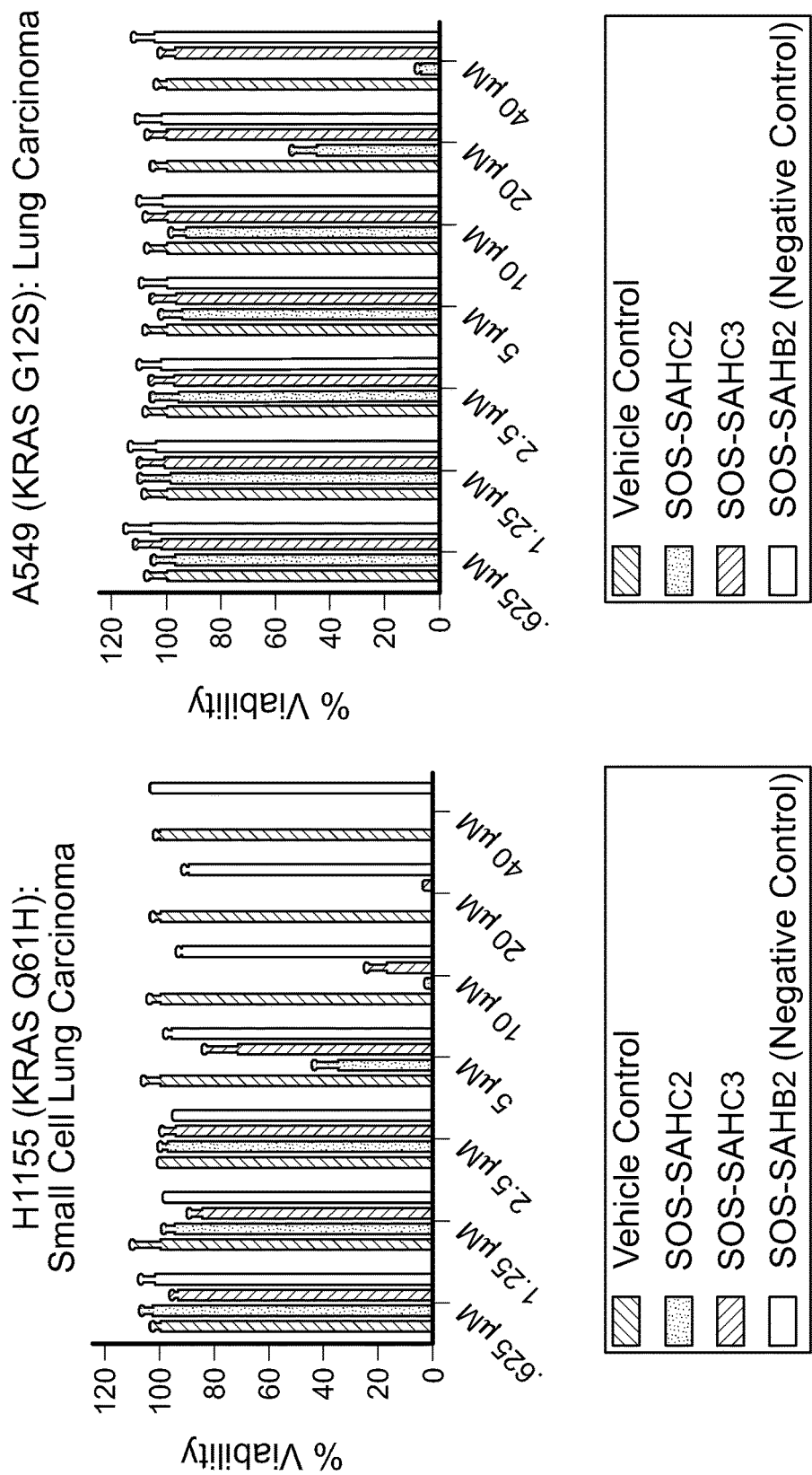
Figure 14:
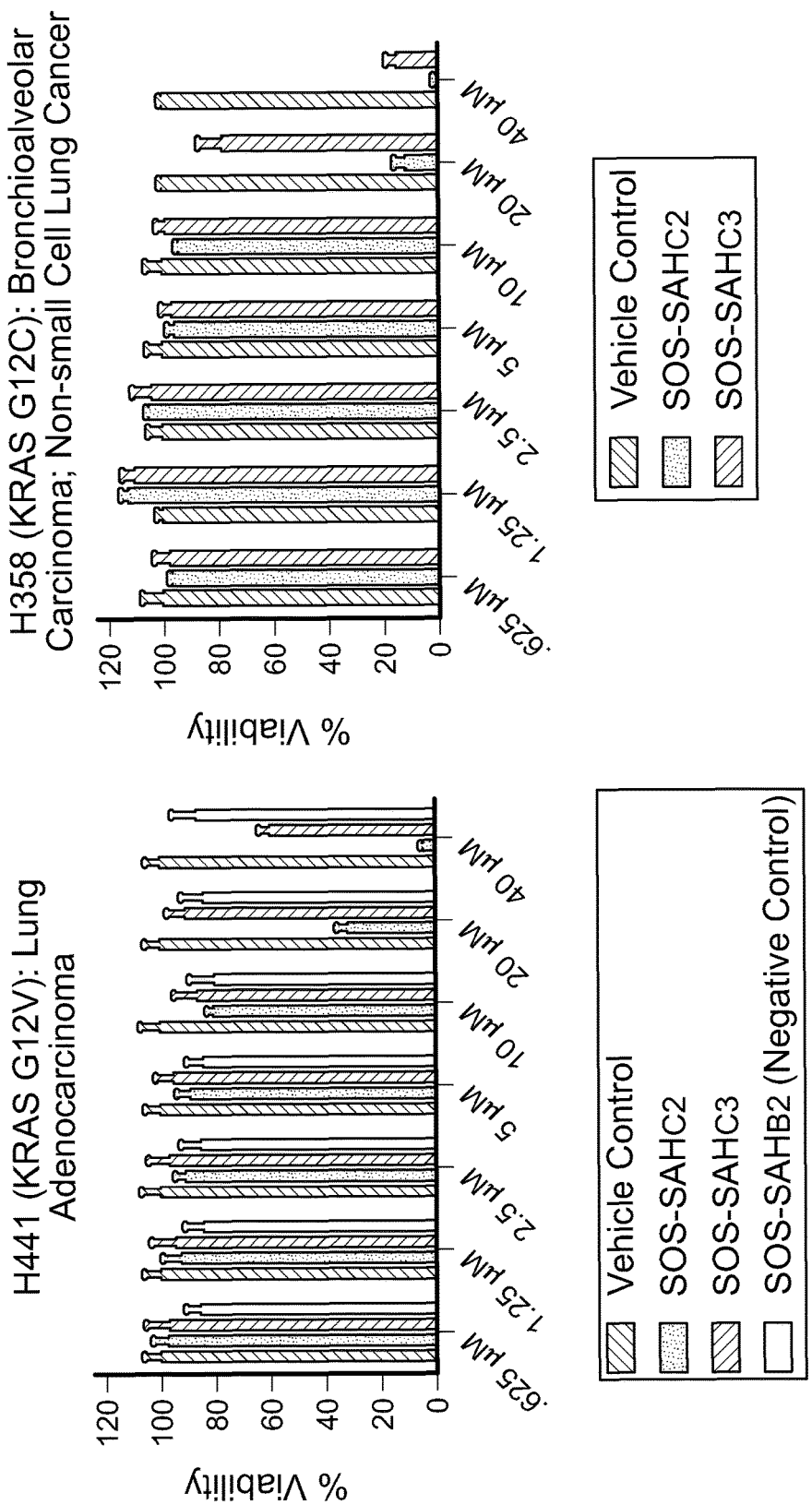
Figure 14:
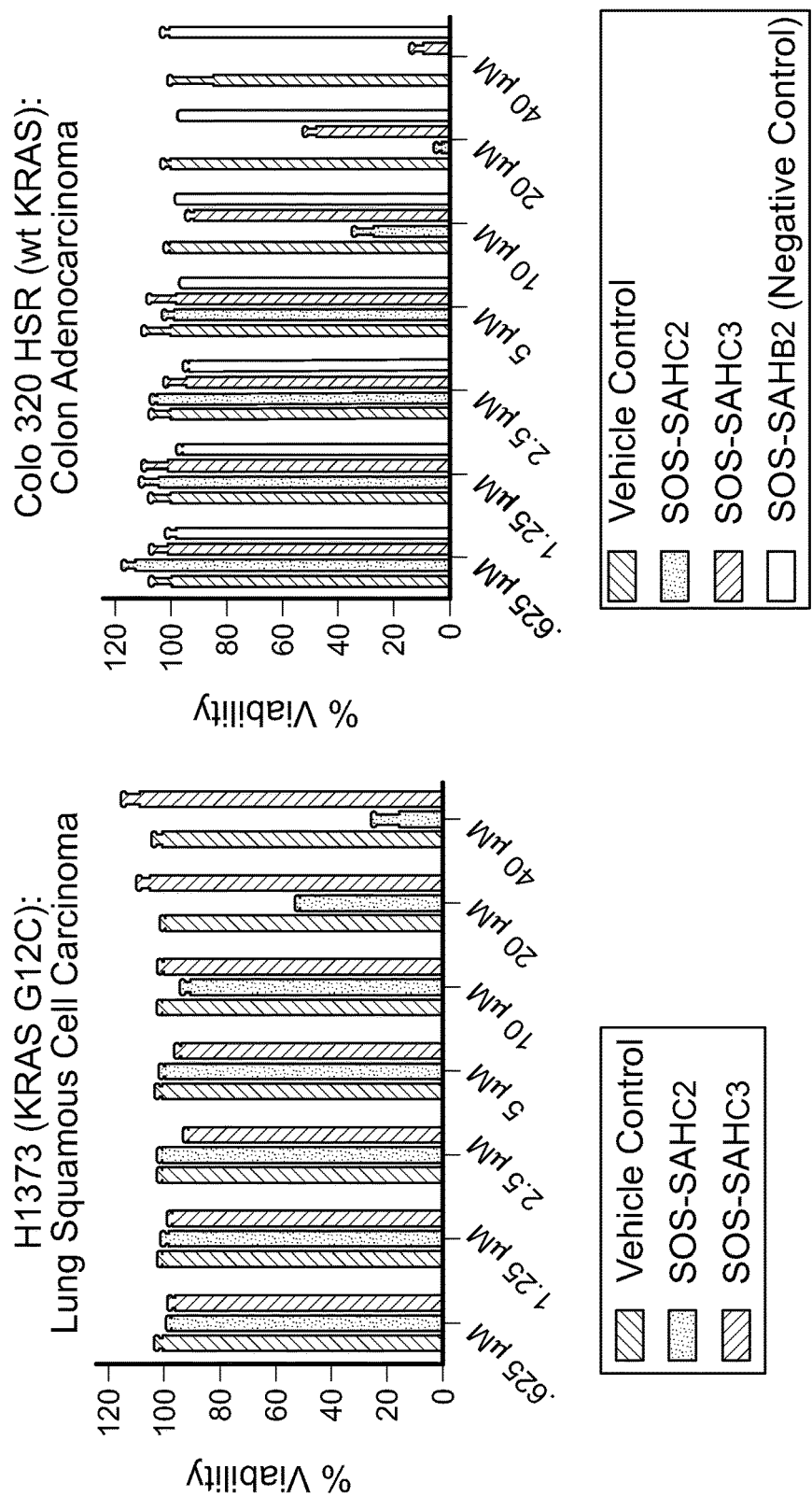
Figure 14:
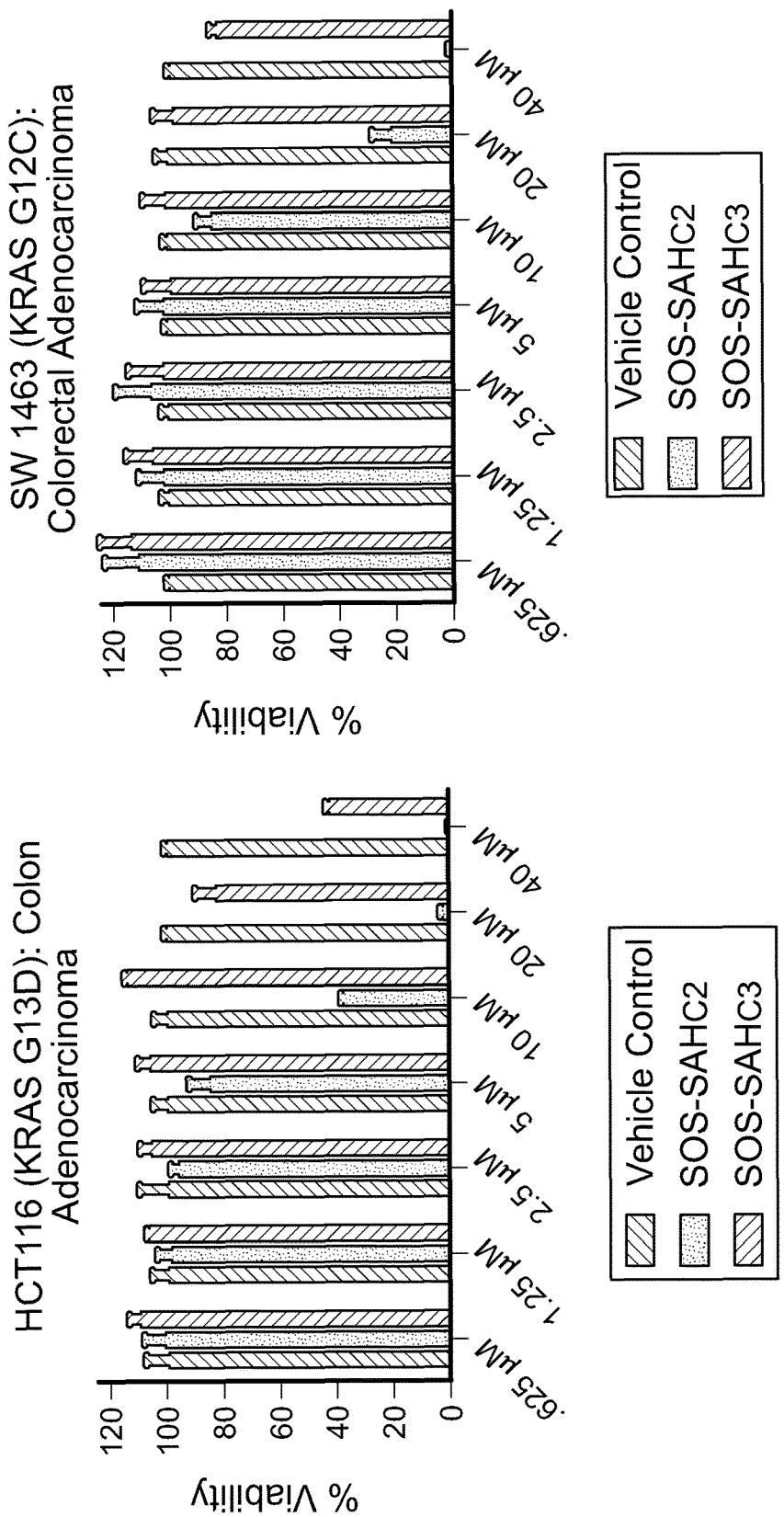
Figure 14:
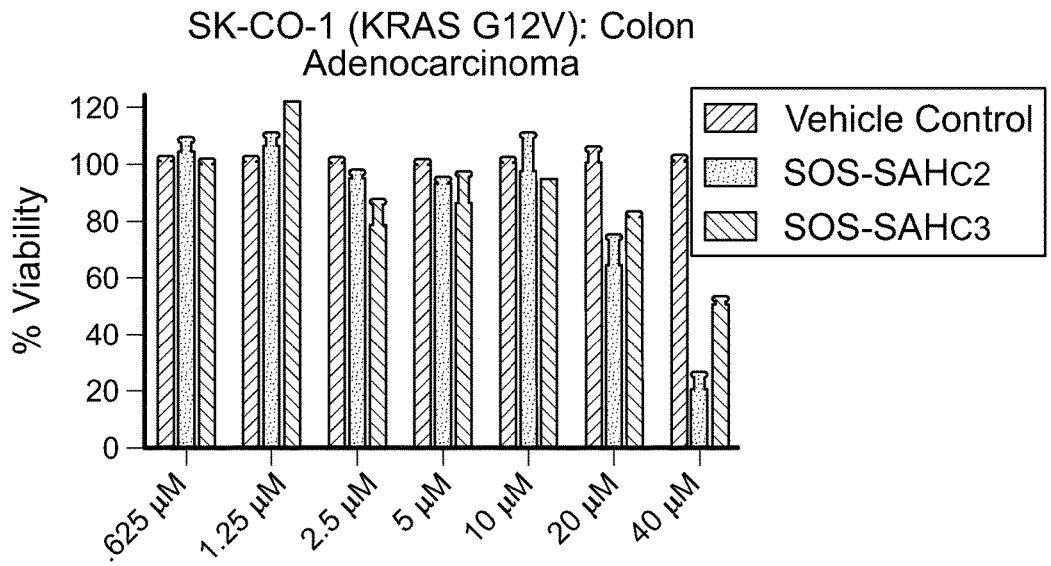

FIG. 14 depicts the susceptibility of a diversity of cancer cell lines, including pancreatic, lung, and colon cancers, to treatment with bioactive SAH-SOS peptides.

Figure 15A:
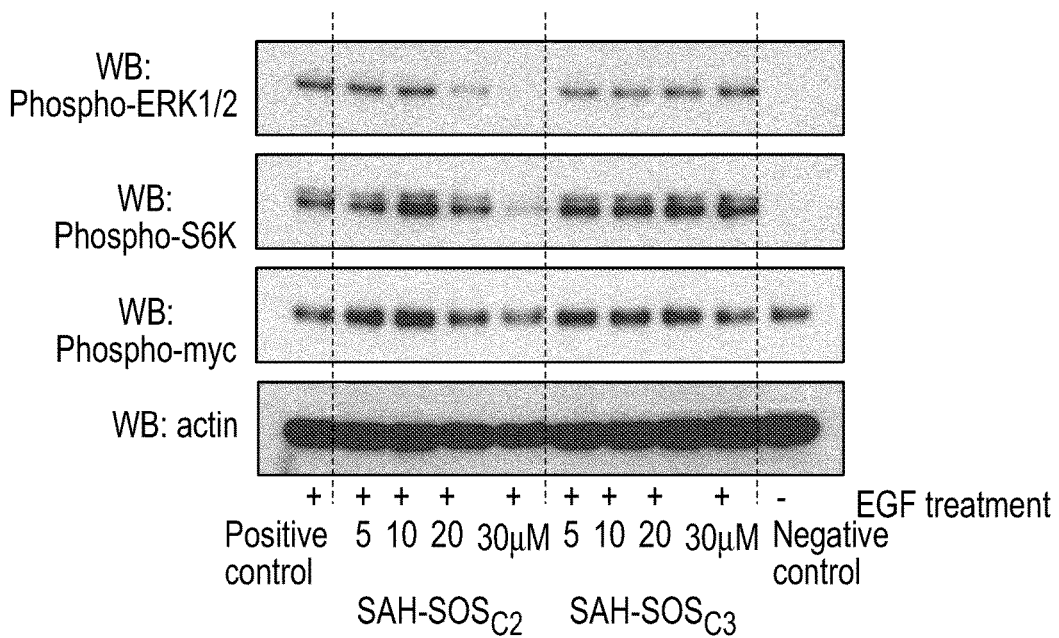

FIGS. 15A and B depict the results of a study demonstrating that the cytotoxicity of SAH-SOS peptides correlates with inhibition of KRAS signaling in the cancer cell lines HeLa and Panc 10.05.

Figure 16:
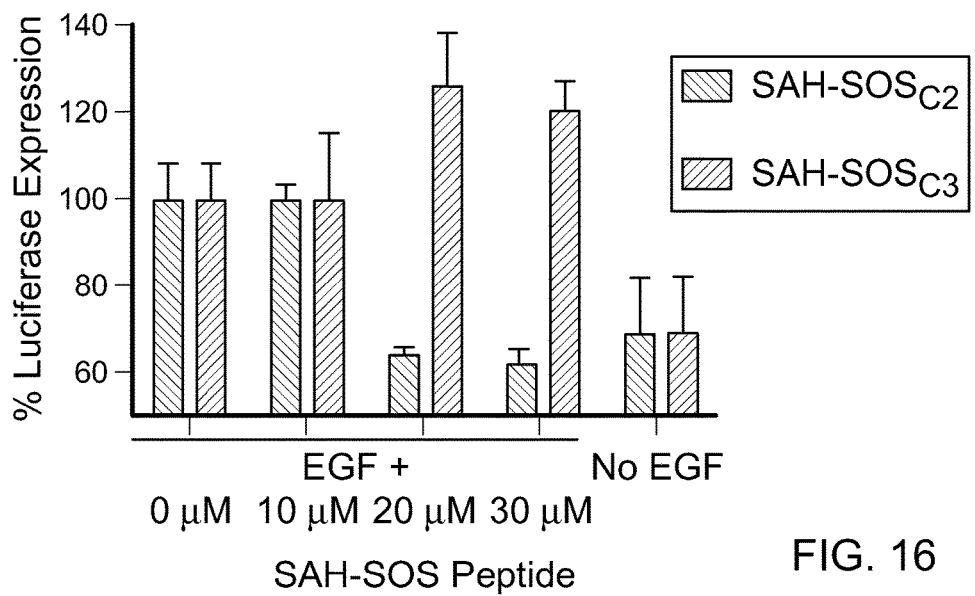

FIG. 16 depicts the results of a study demonstrating SAH-SOS$_{C2}$ inhibits Myc-driven expression in response to EGF stimulation.

Figure 17:
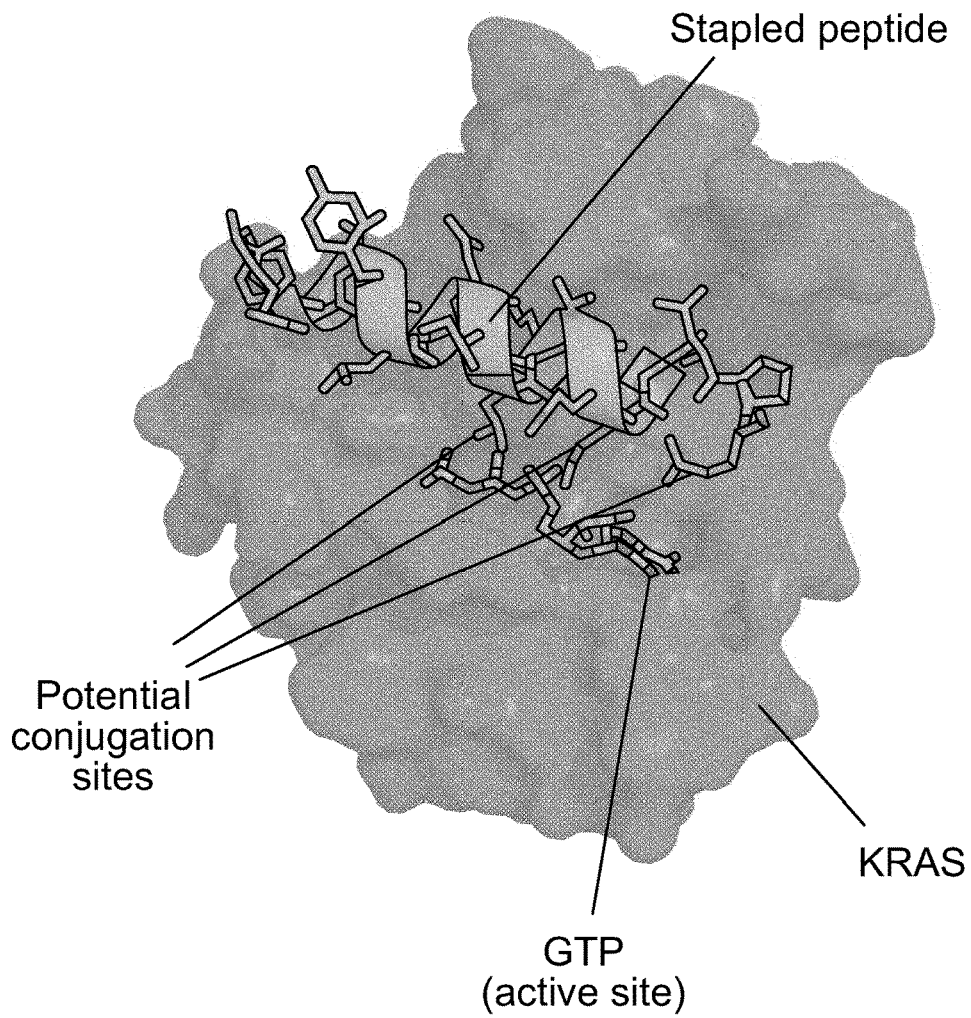

FIG. 17 depicts the derivatization of SAH-SOS peptides to jointly target the SOS1 and GTP binding sites on KRAS (SEQ ID Nos: 124-127, 123 and 128-131), respectively, in order of appearance). The sequences not found in Tables 2 or 3 are as follows: RRFFGIXLTNXLRTEKGN (SEQ ID NO: 123); RRFFGIXLTNXKKTEKGN (SEQ ID NO: 124); RRFFGIXLTNXK(Gmono)RTEEGN (SEQ ID NO: 125); RRFFGIXLTNXKRTEEGN (SEQ ID NO:126); RRFFGIXLTNXLKTEKGN (SEQ ID NO:127); RRFFGIXLTNXLRTEK(G-GMONO)GN (SEQ ID NO: 128); RRFFGIXLTNXKKTEKGNPK (SEQ ID NO:129); RRFFGIXLTNXLRTEEGNPK(Gmono) (SEQ ID NO:130); RRFFGIXLTNXLRTEEGNPK(G-Gmono) (SEQ ID NO:131).

Figure 18:
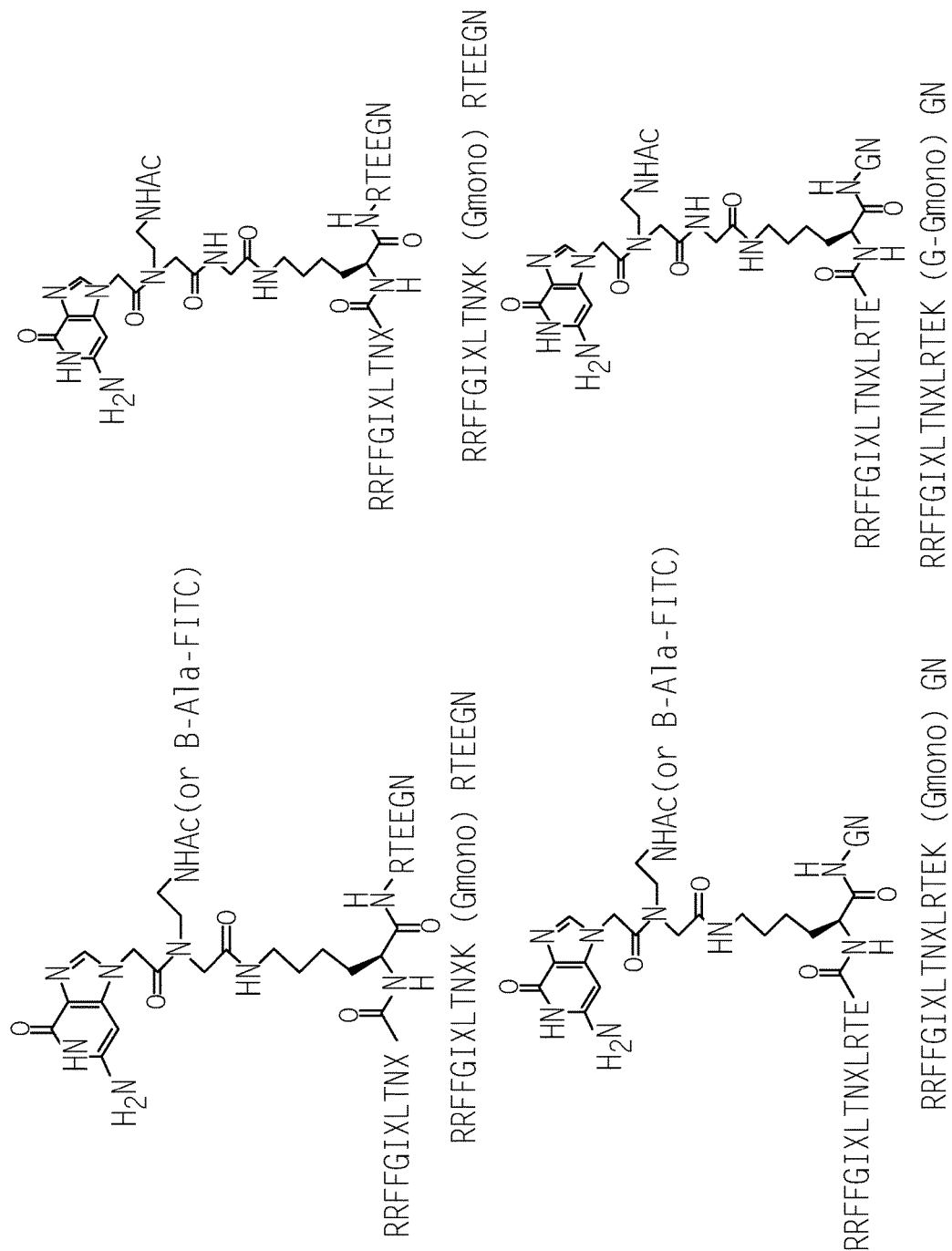
Figure 18:
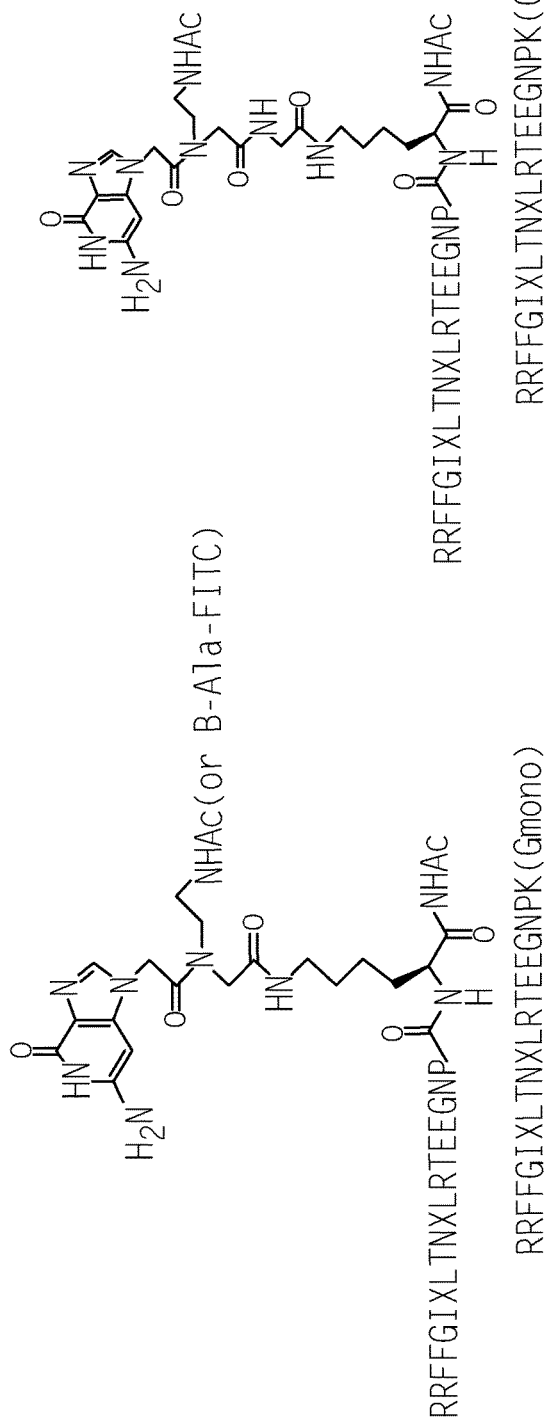

FIG. 18 depicts the structure of various SAH-SOS peptides containing guanine peptide-nucleic acid monomers (SEQ ID Nos: 125-126, 123, 128 and 130-131, respectively, in order of appearance). The sequences not found in Tables 2 or 3 are as follows: RRFFGIXLTNXLRTEKGN (SEQ ID NO: 123); RRFFGIXLTNXK(Gmono)RTEEGN (SEQ ID NO: 125); RRFFGIXLTNXKRTEEGN (SEQ ID NO:126); (G-GMONO)GN (SEQ ID NO: 128); RRFFGIXLTNXLR-TEEGNPK(Gmono) (SEQ ID NO:130); RRFFGIXLTNX-LRTEEGNPK(G-Gmono) (SEQ ID NO:131).

Figure 19:
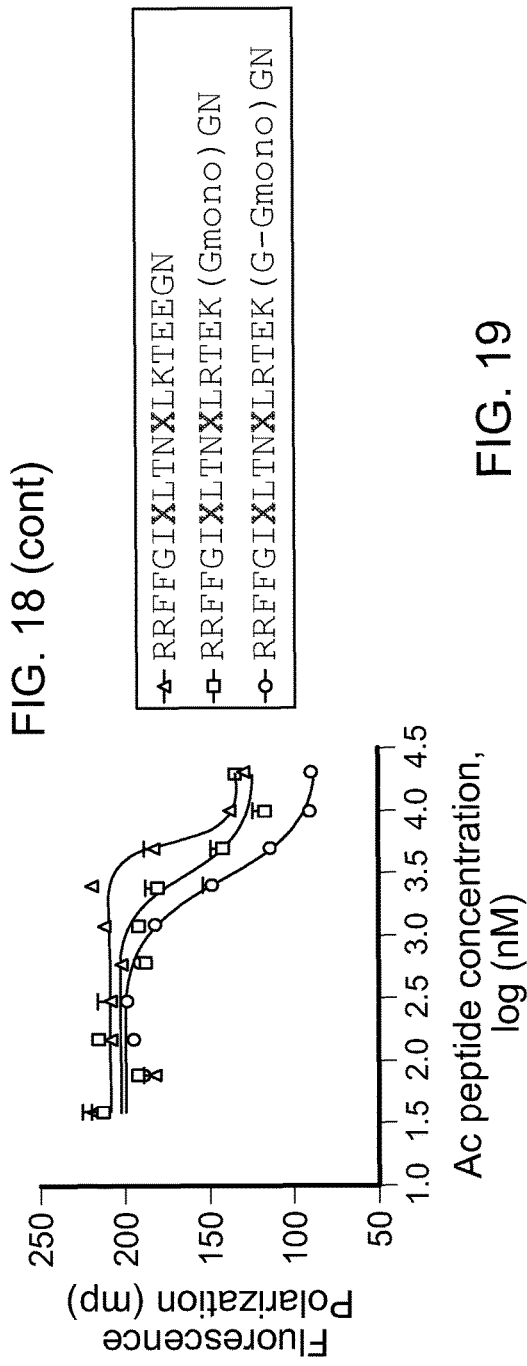

FIG. 19 depicts the results of studies demonstrating the increased KRAS binding affinity of guanine peptide-nucleic acid monomer-derivatized SAH-SOS peptides (SEQ ID Nos: 17, 123 and 128, respectively, in order of appearance). The sequences not found in Tables 2 or 3 are as follows: RRFFGIXLTNXLRTEKGN (SEQ ID NO: 123); and (G-GMONO)GN (SEQ ID NO: 128).

Figure 20A:
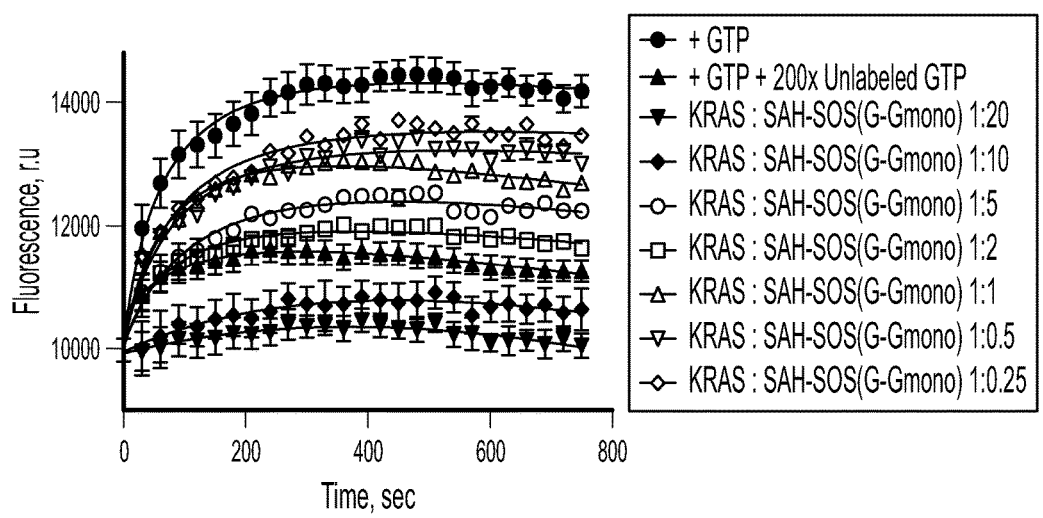
Figure 20B:
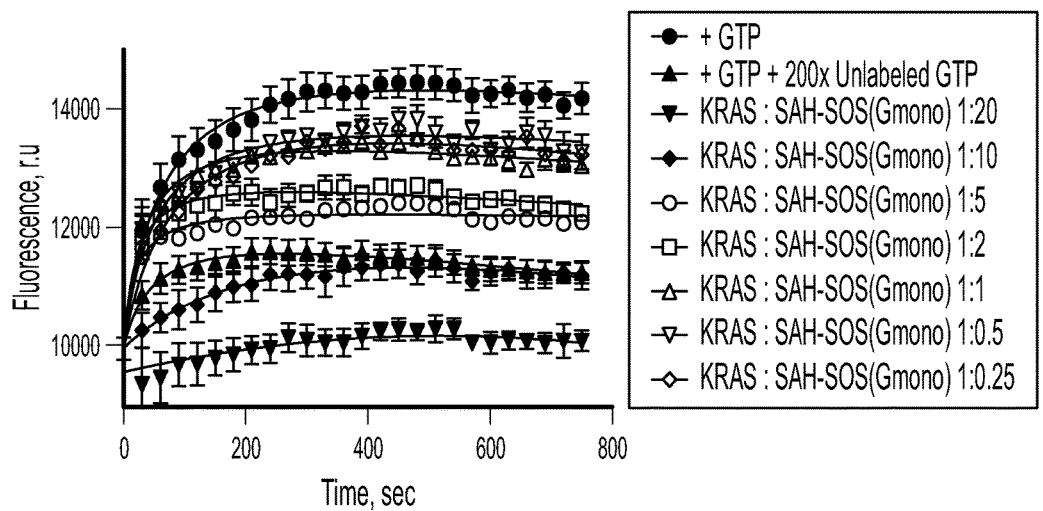

FIGS. 20A and B demonstrate that guanine peptide-nucleic acid monomer-derivatized SAH-SOS peptides are potent inhibitors of GTP loading onto KRAS G12D mutant protein.

Figure 21:
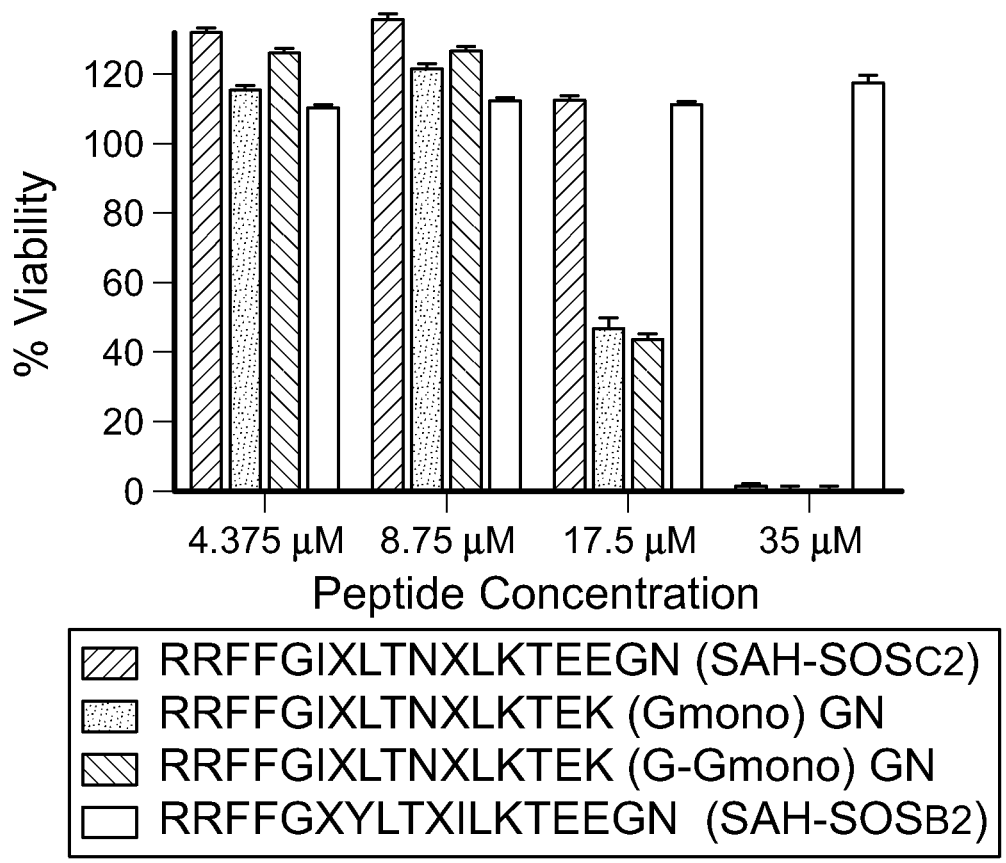

FIG. 21 depicts the results of studies demonstrating the increased cytotoxicity of guanine peptide-nucleic acid monomer-derivatized SAH-SOS peptides in KRAS-driven cancer cells (SEQ ID Nos: 17, 123, 128 and 15, respectively, in order of appearance). The sequences not found in Tables 2 or 3 are as follows: RRFFGIXLTNXLRTEKGN (SEQ ID NO: 123); and (G-GMONO)GN (SEQ ID NO: 128).

Figure 22:
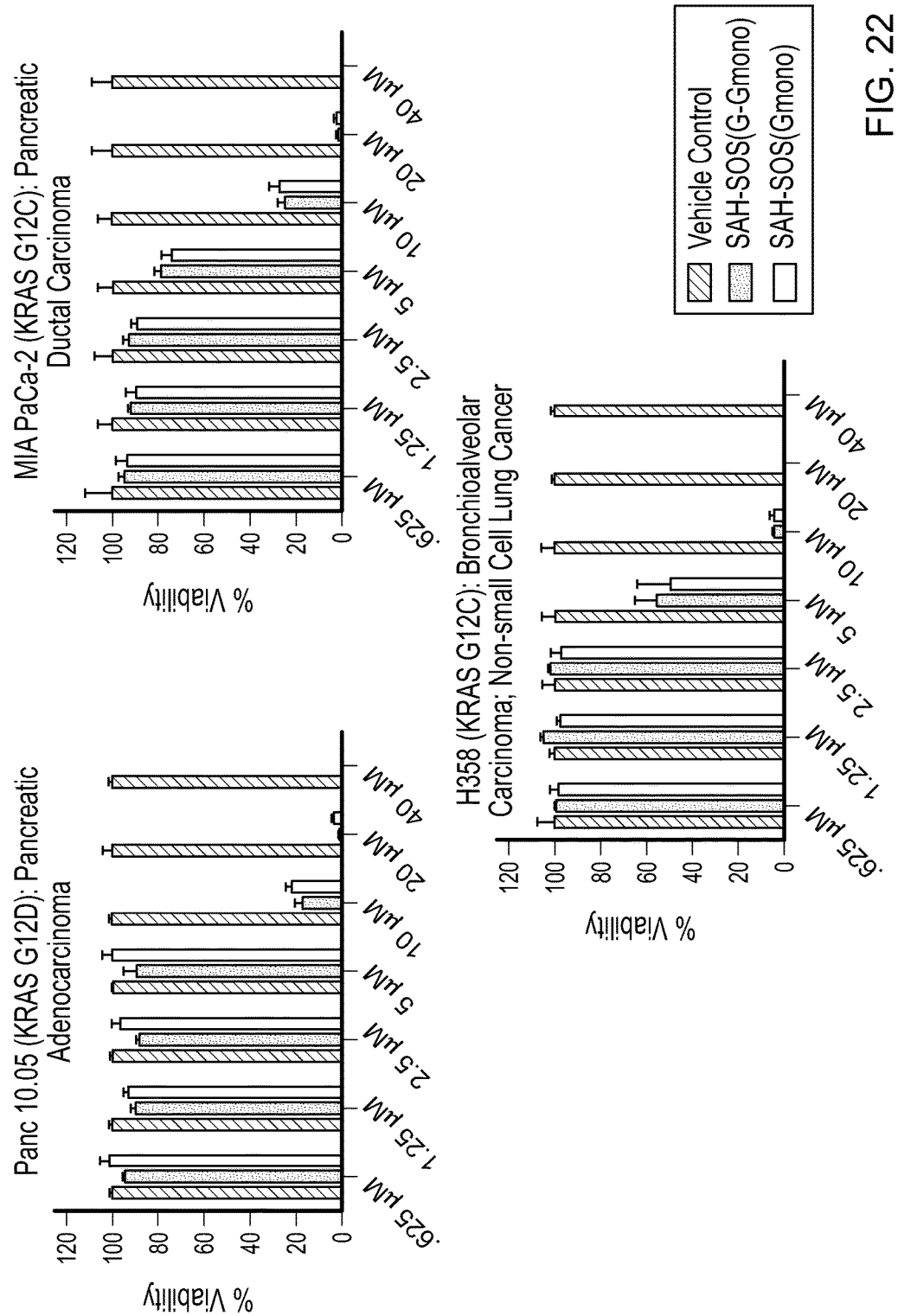
Figure 22:
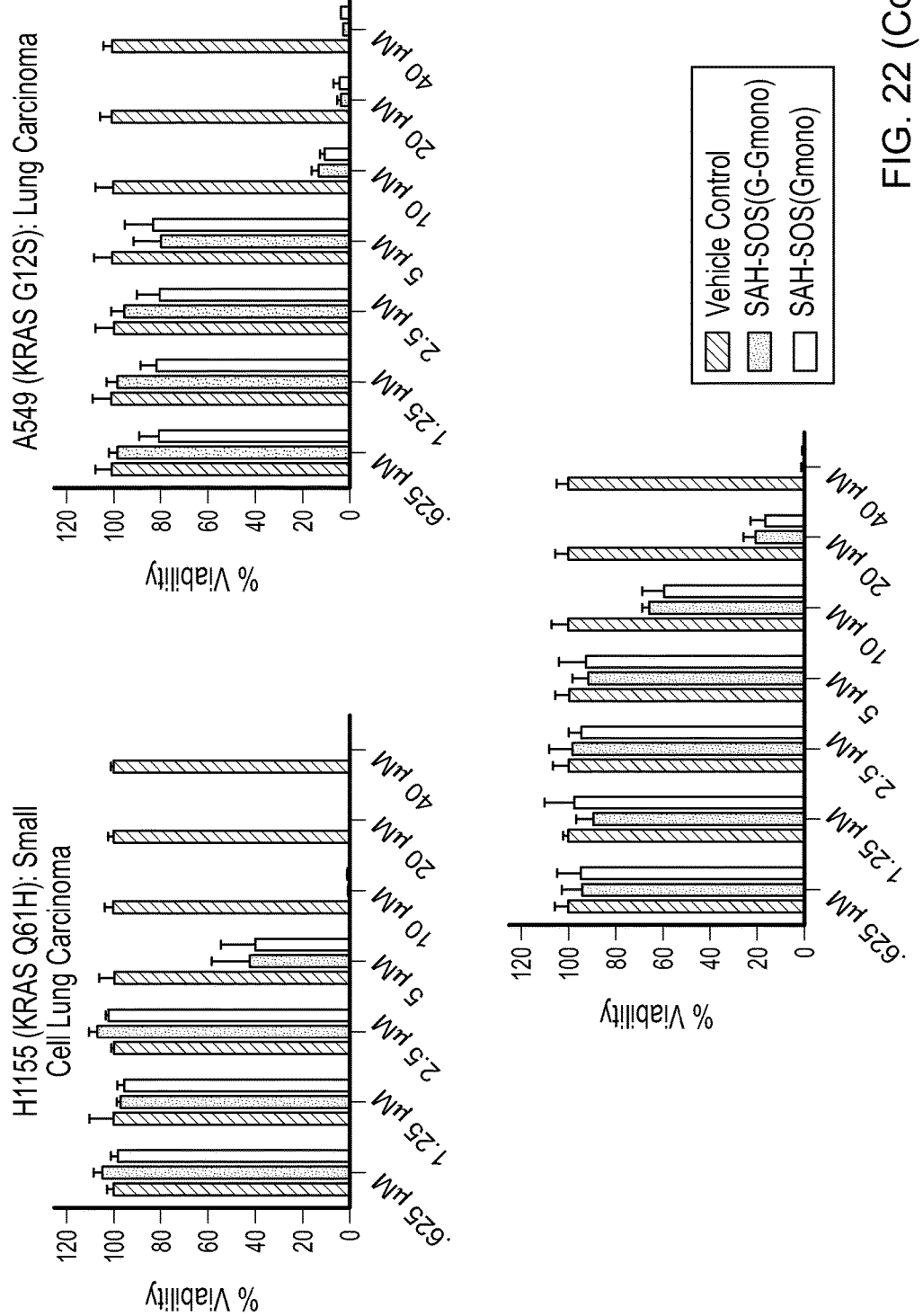

FIG. 22 provides further evidence of the anti-tumor activity of guanine peptide-nucleic acid monomer-derivatized SAH-SOS peptides against a variety of cancer cell lines harboring KRAS mutations, including pancreatic and lung cancer subtypes.

FIG. 23 is a table depicting various stapled peptides (Table 1). Sequence disclosed as SEQ ID NO: 2.

DETAILED DESCRIPTION

Stabilized Peptides

The present disclosure provides structurally stabilized peptides related to portions or fragments of SOS1 (referred to at times as stabilized α-helices of SOS1 or SAH-SOS1) comprising at least two modified amino acids joined by an internal (intramolecular) cross-link (or staple), wherein the at least two amino acids are separated by 2, 3, or, 6 amino acids. Stabilized peptides herein include stapled and/or stitched peptides.

Amino acids are the building blocks of the peptides herein. The term "amino acid" refers to a molecule containing both an amino group and a carboxyl group as well as a side chain. Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnnatural beta-amino acids. Amino acids used in the construction of peptides of the present invention can be prepared by organic synthesis, or obtained by other routes, such as, for example, degradation of or isolation from a natural source.

There are many known unnatural amino acids any of which may be included in the peptides of the present invention. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclo-propanecarboxylic acid, 1-amino-2-phenyl-cyclopropan-ecarboxylic acid, 1-amino-cyclobutanecarboxylic acid, 4-amino-cyclopentenecarboxylic acid, 3-amino-cyclo-hexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C$_6$H$_5$; —CF$_3$; —CN; -halo; —NO2; CH$_3$), disubstituted phenyl-alanines, substituted tyrosines (e.g., further substituted with -Q=O)C$_6$H$_5$; —CF$_3$; —CN; -halo; —NO$_2$; CH$_3$), and sta-tine. Additionally, amino acids can be derivatized to include amino acid residues that are hydroxylated, phosphorylated, sulfonated, acylated, and glycosylated, to name a few.

A "peptide" or "polypeptide" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. In some instances, peptides can include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof "Dipeptide" refers to two covalently linked amino acids.

In some instances, peptides can include (e.g., comprise, consist essentially of, or consist of) at least seven (e.g., 7, 8, 9, 10, 11, 12, 13, 14, 15, 16, 17, 18, 19, 20, 21, 22) contiguous amino acids of: the sequence FFGIYLTNILK-TEEGN (SEQ ID NO:2); the sequence FFGIYLTNILK-TEEGNRR (SEQ ID NO:3) the sequence RRFFGIYLT-NILKTEEGN (SEQ ID NO:4); the sequence FFGIYXTNILKTEEGNPELVRR (SEQ ID NO:5); the sequence RRFFGIYLTNILKTEEGNPELV (SEQ ID NO:6); the sequence FFGIYLTNILKTEEGNPELV (SEQ ID NO:7); the sequence FFGIYLTNILKTEEGNR (SEQ ID NO:8) the sequence RFFGIYLTNILKTEEGN (SEQ ID NO:9); the sequence FFGIYXTNILKTEEGNPELVR (SEQ ID NO:10); and the sequence RFFGIYLTNILKTEEGN-PELV (SEQ ID NO:11), wherein the peptide has a reinforced or stabilized alpha helical secondary structure (e.g., wherein the peptide includes at least one internal crosslink).

In some instances, the peptide has or can be induced to have alpha helical secondary structure.

In some cases the peptide is a modified peptide that includes 1, 2, or 3 conservative substitutions and/or 1 or 2 non-conservative substitutions and/or 1 or 2 insertions or deletions compared to the sequence FFGIYLTNILKTEEGN (SEQ ID NO:2); the sequence FFGIYLTNILKTEEGNRR (SEQ ID NO:3) the sequence RRFFGIYLTNILKTEEGN (SEQ ID NO:4); the sequence FFGIYXTNILKTEEGNPEL-VRR (SEQ ID NO:5); the sequence RRFFGIYLTNILK-TEEGNPELV (SEQ ID NO:6); the sequence FFGIYLT-NILKTEEGNPELV (SEQ ID NO:7); the sequence FFGIYLTNILKTEEGNR (SEQ ID NO:8) the sequence RFFGIYLTNILKTEEGN (SEQ ID NO:9); the sequence FFGIYXTNILKTEEGNPELVR (SEQ ID NO:10); and the sequence RFFGIYLTNILKTEEGNPELV (SEQ ID NO:11), wherein the peptide has a reinforced or stabilized alpha helical secondary structure (e.g., wherein the peptide includes at least one internal crosslink) and wherein the percent identity calculation includes the cross-linked amino acids and the cross-linked amino acids are considered non-conservative substitutions. In some cases the internal cross-link replaces the side chains of two amino acids separated by 3 amino acids. In some cases the internal cross-link replaces the side chains of two amino acids separated by 6 amino acids. In some cases there are two internal cross-links, each replacing the side chains of a pair of amino acids separated by 3 amino acids and each cross-link being on essentially the same face of the resulting essentially alpha-helical peptide.

In some instances, stabilized peptides can have at least 80% (e.g., 80%, 85%, 90%, 95%, 98%, 99%, 99.5%, or 100%) identity one of SEQ ID NOs: 2-11 or can include one of SEQ ID NOs:2-11 with one or more (e.g., 1, 2, 3, 4, 5, 6, 7, 8, 9, 10, 11, 12, 13, 14, 15, 16, 17, 18, preferably 1-2, 1-3, 1-4 or 1-5) conservative amino acid substitutions. In some cases the side chain of an amino acid is substituted by Formula I. In some cases, the stabilized peptide has the sequence of one SEQ ID NOs: 1-11 with one or two staples (e.g., one staple between two amino acids separated by 3 (or 6) amino acids or two staples each between two amino acids that are separated by 3 (or 6) amino acids). In addition, 1, 2, 3, 4 or 5 of the amino acids (whose side chains are not replaced with a staple) in this stabilized peptide can be replaced by a conservative substitution.

In some cases the staple is between $E_0$ and $B_1$ or $B_1$ and $F_1$ or $A_0$ and $A_1$ or $B_1$ and $B_1$ or $C_1$ and $G_1$ or $F_1$ and an amino acid immediately C-terminal to $B_2$ (using the sequence of FIG. 23). Preferably the staple is not between $B_0$ and $F_0$ or $D_0$ and $A_1$ (using the sequence of FIG. 23).

The "interacting face" of the peptides herein includes those amino acid residues of the alpha helix that interact (e.g., interact specifically or bind specifically) with are shown in FIG. 2 Methods for detecting any reduction in binding can include comparing binding affinity following conservative amino acid substitution, wherein any amino acid substitution that reduces (e.g., substantially reduces) binding are not conservative amino acid substitutions. In some embodiments, substantially reduced binding can include binding that is 10%, 20%, 30%, 40%, 50%, 60%, 70%, 80%, 90%, 95%, 98%, 99%, or 100% less than binding of the unmodified stabilized peptide to KRAS. Methods for assessing interaction between a stabilized SOS1 peptide and KRAS are disclosed herein.

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

In some instances, amino acid sequences of any peptide disclosed herein can be varied as long as the residues of the interacting face are identical to those shown for $A_0$, $D_0$, $A_1$, $D_1$, $E_1$, and $A_2$ of SEQ ID NO:1, or are conservative substitutions thereof.

As disclosed above, peptides herein include at least two modified amino acids that together form an internal (intramolecular) cross-link (or staple), wherein the at least two modified amino acids are separated by: (A) two amino acids (i.e., i, i+3, shown in Table 1 (FIG. 23) as ◇), (B) three amino acid (i.e., i, i+4, shown in Table 1 (FIG. 23) as ○), or (C) six amino acids (i.e., i, i+7, shown in Table 1 (FIG. 23) as †).

In the case of a cross-link between i and i+3 the cross-link can be a C7 alkylene or alkenylene. In the case of a cross-between i and i+4 the cross-link can be a C8 alkylene or alkenylene. In the case of a cross-link between i and i+7 the cross-link can be a C11, C12 or C13 alkylene or alkenylene. When the cross-link is an alkenylene there can one or more double bonds.

In the case of a cross-link between i and i+3 the cross-link can be a C6, C7, or C8 alkyl or alkene (e.g., a C6 alkene having a single double bond). In the case of a cross-link between i and i+4 the cross-link can be a C8 alkyl or alkene. In the case of a cross-link between i and i+7 the cross-link can be a C11, C12 or C13 alkyl or alkene (e.g., a C11 alkene having a single double bond). When the cross-link is an alkene there can be one or more double bonds.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., J. Org. Chem., 66: 5291-5302, 2001; Angew et al., Chem. Int. Ed. 37:3281, 1994). As used herein, the term "peptide stapling," includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed in WO 2008121767 and in WO 2010/068684, which are both hereby incorporated by reference. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g, 1, 4 triazole or 1, 5 triazole) crosslinks can be used (Kawamoto et al. 2012 Journal of Medicinal Chemistry 55:1137; WO 2010/060112).

Stapling of a peptide using all-hydrocarbon cross-link has been shown to help maintain its native conformation and/or secondary structure, particularly under physiologically relevant conditions (Schafmiester et al., J. Am. Chem. Soc., 122:5891-5892, 2000; Walensky et al., Science, 305:1466-1470, 2004).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding uncrosslinked (e.g., "unstitched" or "unstapled") peptide.

Stabilized peptides herein include at least two internally cross-linked or stapled amino acids, wherein the at least two amino acids are separated by two (i.e., i, i+3, shown in Table 1 (FIG. 23), three (i.e., i, i+4, shown in Table 1), or six (i.e., i, i+7, shown in Table 1 (FIG. 23) amino acids. While at least two amino acids are required to support an internal cross-link (e.g., a staple), additional pairs of internally cross-linked amino acids can be included in a peptide, e.g., to support additional internal cross-links (e.g., staples). For example peptides can include 1, 2, 3, 4, 5, or more staples. Examples of peptide staples are illustrated in the figures. Cross-linked peptides (e.g., stapled and/or stitched peptides) are generally referred to herein as SAH peptides.

Figure 1D:
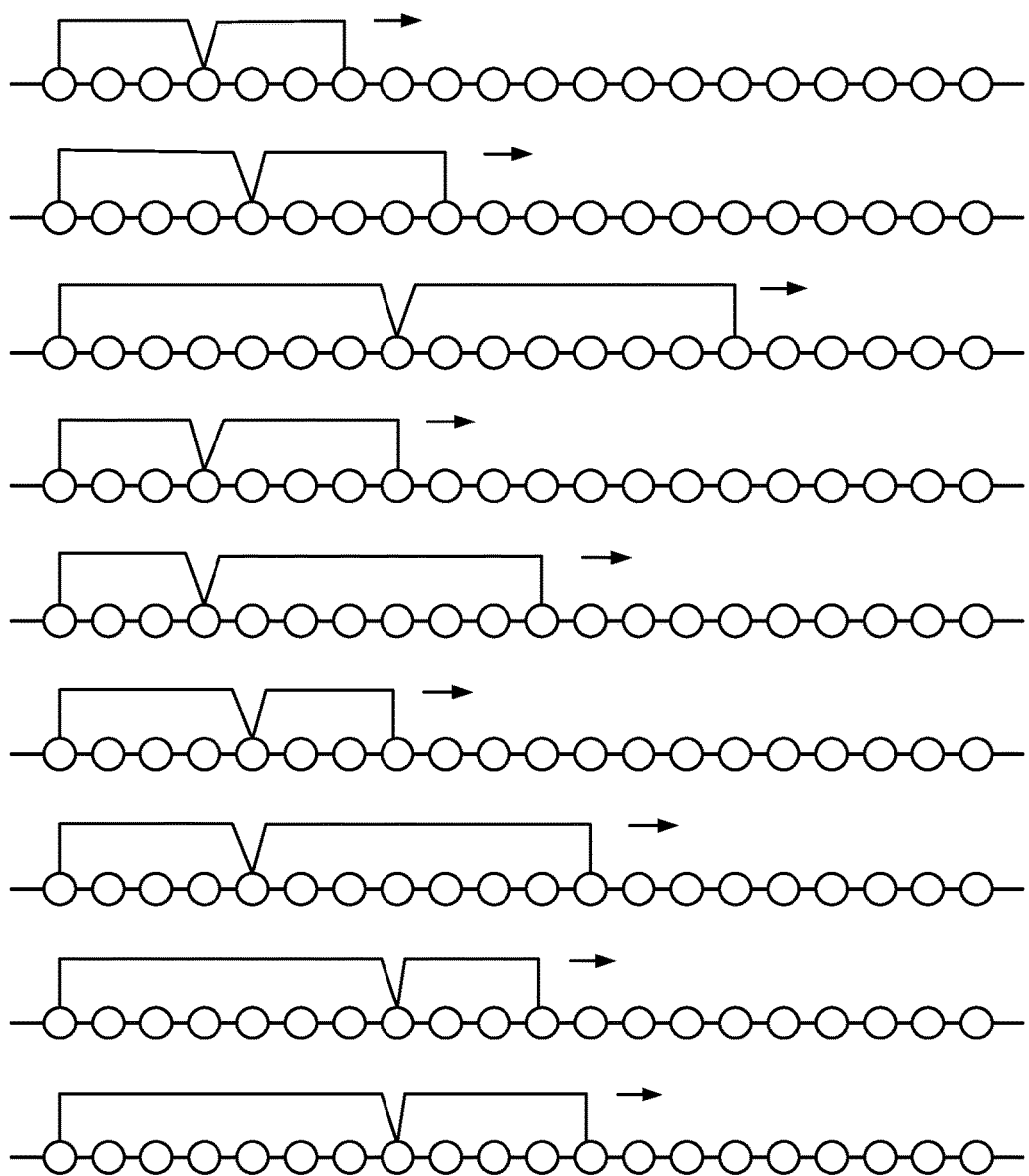
FIG. 1D provides examples of staple compositions for tandemly stapled SOS1 peptides.

Alternatively or in addition, peptides can include three internally cross-linked or stitched amino acids, e.g., yielding two staples arising from a common origin. A peptide stitch includes at least three internally cross-linked amino acids, wherein the middle of the three amino acids (referred to here as the core or central amino acid and shown in Table 1 (FIG. 23) as "i") forms an internal cross-link (between alpha carbons) with each of the two flanking modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 2, 3, or 6 amino acids (e.g., i, i−3, i, i−4, i, i−7 (shown in Table 1 (FIG. 23), i, i+3, i, i+4, i, i+7 (shown in Table 1 (FIG. 23), where "i" is the core amino acid). The number of amino acids on either side of the core (e.g., between the core amino acid and an amino acid cross-linked to the core) can be the same or different. Examples of such three amino acid containing peptide stitches are illustrated in FIG. 1D. In some instances, a stitch can include 3, 4, 5, or more internally cross-linked amino acids. In some instances, peptides can include 1, 2, 3, 4, 5, or more stitches.

In some embodiments, peptides herein can include a combination of at least one (e.g., 1, 2, 3, 4, or 5) staple and at least one (e.g., 1, 2, 3, 4, or 5) stitch.

Cross-linked peptides (e.g., stapled and/or stitched peptides) are generally referred to herein as SAHF peptides. Peptides can include cross-linked amino acids at one or more of the positions illustrated in Table 1.

In FIG. 23 (Table 1) positions of cross-links are indicated by symbols and the letter "i". For example, $i_{10}$ (C1) can be linked via a i+3 staple to $F_1$ or $G_0$ (also called i−3) or a i+4 staple to G1 or $F_0$ (also called i−4) or a i+7 staple to $C_2$ or $C_0$ (also called i−7). Of course, $i_{10}$ (C1) could be stitched to, for example $F_1$ (i+3) and C0 (i−7). In Table 1 (FIG. 23), the first row shows SEQ ID NO:1 and the second row shows an exemplary embodiment of SEQ ID NO: 1, SEQ ID NO:2.

Internal cross-links (e.g., staples and/or stitches) can be positioned on amino acids within a peptide to conserve the structural relationship of amino acids in the binding or interacting face of the peptide (e.g., to preserve the binding interface of a peptide). Alternatively, staples can placed on the interacting face as long as binding affinity or activity is not altered. Exemplary cross-linked peptides include SEQ ID NOs: 1-73.

In some instances, peptides herein do not include an internal cross-link that disrupts the binding interface of SEQ ID NO:2. For examples, in some instances, peptides do not include an internal cross-link between two or more (e.g., 2, 3, 4, 5, 6, 7, 8, 9, 10, or more) amino acids on the interacting face of SEQ ID NO:2.

Selection of amino acids for modification (e.g., to support an internal cross-link) can also be facilitated by staple scanning. The term "staple scan" refers to the synthesis of a library of stapled peptides whereby the location of the i and i+3; i and i+4; and i and i+7 single and multiple staple, or stitches, are positioned sequentially down the length of the peptide sequence, sampling all possible positions, to identify desired or optimal properties and activities for the stapled or stitched constructs. Examples of staple scanning methods are illustrated in the figures.

Suitable tethers are described herein and in US2005/0250680, PCT/US2008/058575, WO 2009/108261, and WO 2010/148335.

Amino acid side chains suitable for use in the peptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted.

As noted above an internal tether or cross-link can extend across the length of one helical turn (i.e., about 3.4 amino acids (i.e., i, i+3, or i, i+4) or two helical turns (i.e., about 7 amino acids (i.e., i, i+7). Accordingly, amino acids positioned at i and i+3; i and i+4; or i and i+7 are ideal candidates for chemical modification and cross-linking (see Table 1). Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . (wherein, " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful as are cross-links between $Xaa_2$ and $Xaa_5$, or between $Xaa_2$ and $Xaa_6$, or between $Xaa_2$ and $Xaa_9$, etc.

Polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (Bang, et al., J. Am. Chem. Soc. 126:1377). Alternately, large peptides are routinely synthesized using a convergent approach whereby fully protected fragments are specifically and sequentially reacted to form the full length desired product, after final deprotection, such as in the industrial synthesis of Fuzeon.

The invention features a modified polypeptide of Formula (V),

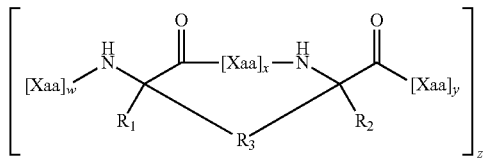

Formula (V)

or a pharmaceutically acceptable salt thereof,
wherein;
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene or alkynylene (e.g., a $C_6$, $C_7$, $C_8$, $C_{11}$, $C_{12}$ or $C_{13}$ alkylene), or $[R_4'—K—R_4]_n$; each of which is substituted with 0-6 $R_5$;

$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

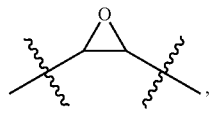

aziridine, episulfide, diol, amino alcohol;
$R_6$ is H, alkyl, or a therapeutic agent;
n is 2, 3, 4 or 6;
x is an integer from 2-10;

w and y are independently an integer from 0-100;
z is an integer from 1-10 (e.g., 1, 2, 3, 4, 5, 6, 7, 8, 9, 10);
and
each Xaa is independently an amino acid (e.g., one of the 20 naturally occurring amino acids or any naturally occurring non-naturally occurring amino acid);

wherein the polypeptide comprises at least 8 contiguous amino acids of SEQ ID NO:1, 2, 40, 41 or a variant thereof, or another polypeptide sequence described herein except that: (a) within the 8 contiguous (e.g., 9, 10, 11, 12, 13, 14, 15, 16, 17, 18, 19, 20, 21, 22, 23, 24, 24, 25, 26, 27, 28, 29, 30, 31, 32, 33, 34 or 35) amino acids of SEQ ID NO: 1, 2, 40, or 41 the side chains of at least one pair (e.g., one or two pairs) of amino acids separated by 2, 3 or 6 amino acids is replaced by the linking group, $R_3$, which connects the alpha carbons of the pair of amino acids as depicted in Formula I; and (b) the alpha carbon of the first of the pair of amino acids is substituted with $R_1$ as depicted in formula I and the alpha carbon of the second of the pair of amino acids is substituted with $R_2$ as depicted in Formula I.

In another aspect, the invention features a modified polypeptide of Formula (VI),

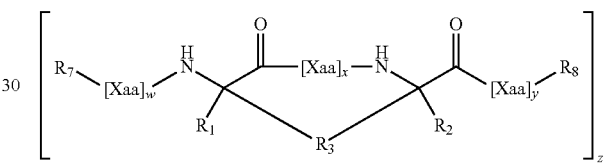

Formula (VI)

or a pharmaceutically acceptable salt thereof,
wherein;
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene or alkynylene (e.g., a $C_6$, $C_7$, $C_8$, $C_{11}$, $C_{12}$ or $C_{13}$ alkylene) or $[R_4'—K—R_4]_n$; each of which is substituted with 0-6 $R_5$;

$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);

$R_5$ is halo, alkyl, $OR_6$, $NHR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

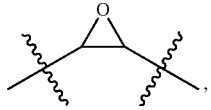 [SMILES: *C1OC1*]

aziridine, episulfide, diol, amino alcohol, diamine;
$R_6$ is H, alkyl, or a therapeutic agent;
n is 2, 3, 4, 5, or 6;
x is an integer from 2-10;
w and y are independently an integer from 0-100;
z is an integer from 1-10 (e.g., 1, 2, 3, 4, 5, 6, 7, 8, 9, 10);
and
each Xaa is independently an amino acid (e.g., one of the 20 naturally occurring amino acids or any naturally occurring non-naturally occurring amino acid);

R₇ is PEG, a tat protein, an affinity label, a targeting moiety, a fatty acid-derived acyl group, a biotin moiety, a fluorescent probe (e.g. fluorescein or rhodamine) linked via, e.g., a thiocarbamate or carbamate linkage;

R₈ is H, OH, NH₂, NHR$_{8a}$, NR$_{8a}$R$_{8b}$;

wherein the polypeptide comprises at least 8 contiguous amino acids (e.g., 9, 10, 11, 12, 13, 14, 15, 16, 17, 18, 19, 20, 21, 22, 23, 24, 24, 25, 26, 27, 28, 29, 30, 31, 32, 33, 34 or 35) of SEQ ID NO: 2 to 11, or another polypeptide sequence described herein except that: (a) within the 8 contiguous amino acids of SEQ ID NO: 1, 2, 40, 41 or another polypeptide sequence describe the side chains of at least one pair of amino acids separated by 2, 4 or 6 amino acids is replaced by the linking group, R₃, which connects the alpha carbons of the pair of amino acids as depicted in formula V; and (b) the alpha carbon of the first of the pair of amino acids is substituted with R₁ as depicted in Formula VI and the alpha carbon of the second of the pair of amino acids is substituted with R₂ as depicted in Formula VI.

In the case of Formula V or Formula VI, the following embodiments are among those disclosed.

In cases where x=2 (i.e., i+3 linkage), R3 can be a C7 alkylene, alkenylene. Where it is an alkenylene there can one or more double bonds. In cases where x=6 (i.e., i+4 linkage), R₃ can be a C11, C12 or C13 alkylene or alkenylene. Where it is an alkenylene there can one or more double bonds. In cases where x=3 (i.e., i+4 linkage), R₃ can be a C8 alkylene, alkenylene. Where it is an alkenylene there can one or more double bonds.

In certain instances, the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula V is depicted as

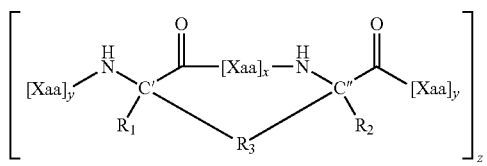

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration or the C' disubstituted stereocenter is in the S configuration and the C" disubstituted stereocenter is in the R configuration. The R₃ double bond may be in the E or Z stereochemical configuration. Similar configurations are possible for the carbons in Formula II corresponding to C' and C" in the formula depicted immediately above.

In some instances R₃ is [R₄—K—R₄']$_n$; and R₄ and R₄' are independently alkylene, alkenylene or alkynylene (e.g., each are independently a C1, C2, C3, C4, C5, C6, C7, C8, C9 or C10 alkylene, alkenylene or alkynylene In some instances, the polypeptide includes an amino acid sequence which, in addition to the amino acids side chains that are replaced by a cross-link, have 1, 2, 3, 4 or 5, 6, 7, 8, 9, 10, 11, 12 amino acid changes (e.g., conservative amino acid changes) in any of SEQ ID NOs: 2-11.

In some cases, of Formula V and Formula VI, the side chain is replaced by a group that includes a guanine nucleoside analog having the structure of Formula I.

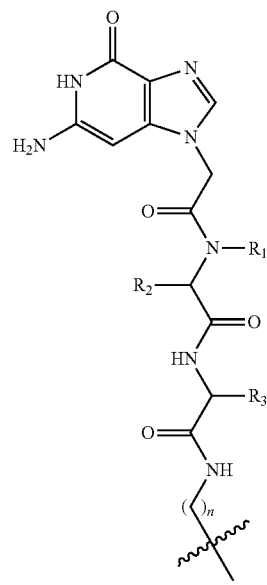

Formula I wherein R1, R2 and R3 are independently:

| R1 | R2 and R3 |
|---|---|
| —H | —H |
| —CH₃ | —CH₃ |
| —(CH₂)$_n$CH₃ | —(CH₂)$_n$CH₃ |
| ⌒⌒NHAc | ⌒O—P(=O)(OH)OH |
| ⌒N(H)—B-Als-FITC | ⌒O—P(=O)(O—CH₂—O—C(=O)—O—iPr)(O—CH₂—O—C(=O)—O—iPr) |
| ⌒⌒NH₂ | cyclopentane-diol-CH₂OH |
| ⌒O—P(=O)(OH)OH | cyclopentene-CH₂OH |
| cyclopentane-diol-CH₂OH | |

In some embodiments of a stapled, the side-chain of an amino acid is replaced by Formula II Formula II

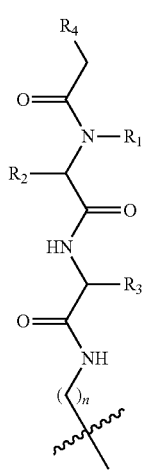

wherein: n is 1, 2, 3, or 4, R1, R2 and R3 are as in Formula I, and R₄ is selected from Formula III and Formula IV:

Formula III

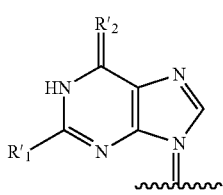

Formula IV

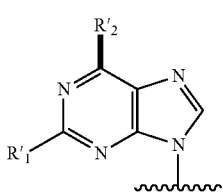

wherein R'1 and R'2 are independently:

| R'1 | R'2 |
|---|---|
| —NH₂ | —NH₂ |
| —H | =O |

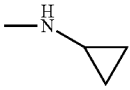

The tether can include an alkyl, alkenyl, or alkynyl moiety (e.g., $C_6$, $C_8$ or $C_{11}$ alkyl or a $C_6$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl). [Xaa]$_y$ and [Xaa]$_w$ are peptides that can independently comprise at least 1, 2, 3, 4, 5, 6, 7, 8, 9, 10, 11, 12, 13, 14, 15, 16, 17, 18, 19, 20, 21 or 22 contiguous amino acids of SEQ ID NOs: 1-11 and [Xaa]$_x$ is a peptide that can comprise 2, 3 or 6 contiguous amino acids of acids of SEQ ID NO: 1, 2, 40 or 41.

Peptides can contain one or more asymmetric centers and thus occur as racemates and racemic mixtures, single enantiomers, individual diastereomers and diastereomeric mixtures and geometric isomers (e.g. Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, EX. Stereochemistry of Carbon Compounds (McGraw-Hill, NY, 1962); Wilen, S. H. Tables of Resolving Agents and Optical Resolutions p. 268 (EX. Eliel, Ed., Univ. of Notre Dame Press, Notre Dame, Ind. 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

The symbol "⌇" when used as part of a molecular structure refers to a single bond or a trans or cis double bond.

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

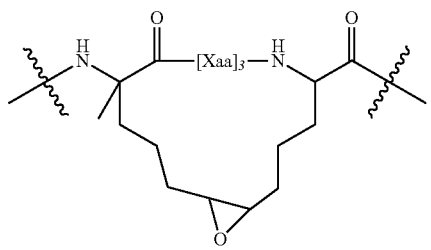

-continued

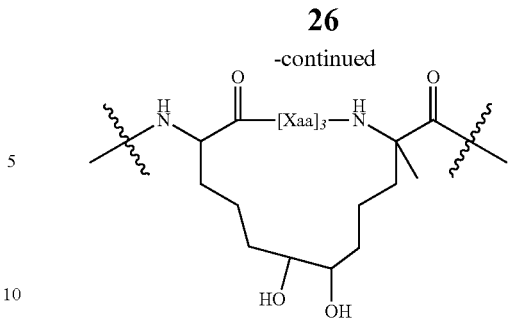

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., an anti-cancer agent such as rapamycin, vinblastine, taxol, etc.). Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

XO—(CH$_2$CH$_2$O)$_n$—CH$_2$CH$_2$—Y where n is 2 to 10,000 and X is H or a terminal modification, e.g., a C$_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —NH(CH$_2$)$_n$C(O)—, wherein n=2-20 can be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. U.S. Pat. No. 5,446,090 describes a bifunctional PEG linker and its use in forming conjugates having a peptide at each of the PEG linker termini.

The stapled peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

In some embodiments, the stapled peptides disclosed herein have an enhanced ability to penetrate cell membranes (e.g., relative to non-stapled peptides).

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH$_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or CH$_3$; and a fluoro-ketomethylene bond (C(O)—CFR or CFR—C(O) wherein R is H or F or CH$_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

α, α-Disubstituted non-natural amino acids containing olefinic side chains of varying length can be synthesized by known methods (Williams et al. J. Am. Chem. Soc., 113:9276, 1991; Schafmeister et al., J. Am. Chem Soc., 122:5891, 2000; and Bird et al., Methods Enzymol., 446:369, 2008; Bird et al, Current Protocols in Chemical Biology, 2011). For peptides where an i linked to i+7 staple is used (two turns of the helix stabilized) either one S5 amino acid and one R8 is used or one S8 amino acid and one R5 amino acid is used. R8 is synthesized using the same route, except that the starting chiral auxiliary confers the R-alkyl-stereoisomer. Also, 8-iodooctene is used in place of 5-iodopentene Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-S$_5$—OH, Fmoc-R$_8$—OH, Fmoc-R$_8$—OH, Fmoc-S$_8$—OH and Fmoc-R$_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

In some instances, peptides can include a detectable label. As used herein, a "label" refers to a moiety that has at least one element, isotope, or functional group incorporated into the moiety which enables detection of the peptide to which the label is attached. Labels can be directly attached (i.e., via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected.

Labels can include: labels that contain isotopic moieties, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; labels that include immune or immunoreactive moieties, which may be antibodies or antigens, which may be bound to enzymes {e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P and $^{18}$F.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Again, methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafmeister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety) and are described herein (see, e.g., Example 1).

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the cross-linked polypeptides of the invention can be assayed, for example, using the methods described below.

Assays to Determine α-Helicity:

Compounds are dissolved in an aqueous solution (e.g. 5 mM potassium phosphate solution at pH 7, or distilled H$_2$O, to concentrations of 25-50 μM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

Assays to Determine Melting Temperature (Tm):

Cross-linked or the unmodified template peptides are dissolved in distilled H$_2$O or other buffer or solvent (e.g. at a final concentration of 50 μM) and Tm is determined by measuring the change in ellipticity over a temperature range (e.g. 4 to 95° C.) on a spectropolarimeter (e.g., Jasco J-710, Aviv) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays:

The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The peptidomimetic macrocycles of the present invention may be subjected to in vitro enzymatic proteolysis (e.g. trypsin, chymotrypsin, pepsin) to assess for any change in degradation rate compared to a corresponding uncrosslinked or alternatively stapled polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of 1n[S] versus time.

Peptidomimetic macrocycles and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted, for example, by transferring 100 μL of sera to 2 ml centrifuge tubes followed by the addition of 10 μL of 50% formic acid and 500 μL acetonitrile and centrifugation at 14,000 RPM for 10 min at 4+/−2° C. The supernatants are then transferred to fresh 2 ml tubes and evaporated on Turbovap under N$_2$<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays:

A key benefit of peptide stapling is the translation of in vitro protease resistance into markedly improved pharmacokinetics in vivo.

In Vitro Binding Assays:

To assess the binding and affinity of peptidomimetic macrocycles and peptidomimetic precursors to acceptor proteins, a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

In Vitro Displacement Assays to Characterize Antagonists of Peptide-Protein Interactions:

To assess the binding and affinity of compounds that antagonize the interaction between a peptide and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

Binding Assays in Intact Cells:

It is possible to measure binding of peptides or cross-linked polypeptides to their natural acceptors on or in intact cells by immunoprecipitation experiments.

Cellular Penetrability Assays:

To measure the cell penetrability of peptides or cross-linked polypeptides, intact cells are incubated with fluoresceinated crosslinked polypeptides (10 μM) for 4 hrs in serum-free media or in media supplemented with human serum at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan® HCS Reader.

Pharmaceutical Compositions

One or more of the stabilized peptides disclosed herein (e.g., one or more of SEQ ID NOs: 1-121) can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions).

In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of cancer).

Pharmaceutical compositions of this invention can include one or more peptides and any pharmaceutically acceptable carrier and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using any one or more of the peptides or pharmaceutical compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; Li et al., Infect. Immun 57:3823-3827, 1989; Szu et al., Infect. Immun. 59:4555-4561, 1991; Szu et al., J. Exp. Med. 166:1510-1524, 1987; and Szu et al., Infect. Immun 62:4440-4444, 1994). Polymeric carriers can be a natural or a synthetic material containing one or more primary and/or secondary amino groups, azido groups, or carboxyl groups. Carriers can be water soluble.

Methods of Treatment

The disclosure includes methods of using the peptides herein for the prophylaxis and/or treatment of cancer. The terms "treat" or "treating," as used herein, refers to partially or completely alleviating, inhibiting, ameliorating, and/or relieving the disease or condition from which the subject is suffering.

In general, methods include selecting a subject and administering to the subject an effective amount of one or more of the peptides herein, e.g., in or as a pharmaceutical composition, and optionally repeating administration as required for the prophylaxis or treatment of a cancer, e.g., a RAS-dependent cancer.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Treatment Methods

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once.

EXAMPLES

Example 1: Stabilized SOS1 Peptides

Figure 2A:
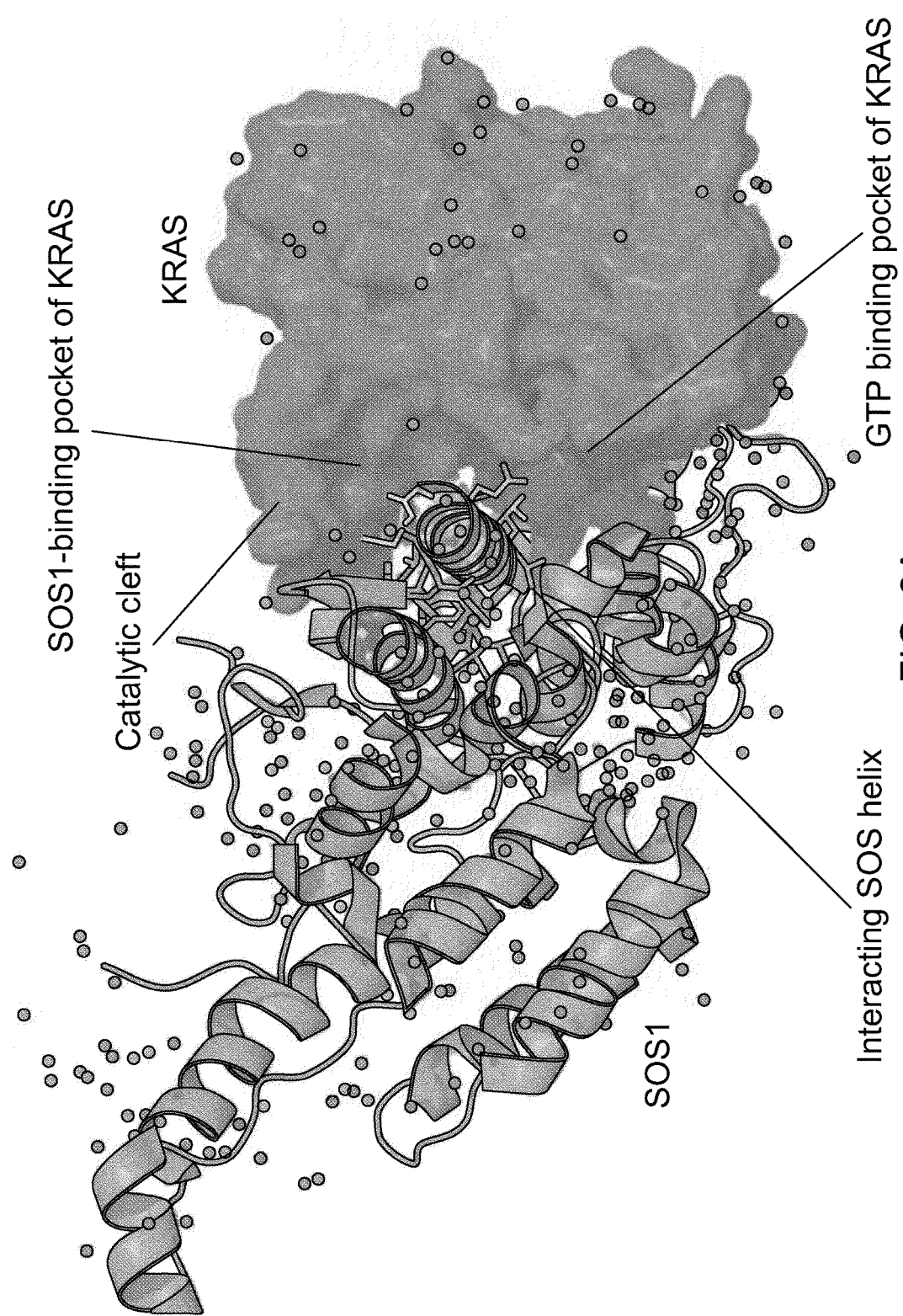

The structure of the complex between KRAS and its guanidine exchange factor activator SOS1 (PDB ID 3GFT) is shown in FIG. 2A. The indicated SOS1 helix binds to KRAS directly by engaging a defined pocket on KRAS. Of note, the GTP binding pocket, the catalytic site of KRAS, is situated adjacent to the SOS1 helix interaction site, but the SOS1 helix does not directly engage the catalytic site. FIG. 2B shows the structure of stabilized peptides in which hydrocarbon staples, labeled A through H, were inserted at a series of sequential i, i+4 positions along the length of the human SOS1 interaction helix corresponding to amino acids 929-944 of SOS 1 (SEQ ID NO:2). The SOS1 helix can be stapled using single (i, i+3), (i, i+4), or (i, i+7), or combinations thereof, at any position(s) along the length of the helix. Derivatizations at the N-termini with Ac and FITC were also performed. An Arg-Arg dipeptide was also introduced at select positions at the N- and C-termini, to enhance solubility, KRAS complex stability, and cellular uptake. Whereas the majority of staple positions shown emphasize staple installment (X=stapling aa) at the non-interacting face or at the boundary of the interaction surface, staples B and G, for example, were placed on the interacting face, potentially serving as negative/specificity controls for biochemical and biological experiments. Staples placed at the border of the binding interface can potentially enhance binding affinity by making additional contacts at the perimeter of the defined SOS1-binding site, a phenomenon previously observed for select stapled peptides of the MCL-1 BH3 domain upon engagement of the MCL-1 protein target (Stewart et al. Nat Chem Biol, 2010). FIGS. 3A-B depicts additional stabilized SOS1 peptides.

Example 2: SAH-SOS Peptides Bind Wild-Type KRAS with Nanomolar Affinity

A fluorescence polarization binding assay using recombinant KRAS protein (wild-type) and SAH-SOS peptides N-terminally derivatized with FITC-Ala (25 nM) revealed high affinity (20-100 nM) binding interactions for constructs containing the A, C, D, E, and H staples (FIG. 4). Importantly, SAH-SOS peptides containing staples B and G, which localize to the interaction surface, exhibited little to no binding activity. These data highlight the specificity of SAH-SOS A, C, D, E and H peptides for targeting wild-type KRAS, with staples B and G that interfere with binding surface engagement abrogating binding activity. The affinity of the various peptides is detailed in FIG. 5.

Example 3: SAH-SOS Peptides Also Bind with High Affinity to Recombinant KRAS Proteins Bearing Point Mutations Frequently Observed in Human Cancers Fluorescence polarization assays documented the capacity of SAH-SOS peptides to target KRAS proteins containing the clinical mutations H61Q, G12D, G12S, G12C and G12V with high affinities (FIGS. 6A-6B, 7, 8A-D) comparable to wild-type binding (FIGS. 4, 5).

Example 4: SAH-SOS Peptides Disrupt the Interaction Between KRAS and its Activating Protein, SOS1

SAH-SOS C2 peptide disrupted the association between KRAS and SOS1 protein in vitro, whereas the negative control construct SAH-SOS B2 that does not bind KRAS displayed no such activity (FIG. 9).

Example 5: SAH-SOS Peptides Inhibit the GTP Exchange Activity of KRAS

SAH-SOS peptides C2 and C3 reduce the GTP exchange activity of KRAS in vitro in a dose-responsive manner. KRAS was loaded with equimolar mant-GTP (a fluorescent GTP analog), and excess unlabeled GTP (10×) is then added to the reaction mixture. The observed decrease in fluorescence reflects the GTP turnover activity at the KRAS active site. SAH-SOS peptides reduce the GTP turnover activity, as reflected by a shift of the curves from the no peptide negative control toward the inhibited exchange (2 mM $MgCl_2$) positive control (FIG. 10).

SAH-SOS peptides also prevented GTP loading of KRAS proteins, including the wild type and clinically important G12D oncogenic variant. For both forms of KRAS protein, SAH-SOS C2 peptide dose-responsively inhibited mant-GTP loading, as evidenced by the increase in fluorescence. The negative control SAH-SOS B2 peptide had no effect (FIG. 11A-D).

Example 6: Cellular Penetrance of SAH-SOS Peptides

IXM high content epifluorescence microscopy documented the cellular uptake of SAH-SOS peptides C2 and C3 (0.5 μM) by mouse embryonic fibroblasts (FIG. 12A). Negative controls include DMSO and an unmodified/unstructured peptide of the BIM BH3 domain. The hydrocarbon-stapled BIM BH3 peptide, BIM SAHB$_A$ (aa 146-166) serves as a positive control for cellular uptake (as previously reported: Labelle et al. JCI, 2012). Microscopy was performed 4 hours after dosing cells with the corresponding FITC-conjugated peptides. Complimentary assays to evaluate cell penetrance, including confocal microscopy of treated pancreatic cancer cell lines such as Panc 10.05 (FIG. 12B) and fluorescence scan of lysates from SAH-SOS peptide-treated Panc 10.05 cells (FIG. 12C), were also employed. In each case, dose-dependent cellular uptake was observed both for SAH-SOS C2 and SAH-SOS B2 peptides.

Example 7: SAH-SOS Peptides Inhibit the Viability of RAS-Driven Cancer Cells SAH-SOS$_{C2}$, which demonstrates among the highest affinity for KRAS and its mutants, and manifests robust cellular uptake, impairs the viability of HeLa (cervical cancer, WT KRAS), HCT116 (colorectal cancer, KRAS G13D), and A549 (lung adenocarcinoma, KRAS G12S) cells as measured at 24 hours by CellTiter-Glo (FIG. 13).

Figure 15B:
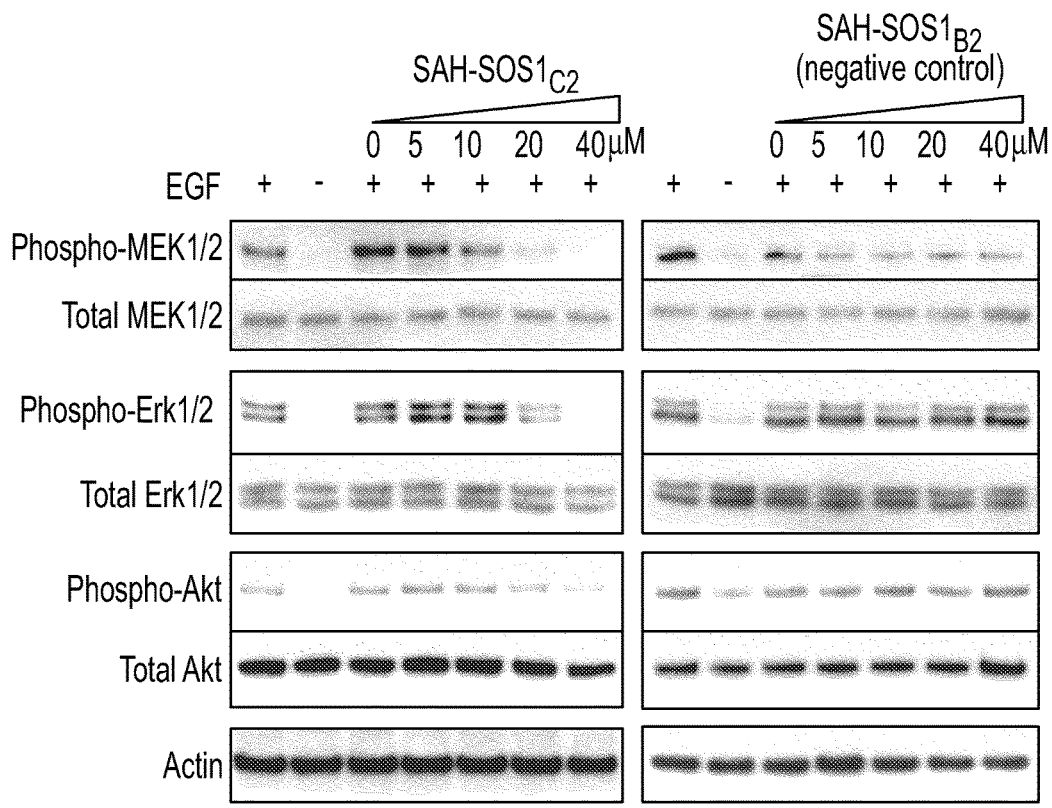

Example 8: Cytotoxicity of SAH-SOS Peptides Correlates with Inhibition of KRAS Signaling We tested a diversity of cancer cells lines to evaluate their susceptibility to SAH-SOS peptide treatments. SAH-SOS C2 peptide demonstrated anti-tumor activity in lung, pancreatic, colon, and cervical cancer cell lines (FIGS. 13 and 14). Consistent with the relative potency of SAH-SOSC2 vs. SAH-SOSC3 in cancer cell viability assays (FIG. 9), SAH-SOSC2 dose-responsively inhibited phosphorylation of the downstream KRAS targets phospho-MEK1/2, phospho-ERK1/2, phospho-Akt, phospho-S6K, and phospho-myc (FIG. 15). After 4 h incubation with the indicated peptides, HeLa (FIG. 15A) or Panc 10.05 (FIG. 15B) cells were treated with Endothelial Growth Factor (EGF), an upstream KRAS activator, and, lysates were prepared, subjected to electrophoresis, and western blotted with the indicated phospho-specific antibodies. Cells treated with or without EGF, in the absence of added peptide, served as positive and negative controls, respectively.

Example 9: SAH-SOS$_{C2}$ Inhibits Myc-Driven Expression in Response to EGF Stimulation HeLa cells transfected with a reporter construct containing luciferase under the control of the Myc promoter was treated with EGF and the indicated concentrations of SAH-SOS peptides (FIG. 16). The luciferase readout was normalized to cell viability and plotted as percent luciferase expression compared to baseline. SAH-SOS$_{C2}$ specifically inhibited myc-driven luciferase expression in response to EGF stimulation, which activates the KRAS pathway. No EGF treatment served as a negative control for the experiment.

Example 10: Derivatization of SAH-SOS Peptides to Jointly Target SOS1 and GTP Binding Sites on KRAS In order to further enhance KRAS targeting by SAH-SOS peptides, a second generation of constructs was designed based on derivatizating discrete residues facing the GTP-binding site with guanine peptide-nucleic acid monomers, with the goal of jointly engaging the SOS1 and GTP binding sites. Exemplary conjugation sites are shown in magenta (FIG. 17). By use of substituted (L938K), native (K942), or C-terminal appended lysine residues (and conversion of residual native lysines to arginines), G-monomer (Gmono) or glycine-conjugated G-monomer (G-Gmono) moieties were installed. The addition of glycine in the latter design served to lengthen the linker between the main chain and G-monomer to potentially provide greater reach into the GTP active site pocket. The chemical structures of SAH-SOS peptides containing guanine peptide-nucleic acid monomers for dual SOS1 and GTP binding site targeting of KRAS are depicted in FIG. 18.

Example 11: Increased KRAS Binding Affinity of Guanine Peptide-Nucleic Acid Monomer-Derivatized SAH-SOS Peptides Competitive fluorescence polarization binding assays conducted using wild-type KRAS protein (150 nM) and FITC-SAH-SOS$_{C2}$ (25 nM), demonstrated improved competition by the N-terminal acetylated SAH-SOS$_{C2}$ peptides containing the guanine peptide-nucleic acid moieties (FIG. 19). These data suggest that the KRAS binding potency of SAH-SOS peptides can be optimized by engaging both the SOS1 and GTP binding sites.

Example 12: Increased Inhibition of GTP Loading of KRAS by Guanine Peptide-Nucleic Acid Monomer-Derivatized SAH-SOS Peptides Fluorescent GTP analog, mant-GTP, was used to assess the GTP loading propensity of KRAS protein. SAH-SOS (Gmono) and SAH-SOS(G-Gmono) effectively inhibited nucleotide loading.

Example 13: Increased Cytotoxicity of KRAS-Driven Cancer Cells by Guanine Peptide-Nucleic Acid Monomer-Derivatized SAH-SOS Peptides Viability assays demonstrated enhanced cytotoxicity of HCT116 colon cancer cells in response to SAH-SOS$_{C2}$ peptides containing the guanine peptide-nucleic acid moieties compared to the parent peptide, as measured by CellTiter-Glo assay performed at 24 hours after treatment (FIG. 21). SAH-SOS$_{B2}$, which contains a staple position that interferes with the KRAS binding interface, served as a negative control for this experiment. Dose-dependent cytotoxic activity of guanine peptide-nucleic acid derivatives of SAH-SOSC2 was also observed in a series of pancreatic and lung cancer subtypes (FIG. 22). Consistent with the KRAS binding affinity hierarchy (FIG. 19), these cellular data suggest that the cytotoxicity of SAH-SOS peptides in cancer cells can be enhanced by the design of stapled peptide constructs that engage both the SOS1 and GTP binding sites.

Methods Used in the Examples

Peptide Synthesis

Peptide synthesis, hydrocarbon stapling by olefin metathesis, and N-terminal derivatizations were performed according to our established protocols [16, 17]. All peptides were purified by LC/MS to >95% purity and quantified by amino acid analysis. G-monomer-modified peptides were synthesized by using orthogonally (IVDDE) protected lysines in the peptide backbone and conjugating Gly-Gmonomer or Gmonomer using standard peptide synthesis conditions (conjugating the C-termini of the respective amino acids to the corresponding lysine-deprotected side chains). Fmoc-Bhoc-G-monomer was purchased from PNABio (USA). Alternatively, YHDES sequence (SEQ ID NO: 132) was attached by conjugating the C-terminus of tyrosine to the deprotected side chain of lysine. FITC/β-Ala or biotin/β-Ala or acetyl were attached to the N-termini of the peptides. For branched peptides, the FITC/β-Ala, biotin/β-Ala, or acetyl groups were attached to the N-termini of the branches (i.e. G-monomers; or serine in the YHDES sequence (SEQ ID NO: 132)).

Protein Purification

Wild-type human KRAS protein and the protein mutants Q61H, G12D, G12V, G12S and G12C, were expressed recombinantly in E. coli BL21(DE3) as N-terminal $His_6$-tag (SEQ ID NO: 133) fusions using the pET28-MHL expression vector. Expression was induced by 1 mM IPTG for 4 hours at 30° C. Collected bacterial pellets were resuspended in lysis buffer (20 mM Tris, 250 mM NaCl, pH 7.6), lysed by microfluidization (Microfluidics M-110L), and centrifuged at 45,000 rpm for 1 h at 4° C. (Beckman L-90K). The cleared cellular lysates were subjected to Ni affinity resin (New England Biolabs) chromatography followed by elution with 150 mM imidazole in 50 mM Tris, 250 mM NaCl, pH 7.8. Concentrated eluates were subjected to size exclusion chromatography and the corresponding monomeric peaks were collected. Protein concentration was determined by Bradford assay (BioRad) and UV absorbance measurements.

Fluorescence Polarization Assay

FP assays were performed as previously described [19]. Briefly, FITC-SAH-SOS peptides (e.g. 15 nM) were incubated with the indicated serial dilution of KRAS wild-type or mutant protein in binding buffer (50 mM Tris, 100 mM NaCl, pH 8.0) until equilibrium was reached. FP was measured using a SpectraMax M5 microplate reader (Molecular Devices). Dissociation constants ($K_D$) were calculated by nonlinear regression analysis of dose-response curves using Prism software (GraphPad). Competition FP assays were performed by using K-RAS proteins (e.g. 250 nM), FITC-SAH-SOS peptides (e.g. 15 nM), and for competition assays, a serial dilution of N-terminal acetylated SAH-SOS peptides.

Nucleotide Exchange Assay

Nucleotide exchange assays were performed as an association-dissociation experiment in which mant-GTP first associates with K-Ras followed by a dissociation step in which excess unlabeled GTP outcompetes mant-GTP, thus decreasing the fluorescence, as previously described[5]. A kinetic readout of fluorescence, corresponding to the dissociation step, was recorded on a Tecan X1000 fluorescence spectrometer (excitation 360 nm, emission 440 nm). The rate of nucleotide exchange was determined by fitting a single exponential function to the dissociation phase readout from the experiment (Prism software, GraphPad). Reactions were performed with the indicated amounts of SAH-SOS peptides in buffer containing 25 mM Tris (pH 7.5), 50 mM NaCl, 1 mM DTT with 2 μM wildtype KRAS, 2 μM mantGTP and 200 μM unlabeled GTP. 2 mM $MgCl_2$ was added as a negative control to inhibit mantGTP release.

Cellular Uptake Analysis

Cellular uptake was measured by IXM fluorescence microscopy. Briefly, wild-type MEFs were treated with 0.5 μM SAH-SOS peptide or the equivalent amount of control peptides (e.g. BIM BH3, BIM $SAHB_A$) for 4 hours in serum-free DMEM, and then stained with Hoechst dye and CellMask Orange (Invitrogen) for 10 min. The media was aspirated, and cells fixed with 4% paraformaldehyde for 10 min, washed 3× with PBS and imaged using ImageXpress Microscopy (high-throughput epifluorescence microscope, Molecular Devices). The data were analyzed and quantified with MetaXpress software.

Cell Viability Experiments

The indicated cell lines ($10^4$/well) were plated overnight (96-well format) in high-glucose DMEM media supplemented with 10% FBS, antibiotics and L-Glutamine. Media was aspirated, and SAH-SOS peptides added at the indicated concentrations in serum-free DMEM. Cell viability was measured at 24 hours using the CellTiter-Glo assay (Invitrogen). The plotted data represent percent viability as normalized to untreated controls.

Phospho-Western Blotting

HeLa cells ($10^5$/well) were plated overnight (12-well format) in high-glucose DMEM media supplemented with 10% FBS, antibiotics and L-Glutamine. After 24 hours, cells were treated with the indicated amounts of SAH-SOS peptides for 4 hours in serum-free DMEM, followed by the addition of EGF (50 ng/ml) (endothelial growth factor, Cell Signaling) for an additional 15 minute incubation. The cells were then lysed in buffer containing 0.5% NP-40, 50 mM Tris (pH 7.4), 150 mM NaCl, complete protease inhibitors and PhosphoOne phosphatase inhibitors (Roche), and collected lysates subjected to SDS-PAGE following by western blotting with anti-phospho-Erk1/2, phospho-S6K, phospho-myc (Cell Signaling), and actin (Sigma) antibodies.

Luciferase Reporter Assay

HeLa cells ($10^4$/well) were plated overnight (96-well format) in high-glucose DMEM media supplemented with 10% FBS, antibiotics and L-Glutamine. After 24 hour incubation, cells were transfected with pBV-Luc/Del-6 plasmid that includes a luciferase reporter under c-myc promoter, using Lipofectamine 2000 (Invitrogen) according to the manufacturer's protocol. Twenty-four hours after transfection, the cells were treated with the indicated amounts of SAH-SOS peptides for 4 hours in serum-free media, and then. EGF (50 ng/ml) was added for an additional 4 hour incubation. CellTiter-Glo and luciferase (Invitrogen) kits were used to quantify cell viability and luciferase expression, respectively. Viability data was used to normalize luciferase expression.

CITED PUBLICATIONS

1. Karnoub, A. E., and Weinberg, R. A. (2008). Ras oncogenes: split personalities. Nat Rev Mol Cell Biol 9, 517-531.
2. Hidalgo, M. (2010). Pancreatic cancer. N Engl J Med 362, 1605-1617.
3. Aguirre, A. J., Bardeesy, N., Sinha, M., Lopez, L., Tuveson, D. A., Horner, J., Redston, M. S., and DePinho, R. A. (2003). Activated Kras and Ink4a/Arf deficiency cooperate to produce metastatic pancreatic ductal adenocarcinoma. Genes Dev 17, 3112-3126.
4. Hingorani, S. R., Petricoin, E. F., Maitra, A., Rajapakse, V., King, C., Jacobetz, M. A., Ross, S., Conrads, T. P., Veenstra, T. D., Hitt, B. A., et al. (2003). Preinvasive and invasive ductal pancreatic cancer and its early detection in the mouse. Cancer Cell 4, 437-450.
5. Downward, J. (2003). Targeting RAS signalling pathways in cancer therapy. Nat Rev Cancer 3, 11-22.
6. Normanno, N., Tejpar, S., Morgillo, F., De Luca, A., Van Cutsem, E., and Ciardiello, F. (2009). Implications for KRAS status and EGFR-targeted therapies in metastatic CRC. Nat Rev Clin Oncol 6, 519-527.
7. Konstantinopoulos, P. A., Karamouzis, M. V., and Papavassiliou, A. G. (2007). Post-translational modifications and regulation of the RAS superfamily of GTPases as anticancer targets. Nat Rev Drug Discov 6, 541-555.
8. Whyte, D. B., Kirschmeier, P., Hockenberry, T. N., Nunez-Oliva, I., James, L., Catino, J. J., Bishop, W. R., and Pai, J. K. (1997). K- and N-Ras are geranylgeranylated in cells treated with farnesyl protein transferase inhibitors. J Biol Chem 272, 14459-14464.
9. Rinehart, J., Adjei, A. A., Lorusso, P. M., Waterhouse, D., Hecht, J. R., Natale, R. B., Hamid, O., Varterasian, M., Asbury, P., Kaldjian, E. P., et al. (2004). Multicenter phase II study of the oral MEK inhibitor, CI-1040, in patients with advanced non-small-cell lung, breast, colon, and pancreatic cancer. J Clin Oncol 22, 4456-4462.
10. Singh, A., and Settleman, J. (2009). Oncogenic K-ras "addiction" and synthetic lethality. Cell Cycle 8, 2676-2677.
11. Singh, A., Sweeney, M. F., Yu, M., Burger, A., Greninger, P., Benes, C., Haber, D. A., and Settleman, J. (2012). TAK1 inhibition promotes apoptosis in KRAS-dependent colon cancers. Cell 148, 639-650.
12. Luo, J., Emanuele, M. J., Li, D., Creighton, C. J., Schlabach, M. R., Westbrook, T. F., Wong, K. K., and Elledge, S. J. (2009). A genome-wide RNAi screen identifies multiple synthetic lethal interactions with the Ras oncogene. Cell 137, 835-848.
13. Patgiri, A., Yadav, K. K., Arora, P. S., and Bar-Sagi, D. (2011). An orthosteric inhibitor of the Ras-Sos interaction. Nat Chem Biol 7, 585-587.
14. Sun, Q., Burke, J. P., Phan, J., Burns, M. C., Olejniczak, E. T., Waterson, A. G., Lee, T., Rossanese, O. W., and Fesik, S. W. (2012). Discovery of small molecules that bind to K-Ras and inhibit Sos-mediated activation. Angew Chem Int Ed Engl 51, 6140-6143.
15. Maurer, T., Garrenton, L. S., Oh, A., Pitts, K., Anderson, D. J., Skelton, N. J., Fauber, B. P., Pan, B., Malek, S., Stokoe, D., et al. (2012). Small-molecule ligands bind to a distinct pocket in Ras and inhibit SOS-mediated nucleotide exchange activity. Proc Natl Acad Sci USA 109, 5299-5304.
16. Bird, G. H., Crannell, C. W. & Walensky, L. D. Chemical Synthesis of Hydrocarbon-Stapled Peptides for Protein Interaction Research and Therapeutic Targeting. *Curr Protoc Chem Biol* 3, 99-117 (2011).
17. Bird, G. H., Bernal, F., Pitter, K. & Walensky, L. D. Synthesis and biophysical characterization of stabilized alpha-helices of BCL-2 domains. *Methods Enzymol* 446, 369-86 (2008).
18. Braun, C. R. et al. Photoreactive stapled BH3 peptides to dissect the BCL-2 family interactome. *Chem Biol* 17, 1325-33 (2010).
19. Pitter, K., Bernal, F., Labelle, J. & Walensky, L. D. Dissection of the BCL-2 family signaling network with stabilized alpha-helices of BCL-2 domains. *Methods Enzymol* 446, 387-408 (2008).
20. Sun, Q. et al. Discovery of small molecules that bind to K-Ras and inhibit Sos-mediated activation. *Angew Chem Int Ed Engl* 51, 6140-3 (2012).
21. Chen, C. R., Kang, Y. & Massague, J. Defective repression of c-myc in breast cancer cells: A loss at the core of the transforming growth factor beta growth arrest program. *Proc Natl Acad Sci USA* 98, 992-9 (2001).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An internally cross-linked polypeptide comprising the amino acid sequence $A_0B_0C_0D_0E_0F_0G_0 \; A_1B_1C_1D_1E_1F_1G_1 \; A_2B_2$ (SEQ ID NO:1) wherein:

$A_0$ is F;

$B_0$ is F;

$C_0$ is G;

$D_0$ is I;

$E_0$ is Y;

$F_0$ is L;

$G_0$ is T;

$A_1$ is N;

$B_1$ is I;

$C_1$ is L, K, or K substituted with a guanine nucleoside or guanine nucleoside analog;

$D_1$ is K or R;

$E_1$ is T;

$F_1$ is E;

$G_1$ is E, K, or K substituted with a guanine nucleoside or guanine nucleoside analog;

$A_2$ is G; and $B_2$ is N;

wherein the side chains of two amino acids of SEQ ID NO:1 separated by three or six amino acids are cross-linked by an internal hydrocarbon staple; and wherein the internally cross-linked polypeptide binds a wild type KRAS protein.

2. A pharmaceutical composition comprising the internally cross-linked peptide of claim 1, and a pharmaceutically acceptable carrier.

3. The pharmaceutical composition of claim 2, comprising a medicament for the treatment of cancer.

4. A method for treating a cancer comprising administering to a patient in need thereof the internally cross-linked polypeptide of claim 1, wherein the patient harbors a mutant KRAS protein.

5. The internally cross-linked polypeptide of claim 1, wherein the internal hydrocarbon staple is between: $A_0$ and $A_1$, $B_0$ and $B_1$, $E_0$ and $B_1$, $B_1$ and $F_1$, $C_1$ and $G_1$, or $F_1$ and an amino acid immediately C-terminal to $B_2$.

6. The internally cross-linked polypeptide of claim 1, wherein the K substituted with a guanine nucleoside or guanine nucleoside analog comprises Formula II:

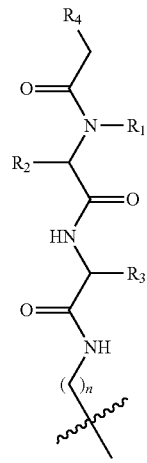

Formula II wherein:

n is 1, 2, 3, or 4;

$R_1$, $R_2$ and $R_3$ are as in Formula I, and $R_4$ is selected from Formula III and Formula IV

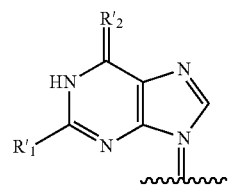

Formula III

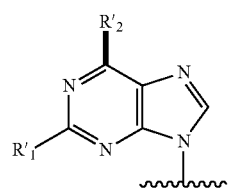

Formula IV wherein

R'1 is

—NH$_2$

—H;

R'2 in Formula III is O; and
R'2 in Formula IV is:

—NH$_2$

—NH-cyclopropyl or —OH.

7. The internally cross-linked polypeptide of claim 6, wherein the K substituted with a guanine nucleoside or guanine nucleoside analog comprises Formula Formula I wherein:

n is 1, 2, 3, or 4, and

R$_1$, R$_2$ and R$_3$ are independently:

| R$_1$ | R$_2$ and R$_3$ |
|---|---|
| —H | |
| —CH$_3$ | —H |
| —(CH$_2$)$_n$CH$_3$ | —CH$_3$ |
| —CH$_2$CH$_2$—NHAc | —(CH$_2$)$_n$CH$_3$ |
| —CH$_2$CH$_2$—NH—B-Ala-FITC | —(CH$_2$)$_n$—O—P(=O)(OH)—OH |
| —CH$_2$CH$_2$—NH$_2$ | phosphate bis(isopropyloxycarbonyloxymethyl) ester |
| | —(CH$_2$)$_n$—O—P(=O)(OH)—OH |
| | cyclopentane-diol-CH$_2$OH |
| | cyclopentane-ol-CH$_2$OH |
| | cyclopentene-CH$_2$OH |

8. The method of claim 4, wherein the mutant KRAS protein comprises one or more of the following mutations: H61Q, G12D, G12S, G12C, or G12V.

9. The internally cross-linked polypeptide of claim 1, comprising an amino acid sequence selected from the group consisting of:

FXGIYXTNILKTEEGN;  (SEQ ID NO: 12)

RRFXGIYXTNILKTEEGN;  (SEQ ID NO: 13)

FXGIYXTNILKTEEGNRR;  (SEQ ID NO: 14)

FFGIXLTNXLKTEEGN;  (SEQ ID NO: 16)

RRFFGIXLTNXLKTEEGN;  (SEQ ID NO: 17)

FFGIXLTNXLKTEEGNRR;  (SEQ ID NO: 18)

FFGIYLTNXLKTXEGN;  (SEQ ID NO: 19)

RRFFGIYLTNXLKTXEGN;  (SEQ ID NO: 20)

FFGIYLTNXLKTXEGNRR;  (SEQ ID NO: 21)

RRFFGIYLTNUCKTEXGN;  (SEQ ID NO: 22)

RRFFGIYLTNILKTXEGNX;  (SEQ ID NO: 23)

RRFXGIYLTNXLKTEEGN;  (SEQ ID NO: 25)

XFGIYLTXILKTEEGN;  (SEQ ID NO:80)

FXGIYLTNXLKTEEGN;  (SEQ ID NO:82)

RRFFGIXLTNXKKTEKGN;  (SEQ ID NO: 124)

RRFFGIXLTNXLKTEKGN;  (SEQ ID NO: 127)

-continued

```
                                    (SEQ ID NO: 129)
RRFFGIXLTNXLKKTEKGNPK;

(SEQ ID NO: 123)
RRFFGIXLTNXLRTEK(Gmono)GN;

(SEQ ID NO: 125)
RRFFGIXLTNXK(Gmono)RTEEGN;

(SEQ ID NO: 126)
RRFFGIXLTNXK(G-Gmono)RTEEGN;

(SEQ ID NO: 128)
RRFFGIXLTNXLRTEK(G-Gmono)GN;

(SEQ ID NO: 130)
RRFFGIXLTNXLRTEEGNPK(Gmono);
and (SEQ ID NO: 131)
RRFFGIXLTNXLRTEEGNPK(G-Gmono),
``` wherein K(Gmono) is a lysine modified with a G-monomer side-chain,

K(G-Gmono) is a lysine modified with a glycine-conjugated G-monomer side-chain, and the two "X" residues are the location of the internal hydrocarbon staple.

10. A pharmaceutical composition comprising the cross-linked peptides of claim 9, and a pharmaceutically acceptable carrier.

11. A method for treating a cancer comprising administering to a patient in need thereof the cross-linked polypeptide of claim 9, wherein the patient harbors a mutant KRAS protein.

12. The internally cross-linked polypeptide of claim 9, comprising the amino acid sequence FFGIYLTNXLKTX-EGN (SEQ ID NO: 19).

13. A pharmaceutical composition comprising the cross-linked peptides of claim 12, and a pharmaceutically acceptable carrier.

14. A method for treating a cancer comprising administering to a patient in need thereof the cross-linked polypeptide of claim 12, wherein the patient harbors a mutant KRAS protein.

15. An internally cross-linked polypeptide that binds a wild type KRAS protein, the internally cross-linked polypeptide comprising the amino acid sequence $A_0B_0C_0D_0E_0F_0G_0 A_1B_1C_1D_1E_1F_1G_1 A_2B_2$ (SEQ ID NO:1) wherein:

$A_0$ is F, Z or X;
$B_0$ is F, X, Z, or E;
$C_0$ is G or D;
$D_0$ is I or K;
$E_0$ is Y or X;
$F_0$ is L, X, R, or D;
$G_0$ is T, L, or E;
$A_1$ is N, X, or R;
$B_1$ is I or X;
$C_1$ is L, C, E, K, or K substituted with a guanine nucleoside or guanine nucleoside analog;
$D_1$ is K or R;
$E_1$ is T or A;
$F_1$ is E or X;
$G_1$ is E, C, K, or K substituted with a guanine nucleoside or guanine nucleoside analog;
$A_2$ is G or A; and
$B_2$ is N;

wherein X is a stapled amino acid and Z is (R)-2-amino-2-methyl-dec-9-enoic acid;

wherein the side chains of two X or Z amino acids separated by three or six amino acids are cross-linked by an internal hydrocarbon staple; and wherein the K substituted with a guanine nucleoside or guanine nucleoside analog comprises:

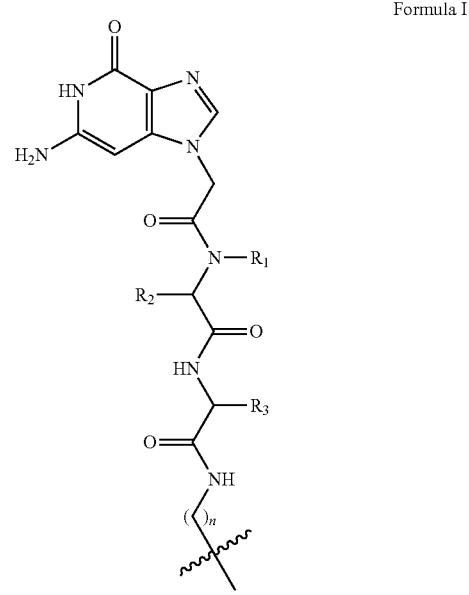

Formula I wherein n is 1, 2, 3, or 4 and $R_1$, $R_2$ and $R_3$ are independently:

| R1 | R2 and R3 |
|---|---|
| —H | —H |
| —CH$_3$ | —CH$_3$ |
| —(CH$_2$)$_n$CH$_3$ | —(CH$_2$)$_n$CH$_3$ |
| NHAc | phosphate group |
| B-Ala-FITC | bis-POC phosphate |
| NH$_2$ | cyclopentane diol |
| phosphonate | cyclopentene-ol |
| | cyclopentane diol-methanol | or Formula II:

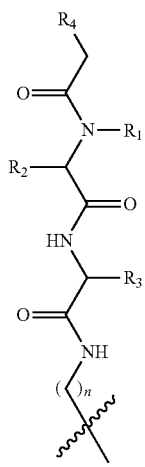

Formula II wherein: n is 1, 2, 3, or 4; $R_1$, $R_2$ and $R_3$ are as in Formula I, and $R_4$ is selected from Formula III and Formula IV

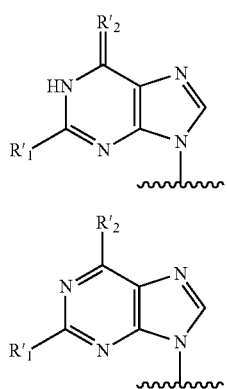

Formula III

Formula IV wherein:
R'1 is —NH$_2$ or —H;
R'2 in Formula III is O; and
R'2 in Formula IV is

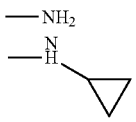

or —OH.

16. The internally cross-linked polypeptide of claim 15, wherein the internal hydrocarbon staple is between: $A_0$ and $A_1$, $B_0$ and $B_1$, $E_0$ and $B_1$, $B_1$ and $F_1$, $C_1$ and $G_1$, or $F_1$ and an amino acid immediately C-terminal to $B_2$.

17. A pharmaceutical composition comprising the internally cross-linked polypeptide of claim 15, and a pharmaceutically acceptable carrier.

18. The pharmaceutical composition of claim 17, comprising a medicament for the treatment of cancer.

19. A method for treating a cancer comprising administering to a patient in need thereof the internally cross-linked polypeptide of claim 15, wherein the patient harbors a mutant KRAS protein.

20. The method of claim 19, wherein the mutant KRAS protein comprises one or more of the following mutations: H61Q, G12D, G12S, G12C, or G12V.

21. The method of claim 4, wherein the cancer is a lung cancer, a pancreatic cancer, a colon cancer, or a cervical cancer.

22. The method of claim 11, wherein the cancer is a lung cancer, a pancreatic cancer, a colon cancer, or a cervical cancer.

23. The method of claim 14, wherein the cancer is a lung cancer, a pancreatic cancer, a colon cancer, or a cervical cancer.

24. The method of claim 19, wherein the cancer is a lung cancer, a pancreatic cancer, a colon cancer, or a cervical cancer.

* * * * *

UNITED STATES PATENT AND TRADEMARK OFFICE
CERTIFICATE OF CORRECTION

PATENT NO. : 10,087,215 B2
APPLICATION NO. : 14/772136
DATED : October 2, 2018
INVENTOR(S) : Elizaveta Leshchiner and Loren D. Walensky Page 1 of 1

It is certified that error appears in the above-identified patent and that said Letters Patent is hereby corrected as shown below:

In the Claims

Column 140, Line 52:
In Claim 9, delete "RRFFGIYLTNUCKTEXGN;" and insert -- RRFFGIYLTNIXKTEXGN; --, therefor.

Column 141, Line 54:
In Claim 15, delete "i s" and insert -- is --, therefor.

Column 142, Line 47:

In Claim 15, delete " 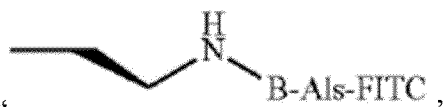 " and insert

-- 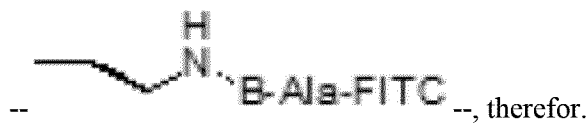 --, therefor.

Signed and Sealed this
Fifth Day of February, 2019

Andrei Iancu
*Director of the United States Patent and Trademark Office*